(12) United States Patent
Boll et al.

(10) Patent No.: US 8,980,854 B2
(45) Date of Patent: Mar. 17, 2015

(54) MIRNA COMPOUNDS FOR TREATMENT OF PROSTATE CARCINOMA

(75) Inventors: Kerstin Boll, Leipzig (DE); Friedemann Horn, Leipzig (DE); Jörg Hackermüller, Leipzig (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 13/390,028

(22) PCT Filed: Aug. 12, 2010

(86) PCT No.: PCT/EP2010/061795
§ 371 (c)(1),
(2), (4) Date: Sep. 24, 2012

(87) PCT Pub. No.: WO2011/018506
PCT Pub. Date: Feb. 17, 2011

(65) Prior Publication Data
US 2013/0018087 A1 Jan. 17, 2013

(30) Foreign Application Priority Data
Aug. 12, 2009 (EP) .................................. 09167719

(51) Int. Cl.
A61K 48/00 (2006.01)
C12N 15/113 (2010.01)

(52) U.S. Cl.
CPC ...... *C12N 15/1137* (2013.01); *C12N 2310/141* (2013.01); *C12N 2320/31* (2013.01); *C12N 2330/10* (2013.01)
USPC .......................................... 514/44; 536/24.5

(58) Field of Classification Search
None
See application file for complete search history.

(56) References Cited

FOREIGN PATENT DOCUMENTS

| EP | 2 088 208 A1 | 8/2009 |
|---|---|---|
| WO | WO 2006/137941 A2 | 12/2006 |
| WO | WO 2007/081740 A2 | 7/2007 |
| WO | WO 2009/036332 A1 | 3/2009 |
| WO | WO 2009/045356 A2 | 4/2009 |
| WO | WO 2009/049129 A1 | 4/2009 |
| WO | WO 2009/108860 A2 | 9/2009 |
| WO | WO 2009/112625 A1 | 9/2009 |

OTHER PUBLICATIONS

Saini et al. Clin Cancer Res 2011;17:5287-5298. Published OnlineFirst Dec. 15, 2010.*
Adegbola, O. and Pasternack, G.R., "A pp32-retinoblastoma protein complex modulates androgen receptor-mediated transcription and associates with components of the splicing machinery," *Biochemical and Biophysical Research Communications* 334:702-708, Elsevier Inc., United States (2005).
Amanatullah, D.F., et al., "Cell-Cycle Dysregulation and the Molecular Mechanisms of Prostate Cancer," *Frontiers in Bioscience* 5:372-390, Frontiers in Bioscience, Inc., United States (2000).
Ambs, S., et al., "Genomic Profiling of MicroRNA and Messenger RNA Reveals Deregulated MicroRNA Expression in Prostate Cancer," *Cancer Res.* 68:6162-6170, American Association for Cancer Research, United States (2008).
American Cancer Society, "Prostate Cancer," 2 pages, American Cancer Society, Inc., United States (2007).
Bartel, D.P., "MicroRNAs: Genomics, Biogenesis, Mechanism, and Function," *Cell* 116:281-297, Cell Press, United States (2004).
Benjamini, Y. and Hochberg, Y., "Controlling the False Discovery Rate: a Practical and Powerful Approach to Multiple Testing," *J. R. Statist. Soc. B* 57:289-300, Royal Statistical Society, England (1995).
Benndorf, D., et al., "Functional metaproteome analysis of protein extracts from contaminated soil and groundwater," *The ISME Journal* 1:224-234, International Society for Microbial Ecology, Nature Publishing Group, England (2007).
Benndorf, D., et al., "Identification of spore allergens from the indoor mould *Aspergillus versicolor*," *Allergy* 63:454-460, Blackwell Munksgaard, Denmark (2008).
Berth, M., et al., "The state of the art in the analysis of two-dimensional gel electrophoresis images," *Appl. Microbiol. Biotechnol.* 76:1223-1243, Springer-Verlag, Germany (2007).
*Bioinformatics and Computational Biology Solutions Using R and Bioconductor*, Gentleman, R., et al., ed., Springer Science+Business Media, Inc., New York, United States (2005).
Bolstad, B.M., et al., "A comparison of normalization methods for high density oligonucleotide array data based on variance and bias," *Bioinformatics* 19:185-193, Oxford University Press, England (2003).
Brummelkamp, T.R., et al., "A System for Stable Expression of Short Interfering RNAs in Mammalian Cells," *Science* 296:550-553, American Association for the Advancement of Science, United States (2002).
Bubendorf, L., et al., "Metastatic Patterns of Prostate Cancer: An Autopsy Study of 1,589 Patients," *Hum. Pathol.* 31:578-583, W.B. Saunders Company, United States (2000).
Bueno, M.J., et al., "Genetic and Epigenetic Silencing of MicroRNA-203 Enhances ABL1 and BCR-ABL1 Oncogene Expression," *Cancer Cell* 13:496-506, Elsevier Inc., United States (2008).
Cayouette, M. and Gravel, C., "Adenovirus-Mediated Gene Transfer of Ciliary Neurotrophic Factor Can Prevent Photoreceptor Degeneration in the Retinal Degeneration (rd) Mouse," *Human Gene Therapy* 8:423-430, Mary Ann Liebert, Inc., United States (1997).
Chen, C.-Z., "MicroRNAs as Oncogenes and Tumor Suppressors," *The New England Journal of Medicine* 353:1768-1771, Massachusetts Medical Society, United States (2005).
Cheng, W.-S., et al., "Characterization of the Androgen-Regulated Prostate-Specific T Cell Receptor γ-Chain Alternate Reading Frame Protein (TARP) Promoter," *Endocrinology* 144:3433-3440, The Endocrine Society, United States (2003).

(Continued)

*Primary Examiner* — Kimberly Chong
(74) *Attorney, Agent, or Firm* — Sterne, Kessler, Goldstein & Fox PLLC

(57) ABSTRACT

The invention inter alia relates to new pharmaceutical compositions comprising miRNAs miR-130a, miR-203 and miR-205, and their use for the treatment of cancer, in particular prostate cancer.

10 Claims, 16 Drawing Sheets

(56) References Cited

OTHER PUBLICATIONS

Davila, M., et al., "LIM Kinase 1 Is Essential for the Invasive Growth of Prostate Epithelial Cells," *The Journal of Biological Chemistry* 278:36868-36875, The American Society for Biochemistry and Molecular Biology, Inc., United States (2003).

Dehm, S.M. and Tindall, D.J., "Androgen Receptor Structural and Functional Elements: Role and Regulation in Prostate Cancer," *Molecular Endocrinology* 21:2855-2863, The Endocrine Society, United States (2007).

Edwards, J. and Bartlett, J.M.S., "The androgen receptor and signal-transduction pathways in hormone-refractory prostate cancer. Part 2: androgen-receptor cofactors and bypass pathways," *BJU International* 95:1327-1335, Blackwell Science Ltd, England (2005).

Eglitis, M.A., and Anderson, W.F., "Retroviral Vectors for Introduction of Genes into Mammalian Cells," *BioTechniques* 6:608-614, Eaton Pub. Co., United States (1988).

Eulalio, A., et al., "Getting to the Root of miRNA-Mediated Gene Silencing," *Cell* 132:9-14, Elsevier Inc., United States (2008).

Eulalio, A., et al., "Deadenylation is a widespread effect of miRNA regulation," *RNA* 15:21-32, RNA Society, Cold Spring Harbor Laboratory Press, United States (Jan. 2009).

Falcon, S. and Gentleman, R., "Using GOstats to test gene lists for GO term association," *Bioinformatics* 23:257-258, Oxford University Press, England (2007).

Filipowicz, W., et al., "Mechanisms of post-transcriptional regulation by microRNAs: are the answers in sight?," *Nature Reviews Genetics* 9:102-114, Nature Publishing Group, England (2008).

Galanis, A., et al., "Reactive oxygen species and HIF-1 signalling in cancer," *Cancer Letters* 266:12-20, Elsevier Ireland Ltd., Ireland (2008).

Galardi, S., et al., "miR-221 and miR-222 Expression Affects the Proliferation Potential of Human Prostate Carcinoma Cell Lines by Targeting p27$^{Kip1}$," *Journal of Biological Chemistry* 282:23716-23724, The American Society for Biochemistry and Molecular Biology, Inc., United States (2007).

Gandellini, P., et al., "miR-205 Exerts Tumor-Suppressive Functions in Human Prostate through Down-regulation of Protein Kinase Cε," *Cancer Res.* 69:2287-2295, American Association for Cancer Research, United States (Mar. 2009).

Gavrielides, M.V., et al., "Androgens Regulate Protein Kinase CD Transcription and Modulate Its Apoptotic Function in Prostate Cancer Cells," *Cancer Res.* 66:11792-11801, American Association for Cancer Research, United States (2006).

Georgieva, D., et al., "Comparative Analysis of the Venom Proteomes of *Vipera ammodytes ammodytes* and *Vipera ammodytes meridionalis*," *Journal of Proteome Research* 7:866-886, American Chemical Society, United States (2008).

Giering, J.C., et al., "Expression of shRNA From a Tissue-specific pol II Promoter Is an Effective and Safe RNAi Therapeutic," *Molecular Therapy* 16:1630-1636, The American Society of Gene Therapy, United States (2008).

Gleason, D.F., et al., "Prediction of Prognosis for Prostatic Adenocarcinoma by Combined Histological Grading and Clinical Staging," *The Journal of Urology* 111:58-64, The Williams & Wilkins Co., United States (1974).

Gold, L., et al., "Diversity of Oligonucleotide Functions," *Annu. Rev. Biochem.* 64:763-797, Annual Reviews Inc., United States (1995).

Grad, J.M., et al., "The Androgen Receptor (AR) Amino-Terminus Imposes Androgen-Specific Regulation of AR Gene Expression via an Exonic Enhancer," *Endocrinology* 142:1107-1116, The Endocrine Society, United States (2001).

Grayhack, J.T., et al., "Carcinoma of the Prostate: Hormonal Therapy," *Cancer* 60:589-601, American Cancer Society, United States (1987).

Grishok, A., et al., "Genes and Mechanisms Related to RNA Interference Regulate Expression of the Small Temporal RNAs that Control *C. elegans* Developmental Timing," *Cell* 106:23-34, Cell Press, United States (2001).

Hååg, P., et al., "Androgen receptor down regulation by small interference RNA induces cell growth inhibition in androgen sensitive as well as in androgen independent prostate cancer cells," *Journal of Steroid Biochemistry & Molecular Biology* 96:251-258, Elsevier Ltd., England (2005).

Hammond, S.M., "MicroRNAs as oncogenes," *Current Opinion in Genetics & Development* 16:4-9, Elsevier Ltd., England (2006).

Hammond, S.M., "MicroRNAs as tumor suppressors," *Nature Genetics* 39:582-583, Nature Publishing Group, England (2007).

Harada, M., et al., "Analysis of Bone Metastasis of Prostatic Adenocarcinoma in 137 Autopsy Cases," *Adv. Exp. Med. Biol.* 324:173-182, Plenum Press, United States (1992).

Harper, M.E., et al., "Relationship of Proliferating Cell Nuclear Antigen (PCNA) in Prostatic Carcinomas to Various Clinical Parameters," *The Prostate* 20:243-253, Wiley-Liss, Inc., United States (1992).

He, X.-Y., et al., "Oxidative 3α-hydroxysteroid dehydrogenase activity of human type 10 17β-hydroxysteroid dehydrogenase," *Journal of Steroid Biochemistry & Molecular Biology* 87:191-198, Elsevier Ltd., England (2003).

Hod, Y., "Differential Control of Apoptosis by DJ-1 in Prostate Benign and Cancer Cells," *Journal of Cellular Biochemistry* 92:1221-1233, Wiley-Liss, Inc., United States (2004).

Hsieh, J.-T., et al., "Autocrine Regulation of Prostate-specific Antigen Gene Expression in a Human Prostatic Cancer (LNCaP) Subline," *Cancer Research* 53:2852-2857, American Association for Cancer Research, United States (1993).

Huggins, C., "Endocrine-Induced Regression of Cancers," *Cancer Research* 27:1925-1930, American Association for Cancer Research, United States (1967).

Huggins, C. and Hodges, C.V., "Studies on Prostatic Cancer: I. The Effect of Castration, of Estrogen and of Androgen Injection on Serum Phosphatases in Metastatic Carcinoma of the Prostate," *CA Cancer J Clin.* 22:232-240, American Cancer Society, United States (1972).

Hutvágner, G., et al., "A Cellular Function for the RNA-Interference Enzyme Dicer in the Maturation of the let-7 Small Temporal RNA," *Science* 293:834-838, American Association for the Advancement of Science, United States (2001).

Jehmlich, N., et al., "Protein-based stable isotope probing (Protein-SIP) reveals active species within anoxic mixed cultures," *The ISME Journal* 2:1122-1133, International Society for Microbial Ecology, Nature Publishing Group, England (2008).

Ketting, R.F., et al., "Dicer functions in RNA interference and in synthesis of small RNA involved in developmental timing in *C. elegans*," *Genes & Development* 15:2654-2659, Cold Spring Harbor Laboratory Press, United States (2001).

Koochekpour, S., et al., "Amplification and Overexpression of Prosaposin in Prostate Cancer," *Genes, Chromosomes & Cancer* 44:351-364, Wiley-Liss, Inc., United States (2005).

Koochekpour, S., et al., "Prosaposin Upregulates AR and PSA Expression and Activity in Prostate Cancer Cells (LNCaP)" *The Prostate* 67:178-189, Wiley-Liss, Inc., United States (2006).

Krützfeldt, J., et al., "Silencing of microRNAs in vivo with 'antagomirs,'" *Nature* 438:685-689, Nature Publishing Group, England (2005).

Lagos-Quintana, M., et al., "Identification of Novel Genes Coding for Small Expressed RNAs," *Science* 294:853-858, American Association for the Advancement of Science, United States (2001).

Lewis, B.P., et al., "Conserved Seed Pairing, Often Flanked by Adenosines, Indicates that Thousands of Human Genes are MicroRNA Targets," *Cell* 120: 15-20, Elsevier Inc., United States (2005).

Majid, S., et al., "Induction of tumor suppressor genes IL24 and IL32 by microRNA-205 in prostate cancer," *AACR 101st Annual Meeting*: Presentation Abstract, American Association for Cancer Research, United States (Apr. 2010).

Mattie, M.D., et al., "Optimized high-throughput microRNA expression profiling provides novel biomarker assessment of clinical prostate and breast cancer biopsies," *Molecular Cancer* 5:24, BioMed Central Ltd, England (2006).

Meehan, K.L. and Sadar, M.D., "Quantitative profiling of LNCaP prostate cancer cells using isotope-coded affinity tags and mass spectrometry," *Proteomics* 4:1116-1134, Wiley-VCH Verlag GmbH & Co. KGaA, Germany (2004).

(56) References Cited

OTHER PUBLICATIONS

Mercatelli, N., et al., "The Inhibition of the Highly Expressed Mir-221 and Mir-222 Impairs the Growth of Prostate Carcinoma Xenografts in Mice," *PLoS One* 3:e4029, PLOS, England (2008).

Miller, H.I., "Human Gene Therapy: Part of a Therapeutic Continuum," *Human Gene Therapy* 1:3-4, Mary Ann Liebert, Inc., United States (1990).

Miyagi, T., et al., "Antitumor effect of reduction of 150-kDa oxygen-regulated protein expression on human prostate cancer cells," *International Journal of Urology* 9:577-585, The Japanese Urological Association, Japan (2002).

Murtha, P., et al., "Androgen Induction of a Human Prostate-Specific Kallikrein, hKLK2: Characterization of an Androgen Response Element in the 5' Promoter Region of the Gene," *Biochemistry* 32:6459-6464, American Chemical Society, United States (1993).

Naldini, L., et al., "In Vivo Gene Delivery and Stable Transduction of Nondividing Cells by a Lentiviral Vector," *Science* 272:263-267, American Association for the Advancement of Science, United States (1996).

Nantermet, P.V., et al., "Identification of Genetic Pathways Activated by the Androgen Receptor during the Induction of Proliferation in the Ventral Prostate Gland," *The Journal of Biological Chemistry* 279:1310-1322, The American Society for Biochemistry and Molecular Biology, Inc., United States (2004).

Needleman, S.B. and Wunsch, C.D., "A General Method Applicable to the Search for Similarities in the Amino Acid Sequence of Two Proteins," *J. Mol. Biol.* 48:443-453, Academic Press Ltd., England (1970).

Nielsen, P.E., "Applications of peptide nucleic acids," *Current Opinion in Biotechnology* 10:71-75, Elsevier Science Ltd, England (1999).

Nielsen, P.E., et al., "Sequence-Selective Recognition of DNA by Strand Displacement with a Thymine-Substituted Polyamide," *Science* 254:1497-1500, American Association for the Advancement of Science, United States (1991).

Ohtsuka, E., et al., "An Alternative Approach to Deoxyoligonucleotides as Hybridization Probes by Insertion of Deoxyinosine at Ambiguous Codon Positions," *The Journal of Biological Chemistry* 260:2605-2608, The American Society of Biological Chemists Inc., United States (1985).

Ozen, M., et al., "Widespread deregulation of microRNA expression in human prostate cancer," *Oncogene* 27:1788-1793, Nature Publishing Group, England (2008).

Park, S.-Y., et al., "Peroxiredoxin 1 Interacts with Androgen Receptor and Enhances Its Transactivation," *Cancer Res.* 67:9294-9303, American Association for Cancer Research, United States (2007).

Pienta, K.J. and Bradley, D., "Mechanisms Underlying the Development of Androgen-Independent Prostate Cancer," *Clin. Cancer Res.* 12:1665-1671, American Association for Cancer Research, United States (2006).

Pitkänen-Arsiola, T., et al., "Androgen and Anti-Androgen Treatment Modulates Androgen Receptor Activity and DJ-1 Stability," *The Prostate* 66:1177-1193, Wiley-Liss, Inc., United States (2006).

Porkka, K.P., et al., "MicroRNA Expression Profiling in Prostate Cancer," *Cancer Res.* 67:6130-6135, American Association for Cancer Research, United States (2007).

Prueitt, R.L., et al., "Expression of microRNAs and Protein-coding Genes Associated with Perineural Invasion in Prostate Cancer," *Prostate* 68:1152-1164, Wiley-Liss, United States (2008).

Riegman, P.H.J., et al., "The Promoter of the Prostate-Specific Antigen Gene Contains a Functional Androgen Responsive Element," *Molecular Endocrinology* 5:1921-1930, The Endocrine Society, United States (1991).

Rossolini, G.M., et al., "Use of deoxyinosine-containing primers vs degenerate primers for polymerase chain reaction based on ambiguous sequence information," *Molecular and Cellular Probes* 8:91-98, Academic Press Limited, England (1994).

Roudier, M.P., et al., "Phenotypic Heterogeneity of End-Stage Prostate Carcinoma Metastatic to Bone," *Hum. Pathol.* 34:646-653, Elsevier Inc., United States (2003).

Saeed, B., et al., "Apoptotic Program Is Initiated But Not Completed in LNCaP Cells in Response to Growth in Charcoal-Stripped Media," *The Prostate* 31:145-152, Wiley-Liss, Inc., United States (1997).

Saini, S., et al., "Regulatory role of miR-203 in prostate cancer," *AACR 101st Annual Meeting*: Presentation Abstract, American Association for Cancer Research, United States (Apr. 2010).

Saitoh, H., et al., "Metastatic Patterns of Prostatic Cancer: Correlation Between Sites and Number of Organs Involved," *Cancer* 54:3078-3084, American Cancer Society, United States (1984).

Segawa, T., et al., "Androgen-induced expression of endoplasmic reticulum (ER) stress response genes in prostate cancer cells," *Oncogene* 21:8749-8758, Nature Publishing Group, England (2002).

Shah, R.B., et al., "Androgen-Independent Prostate Cancer Is a Heterogeneous Group of Diseases: Lessons from a Rapid Autopsy Program," *Cancer Research* 64:9209-9216, American Association for Cancer Research, United States (2004).

Shi, X.-B., et al., "An androgen-regulated miRNA suppresses Bak1 expression and induces androgen-independent growth of prostate cancer cells," *PNAS* 104:19983-19988, The National Academy of Sciences of the USA, United States (2007).

Shi, X.-B., et al., "microRNAs and prostate cancer," *J. Cell. Mol. Med.* 12:1456-1465, Foundation for Cellular and Molecular Medicine, Blackwell Publishing Ltd, England (2008).

Smith, T.F. and Waterman, M.S., "Identification of Common Molecular Subsequences," *J Mol. Biol.* 147:195-197, Academic Press Inc. (London) Ltd., England (1981).

Smyth, G.K., "Linear Models and Empirical Bayes Methods for Assessing Differential Expression in Microarray Experiments," *Statistical Applications in Genetics and Molecular Biology* 3:1-25, The Berkeley Electronic Press, United States (2004).

Stanford, J.L., et al., "Dense genome-wide SNP linkage scan in 301 hereditary prostate cancer families identifies multiple regions with suggestive evidence for linkage," *Human Molecular Genetics* 18:1839-1848, Oxford University Press, England (Feb. 2009).

Stephan, C., et al., "PSA and other tissue kallikreins for prostate cancer detection," *European Journal of Cancer* 43:1918-1926, Elsevier Ltd., England (2007).

Sun, T., et al., "The Role of microRNA-221 and microRNA-222 in Androgen-Independent Prostate Cancer Cell Lines," *Cancer Res.* 69:3356-3363, American Association for Cancer Research, United States (Apr. 2009).

Tillman, J.E., et al., "DJ-1 Binds Androgen Receptor Directly and Mediates Its Activity in Hormonally Treated Prostate Cancer Cells," *Cancer Res.* 67:4630-4637, American Association for Cancer Research, United States (2007).

Ullmann, K., "MicroRNAs lost during prostate carcinoma pathogenesis cooperatively regulate mRNAs involved in androgen receptor signaling," *J Neurochem.* 110 (Suppl. 1):99, International Society for Neurochemistry, Switzerland (May 2009).

Van De Wetering, M., et al., "Specific inhibition of gene expression using a stably integrated, inducible small-interfering-RNA vector," *EMBO reports* 4:609-615, European Molecular Biology Organization, Nature Publishing Group, England (2003).

Van Den Bemd, G.-J.C.M., et al., "Mass Spectrometric Identification of Human Prostate Cancer-derived Proteins in Serum of Xenograft-bearing Mice," *Molecular & Cellular Proteomics* 5.10:1830-1839, The American Society for Biochemistry and Molecular Biology, Inc., United States (2006).

Wang, W., et al., "NDRG3 is an androgen regulated and prostate enriched gene that promotes in vitro and in vivo prostate cancer cell growth," *Int. J Cancer* 124:521-530, Wiley-Liss, Inc., United States (2008).

Wolfgang, C.D., et al., "TARP: A nuclear protein expressed in prostate and breast cancer cells derived from an alternate reading frame of the T cell receptor γ chain locus," *PNAS* 97:9437-9442, National Academy of Sciences, United States (2000).

(56) References Cited

OTHER PUBLICATIONS

Xiao, F., et al., "miRecords: an integrated resource for microRNA-target interactions," *Nucleic Acids Research* 37:D105-D110, Oxford University Press, England (Jan. 2009).

Zhu, N. and Wang, Z., "Calreticulin Expression Is Associated with Androgen Regulation of the Sensitivity to Calcium Ionophore-induced Apoptosis in LNCaP Prostate Cancer Cells," *Cancer Research* 59:1896-1902, American Association for Cancer Research, United States (1999).

International Search Report and Written Opinion for International Application No. PCT/EP2010/061795, European Patent Office, Netherlands, mailed on Nov. 3, 2010.

Place, R.F., et al., "A role for miR-205 in prostate cancer," *AACR 100th Annual Meeting*: Presentation Abstract, American Association for Cancer Research, United States (Apr. 2009).

Written Opinion for European Application No. EP 09 16 7719, The Hague, Netherlands, 2010.

European Search Report for European Application No. EP 09 16 7718, The Hague, Netherland, completed on Jan. 6, 2010.

\* cited by examiner

SEQUENCE LISTING

<160> NUMBER OF SEQ ID NOS: 48

<210> SEQ ID NO 1
<211> LENGTH: 89
<212> TYPE: RNA
<213> ORGANISM: Homo sapiens

<400> SEQUENCE: 1
ugcugcuggc cagagcucuu uucacauugu gcuacugucu gcaccuguca cuagcagugc    60
aauguuaaaa gggcauuggc cguguagug                                     89

<210> SEQ ID NO 2
<211> LENGTH: 22
<212> TYPE: RNA
<213> ORGANISM: Homo sapiens

<400> SEQUENCE: 2
cagugcaaug uuaaaagggc au                                            22

<210> SEQ ID NO 3
<211> LENGTH: 22
<212> TYPE: DNA
<213> ORGANISM: Homo sapiens

<400> SEQUENCE: 3
cagtgcaatg ttaaaagggc at                                            22

<210> SEQ ID NO 4
<211> LENGTH: 110
<212> TYPE: RNA
<213> ORGANISM: Homo sapiens

<400> SEQUENCE: 4
guguugggga cucgcgcgcu ggguccagug guucuuaaca guucaacagu ucuguagcgc    60
aauugugaaa uguuuaggac cacuagaccc ggcgggcgcg gcgacagcga               110

<210> SEQ ID NO 5
<211> LENGTH: 22
<212> TYPE: RNA
<213> ORGANISM: Homo sapiens

<400> SEQUENCE: 5
gugaaauguu uaggaccacu ag                                            22

<210> SEQ ID NO 6
<211> LENGTH: 22
<212> TYPE: DNA
<213> ORGANISM: Homo sapiens

<400> SEQUENCE: 6
gtgaaatgtt taggaccact ag                                            22

<210> SEQ ID NO 7
<211> LENGTH: 110
<212> TYPE: RNA
<213> ORGANISM: Homo sapiens

<400> SEQUENCE: 7
aaagauccuc agacaaucca ugugcuucuc uugccuuuca uuccaccgga gucugucuca    60
uacccaacca gauucagug gagugaaguu caggaggcau ggagcugaca               110

```
<210> SEQ ID NO 8
<211> LENGTH: 22
<212> TYPE: RNA
<213> ORGANISM: Homo sapiens

<400> SEQUENCE: 8
uccuucauuc caccggaguc ug                                              22

<210> SEQ ID NO 9
<211> LENGTH: 22
<212> TYPE: DNA
<213> ORGANISM: Homo sapiens

<400> SEQUENCE: 9
tccttcattc caccggagtc tg                                              22

<210> SEQ ID NO 10
<211> LENGTH: 66
<212> TYPE: DNA
<213> ORGANISM: Artificial
<220> FEATURE:
<223> OTHER INFORMATION: pSUPER Insert mir130a fwd

<400> SEQUENCE: 10 gatccccag tgcaatgtta aagggcatt tcaagagaat gccctttttaa cattgcactg      60 tttttta                                                               66

<210> SEQ ID NO 11
<211> LENGTH: 66
<212> TYPE: DNA
<213> ORGANISM: Artificial
<220> FEATURE:
<223> OTHER INFORMATION: pSUPER Insert mir130a rev

<400> SEQUENCE: 11
agcttaaaaa cagtgcaatg ttaaaagggc attctcttga aatgcccttt taacattgca     60
ctgggg                                                                66

<210> SEQ ID NO 12
<211> LENGTH: 66
<212> TYPE: DNA
<213> ORGANISM: Artificial
<220> FEATURE:
<223> OTHER INFORMATION: pSUPER Insert mir203 fwd

<400> SEQUENCE: 12
gatccccgtg aaatgtttag gaccactagt tcaagagact agtggtccta aacatttcac     60
tttttta                                                               66

<210> SEQ ID NO 13
<211> LENGTH: 66
<212> TYPE: DNA
<213> ORGANISM: Artificial
<220> FEATURE:
<223> OTHER INFORMATION: pSUPER Insert mir203 rev

<400> SEQUENCE: 13
agcttaaaaa gtgaaatgtt taggaccact agtctcttga actagtggtc ctaaacattt     60
cacggg                                                                66
```

```
<210> SEQ ID NO 14
<211> LENGTH: 66
<212> TYPE: DNA
<213> ORGANISM: Artificial
<220> FEATURE:
<223> OTHER INFORMATION: pSUPER Insert mir205 fwd

<400> SEQUENCE: 14
gatcccctcc ttcattccac cggagtctgt tcaagagaca gactccggtg gaatgaagga      60
ttttta                                                                66

<210> SEQ ID NO 15
<211> LENGTH: 66
<212> TYPE: DNA
<213> ORGANISM: Artificial
<220> FEATURE:
<223> OTHER INFORMATION: pSUPER Insert mir205 rev

<400> SEQUENCE: 15
agcttaaaaa tccttcattc caccggagtc tgtctcttga acagactccg gtggaatgaa      60
ggaggg                                                                66

<210> SEQ ID NO 16
<211> LENGTH: 60
<212> TYPE: DNA
<213> ORGANISM: Artificial
<220> FEATURE:
<223> OTHER INFORMATION: pSUPER Insert mir-scr fwd

<400> SEQUENCE: 16
gatcccccca acaaccgttc tcagaattca agagattctg agaacggttg ttggttttta      60

<210> SEQ ID NO 17
<211> LENGTH: 60
<212> TYPE: DNA
<213> ORGANISM: Artificial
<220> FEATURE:
<223> OTHER INFORMATION: pSUPER Insert mir-scr rev

<400> SEQUENCE: 17
agcttaaaaa ccaacaaccg ttctcagaat ctcttgaatt ctgagaacgg ttgttggggg      60

<210> SEQ ID NO 18
<211> LENGTH: 23
<212> TYPE: DNA
<213> ORGANISM: Artificial
<220> FEATURE:
<223> OTHER INFORMATION: Primer HSV-TK fwd

<400> SEQUENCE: 18
gcgagatcta aatgagtctt cgg                                             23

<210> SEQ ID NO 19
<211> LENGTH: 22
<212> TYPE: DNA
<213> ORGANISM: Artificial
<220> FEATURE:
<223> OTHER INFORMATION: Primer HSV-TK rev

<400> SEQUENCE: 19
attaagcttt taagcgggtc gc                                              22
```

```
<210> SEQ ID NO 20
<211> LENGTH: 24
<212> TYPE: DNA
<213> ORGANISM: Artificial
<220> FEATURE:
<223> OTHER INFORMATION: Primer ARE fwd

<400> SEQUENCE: 20
ataggtacct ccatccaagg aatg                                          24

<210> SEQ ID NO 21
<211> LENGTH: 21
<212> TYPE: DNA
<213> ORGANISM: Artificial
<220> FEATURE:
<223> OTHER INFORMATION: Primer ARE rev

<400> SEQUENCE: 21
atactcgagg cctcagggaa g                                             21

<210> SEQ ID NO 22
<211> LENGTH: 22
<212> TYPE: DNA
<213> ORGANISM: Homo sapiens

<400> SEQUENCE: 22
atgccctttt aacattgcac tg                                            22

<210> SEQ ID NO 23
<211> LENGTH: 22
<212> TYPE: DNA
<213> ORGANISM: homo sapiens

<400> SEQUENCE: 23
ctagtggtcc taaacatttc ac                                            22

<210> SEQ ID NO 24
<211> LENGTH: 22
<212> TYPE: DNA
<213> ORGANISM: Homo sapiens

<400> SEQUENCE: 24
cagactccgg tggaatgaag ga                                            22

<210> SEQ ID NO 25
<211> LENGTH: 20
<212> TYPE: DNA
<213> ORGANISM: artificial
<220> FEATURE:
<223> OTHER INFORMATION: F2RL1 fw

<400> SEQUENCE: 25
gctctccttt gccgaagtgt                                               20

<210> SEQ ID NO 26
<211> LENGTH: 27
<212> TYPE: DNA
<213> ORGANISM: artificial
<220> FEATURE:
<223> OTHER INFORMATION: F2RL1 rev

<400> SEQUENCE: 26
ttgaacttga agagtaagag ctggatt                                       27
```

```
<210> SEQ ID NO 27
<211> LENGTH: 27
<212> TYPE: DNA
<213> ORGANISM: artificial
<220> FEATURE:
<223> OTHER INFORMATION: GTF2H1 fw

<400> SEQUENCE: 27
agcacaaatt tggtaagtca catagaa                                             27

<210> SEQ ID NO 28
<211> LENGTH: 20
<212> TYPE: DNA
<213> ORGANISM: artificial
<220> FEATURE:
<223> OTHER INFORMATION: GTF2H1 rev

<400> SEQUENCE: 28
catggccacc tcacgttttc                                                     20

<210> SEQ ID NO 29
<211> LENGTH: 21
<212> TYPE: DNA
<213> ORGANISM: artificial
<220> FEATURE:
<223> OTHER INFORMATION: HRAS fw

<400> SEQUENCE: 29
gagcagatca acgggtgaa g                                                    21

<210> SEQ ID NO 30
<211> LENGTH: 19
<212> TYPE: DNA
<213> ORGANISM: artificial
<220> FEATURE:
<223> OTHER INFORMATION: HRAS rev

<400> SEQUENCE: 30
ctgagcctgc cgagattcc                                                      19

<210> SEQ ID NO 31
<211> LENGTH: 24
<212> TYPE: DNA
<213> ORGANISM: artificial
<220> FEATURE:
<223> OTHER INFORMATION: KLK2 fw

<400> SEQUENCE: 31
ttcatcacaa atcccatctt tagc                                                24

<210> SEQ ID NO 32
<211> LENGTH: 23
<212> TYPE: DNA
<213> ORGANISM: artificial
<220> FEATURE:
<223> OTHER INFORMATION: KLK2 rev

<400> SEQUENCE: 32
gacatttgat tccttggcat gtt                                                 23

<210> SEQ ID NO 33
<211> LENGTH: 23
<212> TYPE: DNA
<213> ORGANISM: artificial
<220> FEATURE:
<223> OTHER INFORMATION: NCOR2 fw
```

<400> SEQUENCE: 33
aaggaggagc tgatccagaa cat                              23

<210> SEQ ID NO 34
<211> LENGTH: 20
<212> TYPE: DNA
<213> ORGANISM: artificial
<220> FEATURE:
<223> OTHER INFORMATION: NCOR2 rev

<400> SEQUENCE: 34
agccttcttc cggttctcgt                                  20

<210> SEQ ID NO 35
<211> LENGTH: 20
<212> TYPE: DNA
<213> ORGANISM: artificial
<220> FEATURE:
<223> OTHER INFORMATION: PCA3 fw

<400> SEQUENCE: 35
ccgagggaga ccaggaagat                                  20

<210> SEQ ID NO 36
<211> LENGTH: 20
<212> TYPE: DNA
<213> ORGANISM: artificial
<220> FEATURE:
<223> OTHER INFORMATION: PCA3 rev

<400> SEQUENCE: 36
atcgatgacc caagatggcg                                  20

<210> SEQ ID NO 37
<211> LENGTH: 24
<212> TYPE: DNA
<213> ORGANISM: artificial
<220> FEATURE:
<223> OTHER INFORMATION: PSA fw

<400> SEQUENCE: 37
accagaggag ttcttgaccc caaa                             24

<210> SEQ ID NO 38
<211> LENGTH: 20
<212> TYPE: DNA
<213> ORGANISM: artificial
<220> FEATURE:
<223> OTHER INFORMATION: PSA rev

<400> SEQUENCE: 38
ccccagaatc acccgagcag                                  20

<210> SEQ ID NO 39
<211> LENGTH: 19
<212> TYPE: DNA
<213> ORGANISM: artificial
<220> FEATURE:
<223> OTHER INFORMATION: PSAP fw

<400> SEQUENCE: 39
ttggtggaac atgtcaagg                                   19

<210> SEQ ID NO 40
<211> LENGTH: 18
<212> TYPE: DNA
<213> ORGANISM: artificial
<220> FEATURE:
<223> OTHER INFORMATION: PSAP rev

<400> SEQUENCE: 40
cttgggttgc tgatcctg                                          18

<210> SEQ ID NO 41
<211> LENGTH: 22
<212> TYPE: DNA
<213> ORGANISM: artificial
<220> FEATURE:
<223> OTHER INFORMATION: ROCK1 fw

<400> SEQUENCE: 41
tgctgctgtt agcatgttct ca                                     22

<210> SEQ ID NO 42
<211> LENGTH: 23
<212> TYPE: DNA
<213> ORGANISM: artificial
<220> FEATURE:
<223> OTHER INFORMATION: ROCK1 rev

<400> SEQUENCE: 42
ggaaagactg atttgcagtg gat                                    23

<210> SEQ ID NO 43
<211> LENGTH: 20
<212> TYPE: DNA
<213> ORGANISM: artificial
<220> FEATURE:
<223> OTHER INFORMATION: Stx6 fw

<400> SEQUENCE: 43
ctgtgtggca aatgcaggtt                                        20

<210> SEQ ID NO 44
<211> LENGTH: 24
<212> TYPE: DNA
<213> ORGANISM: artificial
<220> FEATURE:
<223> OTHER INFORMATION: Stx6 rev

<400> SEQUENCE: 44
cagagaataa tgggcaagtt acca                                   24

<210> SEQ ID NO 45
<211> LENGTH: 21
<212> TYPE: DNA
<213> ORGANISM: artificial
<220> FEATURE:
<223> OTHER INFORMATION: TMPRSS2 fw

<400> SEQUENCE: 45
gagtgcgact cctcggtacc t                                      21

<210> SEQ ID NO 46
<211> LENGTH: 20
<212> TYPE: DNA
<213> ORGANISM: artificial
<220> FEATURE:
<223> OTHER INFORMATION: TMPRSS2 rev

```
<400> SEQUENCE: 46
agaggcgaac acaccgattc                                              20

<210> SEQ ID NO 47
<211> LENGTH: 18
<212> TYPE: DNA
<213> ORGANISM: artificial
<220> FEATURE:
<223> OTHER INFORMATION: beta actin fw

<400> SEQUENCE: 47
cctggcaccc agcacaat                                                18

<210> SEQ ID NO 48
<211> LENGTH: 20
<212> TYPE: DNA
<213> ORGANISM: artificial
<220> FEATURE:
<223> OTHER INFORMATION: beta actin rev

<400> SEQUENCE: 48
gccgatccac acggagtact                                              20
```

MIRNA COMPOUNDS FOR TREATMENT OF PROSTATE CARCINOMA

REFERENCE TO SEQUENCE LISTING SUBMITTED ELECTRONICALLY

The content of the electronically submitted sequence listing (Name: 32410010001_SequenceListing09_21_12.txt; Size: 9,268 bytes; and Date of Creation: Sep. 21, 2012) filed herewith, is incorporated herein by reference in its entirety.

FIELD OF THE INVENTION

The invention relates inter alia to new pharmaceutical compositions comprising inter alia miRNAs miR-130a, miR-203 and miR-205 and their use for the treatment of cancer, in particular prostate cancer.

BACKGROUND OF THE INVENTION

Micro RNAs (miRNAs) are a class of small regulatory non-coding RNAs (22 nt) that are evolutionary conserved and have been shown to be extensively involved in posttranscriptional regulation of mRNAs [1]. miRNAs bind to partially complementary target sites in the 3'UTR of their target mRNAs which leads either to mRNA degradation or translational repression, depending on the grade of complementary. In animal cells, degradation of partially complementary miRNA targets occurs via deadenylation followed by decapping and subsequent exonucleolytic digestion [2-4]. In human over 600 miRNAs have been identified and it has been estimated that ≈30% of protein coding genes are regulated by miRNAs [5]. miRNAs have crucial functions for basic cellular processes like differentiation or apoptosis, normal cellular development, but also play important roles in the pathogenesis, especially cancer. Several miRNAs have been described to act as oncogenes or tumor suppressors [6-8]. mRNAs have also been shown to participate in pathogenesis and disease progression in cancer. Prostate cancer (PCa) is the most frequently diagnosed malignancy and second leading cause of cancer death in men, with strongly varying rates of tumor progression and responses to treatment [9]. The etiology of PCa is multifactorial, involving environmental and genetic factors [10]. PCa is strongly associated with aging and 2 out of 3 cases are diagnosed in men older than 65 years of age [11]. Treatment of prostate cancer varies depending on the stage of the disease [12]. Early stages of PCa are clinically well manageable. For metastatic forms of prostate cancer the role of androgen deprivation as a firstline therapy has been recognized for more than 60 years [13,14], as initially almost all metastatic prostate cancers require testosterone for growth. Initial response rates to androgen depletion therapy are high, but patients generally progress to a clinically androgen-independent state of the disease within 18-24 months, which results in death within 16 to 18 months. [15-20]. For this metastatic, hormone-refractory ("castration-resistant") form of the disease, no curative therapy exists today.

Therefore, identifying miRNAs that are deregulated in PCa may lead to a better understanding of the etiology of the disease, may deliver markers for diagnosis and prognosis and last but not least may provide novel therapeutic strategies, in particular for fighting the advanced forms of the disease. Several miRNA expression studies in PCa have been published [21-25] showing an overall downregulation of miRNAs in cancer with a more pronounced decrease in more advanced stages, while only two miRNAs have been found to be upregulated in PCa [26-29].

It is thus one object of the present invention to provide novel, mi-RNA-based pharmaceutical compositions for the treatment of prostate cancer.

SUMMARY OF THE INVENTION

As will be demonstrated below, an interrelated group of miRNAs, namely, miR-130a, miR-203 and miR-205 could inter alia be identified which were found to be underexpressed in prostate cancer when compared to normal prostate tissue. It is described herein that the degree of downregulation of all three mi-RNAs, miR-130a, miR-203 and miR-205 may positively correlate with tumor progression. Further, the mRNA encoding for the protein disulfide isomerase A3 (PDIA3) seems to be a novel target of all three mi-RNAs 130a, 203 and 205. PDIA3-expression correlates with the occurrence of prostate cancer and PDIA3 plays a role in the prostate-specific androgen receptor (AR) signaling pathway. Another target may be the mRNa encoding for ATP-dependent DNA helicase 2 subunit, which is also found to be expressed in prostate cancer [41, 42]. In general, important factors of the AR-signaling pathway and the MAPK-signaling pathway seem to be the targets of the miRNAs described herein.

It is thus an object of the present invention to provide a pharmaceutical composition comprising an isolated nucleic acid coding for a miRNA comprising or consisting of SEQ ID No:2 or a derivative or fragment thereof; and/or an optionally modified isolated nucleic acid comprising or consisting of SEQ ID No:2 or a derivative or fragment thereof;

and/or an isolated nucleic acid coding for a miRNA comprising or consisting of SEQ ID No:5 or a derivative or fragment thereof; and/or an optionally modified isolated nucleic acid comprising or consisting of SEQ ID No:5 or a derivative or fragment thereof;

and/or an isolated nucleic acid coding for a miRNA comprising or consisting of SEQ ID No:8 or a derivative or fragment thereof; and/or an optionally modified isolated nucleic acid comprising or consisting of SEQ ID No:8 or a derivative or fragment thereof.

In a preferred embodiment, said pharmaceutical composition comprises an isolated nucleic acid coding for a miRNA comprising or consisting of SEQ ID No:2 or a derivative or fragment thereof; and/or an optionally modified isolated nucleic acid comprising or consisting of SEQ ID No:2 or a derivative or fragment thereof;

and an isolated nucleic acid coding for a miRNA comprising or consisting of SEQ ID No:5 or a derivative or fragment thereof; and/or an optionally modified isolated nucleic acid comprising or consisting of SEQ ID No:5 or a derivative or fragment thereof;

and an isolated nucleic acid coding for a miRNA comprising or consisting of SEQ ID No:8 or a derivative or fragment thereof; and/or an optionally modified isolated nucleic acid comprising or consisting of SEQ ID No:8 or a derivative or fragment thereof.

In a further preferred embodiment, said pharmaceutical composition comprises at least two of the nucleic acids coding for or comprising a specific miRNA such that at least two of the optionally modified miRNAs or fragments or derivatives thereof selected from the group consisting of SEQ ID No:2, SEQ ID No:5 and SEQ ID No:8 are finally present.

In a preferred embodiment, said pharmaceutical composition is for use in the treatment of cancer, particularly prostate cancer.

In an especially preferred embodiment, said pharmaceutical composition is for use in the treatment of hormone-refractory prostate cancer.

In a preferred embodiment, a derivative as mentioned above displays a sequence identity of 70%, preferably of 80%, and most preferably of 90% to the corresponding SEQ ID.

In still another preferred embodiment, a derivative as mentioned above comprises not more than four, preferably three, more preferably two, and most preferably one mismatch(es) to the corresponding SEQ ID.

In a preferred embodiment, a fragment as mentioned above corresponds to a portion of 18, preferably of 20 and most preferably of 21 nucleotides of the corresponding SEQ ID. It may also comprise 19, 17, 16 or 15 nucleotides corresponding to a portion of the corresponding SEQ ID.

In a preferred embodiment, said isolated nucleic acid coding for the corresponding miRNA is a double stranded DNA.

In a preferred embodiment, said double stranded DNA codes for a precursor of the corresponding miRNA, which is then processed to the corresponding miRNA, wherein said precursor preferably comprises a stem-loop structure. If such a stem loop structure is present, it can be preferred that said stem-loop structure comprises 5 to 3500, more preferably 20 to 2000, and most preferably 35 to 120 nucleotides.

It can be preferred that said double stranded DNA codes for a precursor with the SEQ ID No:1 or a fragment or derivative thereof if the miRNA comprises or consists of SEQ ID No:2 or a fragment or derivative thereof; likewise, it can be preferred that said double stranded DNA codes for a precursor with the SEQ ID No:4 or a fragment or derivative thereof if the miRNA comprises or consists of SEQ ID No:5 or a fragment or derivative thereof; likewise, it can be preferred that said double stranded DNA codes for a precursor with the SEQ ID No:7 or a fragment or derivative thereof if the miRNA comprises or consists of SEQ ID No:8 or a fragment or derivative thereof.

In a preferred embodiment, said double stranded DNA comprises the SEQ ID No:3 or a derivative or fragment thereof and the SEQ ID No:22 or a derivative or fragment thereof within the same polynucleotide strand, optionally separated by a spacer, when coding for a miRNA comprising or consisting of SEQ ID No:2 or a derivative or fragment thereof.

In an especially preferred embodiment, said double stranded DNA comprises the SEQ ID No:10 or a fragment or derivative thereof; or SEQ ID No:11 or a fragment or derivative thereof when coding for a miRNA comprising or consisting of SEQ ID No:2 or a fragment or derivative thereof.

In a preferred embodiment, said double stranded DNA comprises the SEQ ID No:6 or a derivative or fragment thereof and the SEQ ID No:23 or a derivative or fragment thereof within the same polynucleotide strand, optionally separated by a spacer, when coding for a miRNA comprising or consisting of SEQ ID No:5 or a derivative or fragment thereof.

In an especially preferred embodiment, said double stranded DNA comprises the SEQ ID No:12 or a fragment or derivative thereof; or SEQ ID No:13 or a fragment or derivative thereof when coding for a miRNA comprising or consisting of SEQ ID No:5 or a fragment or derivative thereof.

In a preferred embodiment, said double stranded DNA comprises the SEQ ID No:9 or a derivative or fragment thereof and the SEQ ID No:24 or a derivative or fragment thereof within the same polynucleotide strand, optionally separated by a spacer, when coding for a miRNA comprising or consisting of SEQ ID No:8 or a derivative or fragment thereof.

In an especially preferred embodiment, said double stranded DNA comprises the SEQ ID No:14 or a fragment or derivative thereof; or SEQ ID No:15 or a fragment or derivative thereof when coding for a miRNA comprising or consisting of SEQ ID No:8 or a fragment or derivative thereof.

In another preferred embodiment referring to a pharmaceutical composition comprising at least two of said isolated nucleic acids coding for a miRNA, said at least two isolated nucleic acids are comprised within a single isolated nucleic acid.

In a preferred embodiment, said optionally modified isolated nucleic acid comprising or consisting of the corresponding SEQ ID or a derivative or a fragment thereof is a single stranded or doubled stranded RNA, preferably of a length of 12 to 80, more preferably of 14 to 60 and most preferably of 18 to 30 nucleotides. Said RNA may also be of a length of 18 to 25, preferably 19 to 24 and most preferably 20 to 22 nucleotides. Said single stranded or double stranded RNA may also be of a length of 15, 16, 17, 18, 19, 20, 21, 22, 23, 24, 25, 26, 27, 28 or 29 nucleotides.

In a preferred embodiment, said double stranded RNA comprises 5' or 3' overhangs, preferably of 3, more preferably of 2 and most preferably of 1 nucleotide.

In a preferred embodiment, said single stranded or double stranded RNA is modified by at least one modification selected from the group consisting of a 2'-O-methyl-ribonucleotide, a phosphorothioate bond, a N3'-P5' phosphoroamidate bond, a peptide-nucleic acid bond, a C-5 thiazole uracil, a C-5 propynyl-cytosine, a phenoxazine-modified cytosine, a 2'-O-propyl ribose and a 2'-methoxyethoxy ribose.

Another object of the present invention relates to a method for detecting, grading and/or prognosing cancer, preferably prostate cancer, and most preferably hormone-refractory prostate cancer, comprising the step of determining in a sample from a subject the expression level(s) of miRNA 130a and/or miRNA 203 and/or miRNA 205.

In a preferred embodiment, said method further comprises the step of comparing said expression level(s) determined in the sample from the subject to the expression level(s) of the respective compound(s) determined in a control.

In a preferred embodiment, said sample from the subject is a body fluid or tissue sample, preferably a prostate tissue sample.

In a preferred embodiment, said body fluid is selected from the group of blood, plasma, urine, saliva, serum, semen, prostate fluid or seminal fluid.

Another object of the present invention relates to a diagnostic kit for detecting, grading and/or prognosing cancer, preferably prostate cancer, and most preferably hormone-refractory prostate cancer, comprising a detecting agent specific for miRNA 130a and/or miRNA 203 and/or miRNA 205.

In a preferred embodiment, said detecting agent is an antibody, an aptamer or an oligonucleotide probe.

Another object of the present invention relates to the use of miRNA 130a and/or miRNA 203 and/or miRNA 205 as marker for cancer, preferably prostate cancer, and most preferably hormone-refractory prostate cancer.

Particularly preferred subject matter of the present invention relates to:

In a preferred embodiment, the present invention provides a pharmaceutical composition comprising
an isolated nucleic acid coding for a miRNA comprising or consisting of SEQ ID No:2 or a derivative or fragment thereof; and/or
an optionally modified isolated nucleic acid comprising or consisting of SEQ ID No:2 or a derivative or fragment thereof;
for use in the treatment of prostate cancer.

In an especially preferred embodiment, said pharmaceutical composition is for use in the treatment of hormone-refractory prostate cancer.

In another preferred embodiment, said pharmaceutical composition additionally comprises
an isolated nucleic acid coding for a miRNA comprising or consisting of SEQ ID No:5 or a derivative or fragment thereof; and/or
an optionally modified isolated nucleic acid comprising or consisting of SEQ ID No:5 or a derivative or fragment thereof;
and/or
an isolated nucleic acid coding for a miRNA comprising or consisting of SEQ ID No:8 or a derivative or fragment thereof; and/or
an optionally modified isolated nucleic acid comprising or consisting of SEQ ID No:8 or a derivative or fragment thereof.

In this case, it can be preferred that said at least two isolated nucleic acids coding for the corresponding miRNAs are comprised within a single isolated nucleic acid.

Another preferred embodiment of the present invention relates to a method for detecting, grading and/or prognosing prostate cancer, preferably hormone-refractory prostate cancer, comprising the step of determining in a sample from a subject the expression level of miRNA 130a, optionally in combination with the expression level(s) of miRNA 203 and/or miRNA 205.

Another preferred embodiment of the present invention relates to a diagnostic kit for detecting, grading and/or prognosing prostate cancer, preferably hormone-refractory prostate cancer, comprising a detecting agent specific for miRNA 130a, optionally in combination with a detecting agents specific for miRNA 203 and/or miRNA 205.

Another preferred embodiment of the present invention relates to the use of miRNA 130a, optionally in combination with miRNA 203 and/or miRNA 205, as marker for prostate cancer, preferably hormone-refractory prostate cancer.

Further particularly preferred subject matter of the present invention relates to:

In another preferred embodiment, the present invention provides a pharmaceutical composition comprising
an isolated nucleic acid coding for a miRNA comprising or consisting of SEQ ID
No:5 or a derivative or fragment thereof; and/or
an optionally modified isolated nucleic acid comprising or consisting of SEQ ID No:5 or a derivative or fragment thereof;
for use in the treatment of hormone-refractory prostate cancer.

In another preferred embodiment, said pharmaceutical composition additionally comprises
an isolated nucleic acid coding for a miRNA comprising or consisting of SEQ ID No:2 or a derivative or fragment thereof; and/or
an optionally modified isolated nucleic acid comprising or consisting of SEQ ID No:2 or a derivative or fragment thereof;
and/or
an isolated nucleic acid coding for a miRNA comprising or consisting of SEQ ID No:8 or a derivative or fragment thereof; and/or
an optionally modified isolated nucleic acid comprising or consisting of SEQ ID No:8 or a derivative or fragment thereof.

In this case, it can be preferred that said at least two isolated nucleic acids coding for the corresponding miRNAs are comprised within a single isolated nucleic acid.

Another preferred embodiment of the present invention relates to a method for detecting, grading and/or prognosing prostate cancer, preferably hormone-refractory prostate cancer, comprising the step of determining in a sample from a subject the expression level of miRNA 203, optionally in combination with the expression level(s) of miRNA 130a and/or miRNA 205.

Another preferred embodiment of the present invention relates to a diagnostic kit for detecting, grading and/or prognosing prostate cancer, preferably hormone-refractory prostate cancer, comprising a detecting agent specific for miRNA 203, optionally in combination with a detecting agent specific for miRNA 130a and/or miRNA 205.

Another preferred embodiment of the present invention relates to the use of miRNA 203, optionally in combination with miRNA 130a and/or miRNA 205 as marker for prostate cancer, more preferably hormone-refractory prostate cancer.

Still further particularly preferred subject matter of the present invention relates to:

As already mentioned above, said pharmaceutical composition comprises in a preferred embodiment at least two of the nucleic acids coding for or comprising a specific miRNA such that at least two of the optionally modified miRNAs or fragments or derivatives thereof selected from the group consisting of SEQ ID No:2, SEQ ID No:5 and SEQ ID No:8 are finally present.

Thus, in a preferred embodiment, said pharmaceutical composition comprises at least two isolated nucleic acids from different subgroups selected from the group of subgroups consisting of
subgroup A: an isolated nucleic acid coding for a miRNA comprising or consisting of SEQ ID No:2 or a derivative or fragment thereof; and/or
an optionally modified isolated nucleic acid comprising or consisting of SEQ ID No:2 or a derivative or fragment thereof;
and
subgroup B: an isolated nucleic acid coding for a miRNA comprising or consisting of SEQ ID No:5 or a derivative or fragment thereof; and/or
an optionally modified isolated nucleic acid comprising or consisting of SEQ ID No:5 or a derivative or fragment thereof;
and
subgroup C: an isolated nucleic acid coding for a miRNA comprising or consisting of SEQ ID No:8 or a derivative or fragment thereof; and/or
an optionally modified isolated nucleic acid comprising or consisting of SEQ ID No:8 or a derivative or fragment thereof.

It can be preferred that the optionally modified miRNAs miR130a (SEQ ID No: 2) and miR 203 (SEQ ID No: 5) or fragments or derivatives thereof are finally present.

It can further be preferred that the optionally modified miRNAs miR130a (SEQ ID No: 2) and miR 205 (SEQ ID No: 8) or fragments or derivatives thereof are finally present. It can also be preferred that the optionally modified miRNAs miR 203 (SEQ ID No: 5) and miR 205 (SEQ ID No: 8) or fragments or derivatives thereof are finally present. It can also be preferred that all three of said optionally modified miR-NAs, namely miRNA 130a (SEQ ID No: 2), miRNA 203 (SEQ ID No: 5) and miRNA 205 (SEQ ID No: 8) are finally present.

In a preferred embodiment, said pharmaceutical composition is for use in the treatment of cancer, preferably prostate cancer and most preferably hormone-refractory prostate cancer.

Another preferred embodiment of the present invention relates to a method for detecting, grading and/or prognosing cancer, preferably prostate cancer, and most preferably hormone-refractory prostate cancer, comprising the step of determining in a sample from a subject the expression level of at least two miRNAs selected from the group consisting of miRNA 130a, miRNA 203 and miRNA 205. It can be preferred to use miRNA 130a and miRNA 203; or miRNA 130a and miRNA 205; or miRNA 203 and miRNA 205; or all three miRNAs, i.e. miRNA 130a, miRNA 203 and miRNA 205.

Another preferred embodiment of the present invention relates to a diagnostic kit for detecting, grading and/or prognosing cancer, preferably prostate cancer, and most preferably hormone-refractory prostate cancer, comprising a detecting agent specific for at least two miRNAs selected from the group consisting of miRNA 130a, miRNA 203 and miRNA 205. It can be preferred to use miRNA 130a and miRNA 203; or miRNA 130a and miRNA 205; or miRNA 203 and miRNA 205; or all three miRNAs, i.e. miRNA 130a, miRNA 203 and miRNA 205.

Another preferred embodiment of the present invention relates to the use of at least two miRNAs selected from the group consisting of miRNA 130a, miRNA 203 and miRNA 205 as marker for cancer, preferably prostate cancer, and more preferably hormone-refractory prostate cancer. It can be preferred to use miRNA 130a and miRNA 203; or miRNA 130a and miRNA 205; or miRNA 203 and miRNA 205; or all three miRNAs, i.e. miRNA 130a, miRNA 203 and miRNA 205.

Further objects and embodiments of the invention are mentioned in the following.

It is also an object of the present invention to provide a pharmaceutical composition comprising
  a first recombinant nucleic acid molecule, comprising at least a first sequence corresponding to SEQ ID No:3 and at least a second sequence corresponding to the reverse complement of said first sequence wherein said recombinant nucleic acid molecule is capable of expressing said first and second sequence such that a molecule according to SEQ ID No:2 is produced in a mammalian cell, and/or
  a second recombinant nucleic acid molecule, comprising at least a first sequence corresponding to SEQ ID No:6 and at least a second sequence corresponding to the reverse complement of said first sequence wherein said recombinant nucleic acid molecule is capable of expressing said first and second sequence such that a molecule according to SEQ ID No:5 is produced in a mammalian cell, and/or
  a third recombinant nucleic acid molecule, comprising at least a first sequence corresponding to SEQ ID No:9 and at least a second sequence corresponding to the reverse complement of said first sequence wherein said recombinant nucleic acid molecule is capable of expressing said first and second sequence such that a molecule according to SEQ ID No:8 is produced in a mammalian cell.

A preferred embodiment relates to a pharmaceutical composition, wherein the composition comprises said first, second and third recombinant nucleic acid molecules.

It is another object of the invention to provide a pharmaceutical composition comprising a recombinant nucleic acid molecule, wherein the recombinant nucleic acid molecule comprises
  a first segment, comprising at least a first sequence corresponding to SEQ ID No:3 and at least a second sequence corresponding to the reverse complement of said first sequence wherein said recombinant nucleic acid molecule is capable of expressing said first and second sequence(s) such that a molecule according to SEQ ID No:2 is produced in a mammalian cell, and/or
  a second segment, comprising at least a first sequence corresponding to SEQ ID No:6 and at least a second sequence corresponding to the reverse complement of said first sequence wherein said recombinant nucleic acid molecule is capable of expressing said first and second sequence(s) such that a molecule according to SEQ ID No:5 is produced in a mammalian cell, and/or
  a third segment, comprising at least a first sequence corresponding to SEQ ID No:9 and at least a second sequence corresponding to the reverse complement of said first sequence wherein said recombinant nucleic acid molecule is capable of expressing said first and second sequence(s) such that a molecule according to SEQ ID No:8 is produced in a mammalian cell.

A preferred embodiment relates to a pharmaceutical composition comprising a recombinant nucleic acid molecule, wherein the recombinant nucleic acid molecule comprises said first, second and third segments.

Other preferred embodiments relate to the abovementioned pharmaceutical compositions, wherein said first and said second nucleic acid sequences are comprised in stem-loop forming nucleic acids, wherein the stem-loop forming nucleic acids are selected from the group consisting of SEQ ID No:1, SEQ ID No:4, SEQ ID No:7, SEQ ID No:10, SEQ ID No:12 and SEQ ID No:14.

Yet other preferred embodiments of the invention relate to pharmaceutical compositions wherein the above mentioned recombinant nucleic acid molecule is a vector comprising:
  a promoter being functional in mammalian cells,
  operatively linked thereto said first sequence encoding for a nucleic acid molecule that is reverse complementary and/or identical to a nucleic acid selected from the group consisting of SEQ ID No:3, SEQ ID No:6 and SEQ ID No:9, optionally a spacer nucleic acid sequence and a second nucleic acid sequence being reverse complementary to said first sequence, and
  a termination sequence.

It is another object of the present invention to provide a pharmaceutical composition comprising at least one nucleic acid molecule, wherein the at least one nucleic acid molecule comprises a nucleic acid selected from the group consisting of SEQ ID No:2, SEQ ID No:5 and SEQ ID No:8 or a nucleic acid molecule that is reverse complementary thereto.

A preferred embodiment thereof relates to a pharmaceutical composition wherein the at least one nucleic acid molecule comprises at least one oligonucleotide and/or at least one modified oligonucleotide.

Another preferred embodiment thereof relates to a pharmaceutical composition, wherein the at least one nucleic acid molecule comprises three oligonucleotides selected from the group consisting of SEQ ID No:2, SEQ ID No:5 and SEQ ID No:8.

An even more preferred embodiment thereof relates to a pharmaceutical composition, wherein the at least one oligonucleotide comprises or consists of 22 linked nucleotides.

A most preferred embodiment thereof relates to a pharmaceutical composition, wherein the at least one oligonucleotide is a double stranded oligonucleotide.

Especially preferred embodiments of the aspects of the invention relate to the above mentioned pharmaceutical compositions for the treatment of a neoplastic condition, preferably cancer and most preferably prostate cancer.

DETAILED DESCRIPTION OF THE INVENTION

Depending on the stage of the disease, treatments for prostate carcinoma range from surveillance to radical local treatment, to androgen deprivation therapy. Radical prostatectomy and radiation therapy are curative intended treatments for localised prostate cancer.

The aims of these procedures are primarily to ensure oncological control. Approximately 20-30% patients undergoing local treatment will sooner or later relapse and be in need of further therapy. Endocrine therapy of prostate cancer has mostly been reserved to patients with advanced stages of the disease. The principle for endocrine treatment of prostate cancer is elimination of stimulatory effects of testicular androgens on the prostate tumour cells. Since non-steroidal anti-androgens have fewer side-effects than castrational therapies, there is an increased interest for using endocrine treatment as an adjuvant therapy after localised treatment. At least in certain stages of the disease, early hormonal treatment may have survival benefits. Androgen deprivation reduces clinical symptoms in about 70-80% of patients with advanced prostate cancer, but most tumours relapse within two years to an androgen-independent state. For this metastatic, hormone-refractory form of the disease, no curative therapy exists today. It is in this stage of the disease that patients die of prostate cancer.

MicroRNAs (miRNAs) are small non-coding RNAs that regulate expression of their targets either by translational repression, mRNA deadenylation or direct cleavage. miR-NAs have crucial functions for basic cellular processes like differentiation or apoptosis, normal cellular development, but also play important roles in the pathogenesis, especially cancer. Several miRNAs have been described to act as oncogenes or tumor suppressors [6-8]. mRNAs have also been shown to participate in pathogenesis and disease progression in cancer.

Therefore, identifying miRNAs that are deregulated in PCa may lead to novel therapeutic strategies, in particular for fighting the advanced forms of the disease.

Figure 1A:
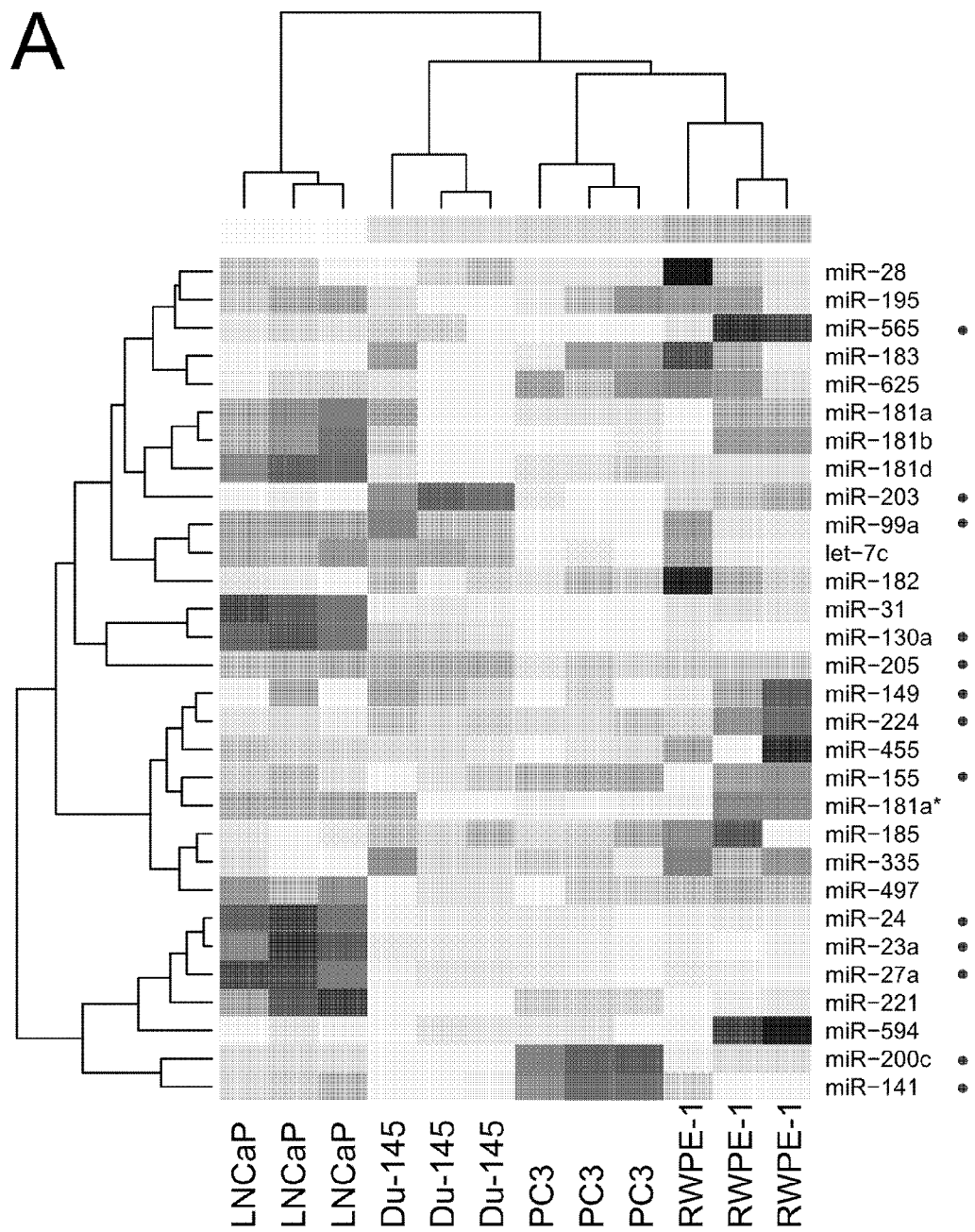
FIG. 1. MiRNA expression in PCa cell lines and clinical samples. (A) MiRNAs were isolated from PCa cell lines LNCaP, PC-3, and Du-145, and the non-malignant prostate epithelial cell line RWPE-1. Normalized expression, detected using Combimatrix 4×2k human miRNA microarrays, is shown for miRNAs that were found to be differentially expressed between the PCa and the non-malignant cells at an FDR<$10^{-6}$. Hierarchical clustering is based on miRNA expression. Red and blue indicate low and high expression, respectively. Red dots highlight miRNAs that were tested by RT-qPCR. (B) Expression of miR-130a, miR-203, and miR-205 detected by RT-qPCR in total RNA from RWPE-1, LNCaP, PC-3 and Du-145 cells respectively, using miRNA specific TaqMan assays. Expression was normalized to U48 snoRNA. (C) Analogous quantification of the miRNAs in total RNA isolated from PCa tumors of different progression stages, low Gleason grade (L), high Gleason grade (H), and recurrent (R) samples, and from non-malignant tissue (N).
Figures 1B, 1C:
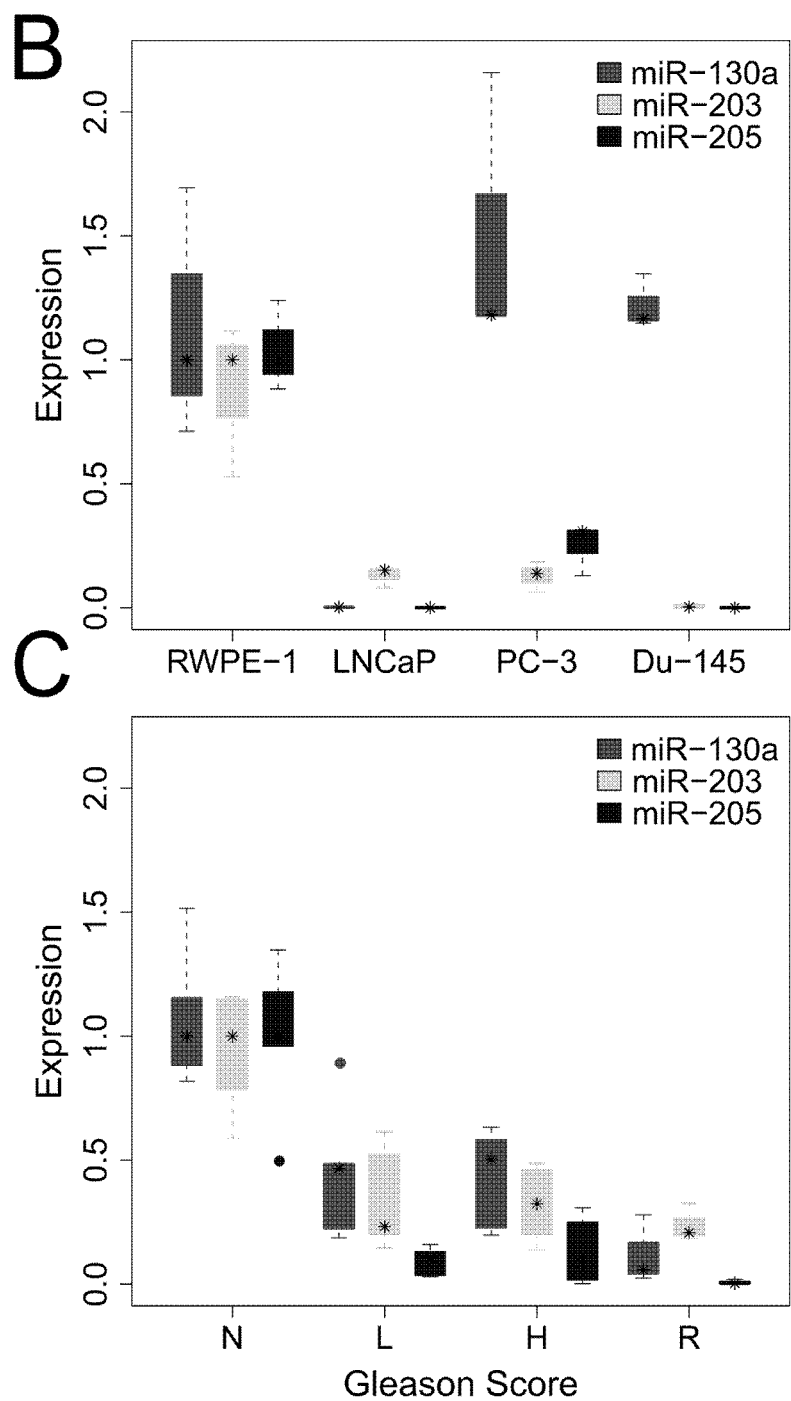

In their quest to identify new mi-RNAs with therapeutic potential for the treatment of prostate cancer the inventors inter alia identified mi-RNAs miR-130a, miR-203, and miR-205 to be downregulated in clinical samples of prostate cancer (PCa) compared to healthy tissue. The inventors thus identified a group of underexpressed miRNAs, namely, miR-130a, miR-203 and miR-205. Intriguingly, the inventors found that the degree of downregulation of all three mi-RNAs, miR-130a, miR-203 and miR-205, seems to positively correlate with clinical tumor progression: A clear trend for all three mi-RNAs could be demonstrated, wherein the expression of miR-130a, miR-203 and miR-205 seems to progressively decrease in patient samples of prostate cancer dependent on the progression stages (FIG. 1C).

Further, the mRNA encoding for the protein disulfide isomerase A3 (PDIA3) seems to be a novel target of all three mi-RNAs 130a, 203 and 205. PDIA3-expression correlates with the occurrence of prostate cancer and PDIA3 plays a role in the prostate-specific androgen receptor (AR) signaling pathway. Another target may be the mRNA encoding for ATP-dependent DNA helicase 2 subunit, which is also found to be expressed in prostate cancer [41, 42]. In addition to a potential role of the miRNAs in AR-signaling, the inventor's data also points to a role in MAPK-signaling.

Consequently, a direct role for mi-RNAs 130a, 203 and/or 205 in AR-signaling (inter alia the repression of the potential oncogenes PDIA3 and ATP-dependent DNA helicase 2 subunit) and MAPK-signaling, and thus in the principal etiology of prostate cancer and especially in the transition to hormone-refractory phenotypes, malignant transformation and metastases seems to be one of the conclusions of the findings of the inventors.

Figure 4A:
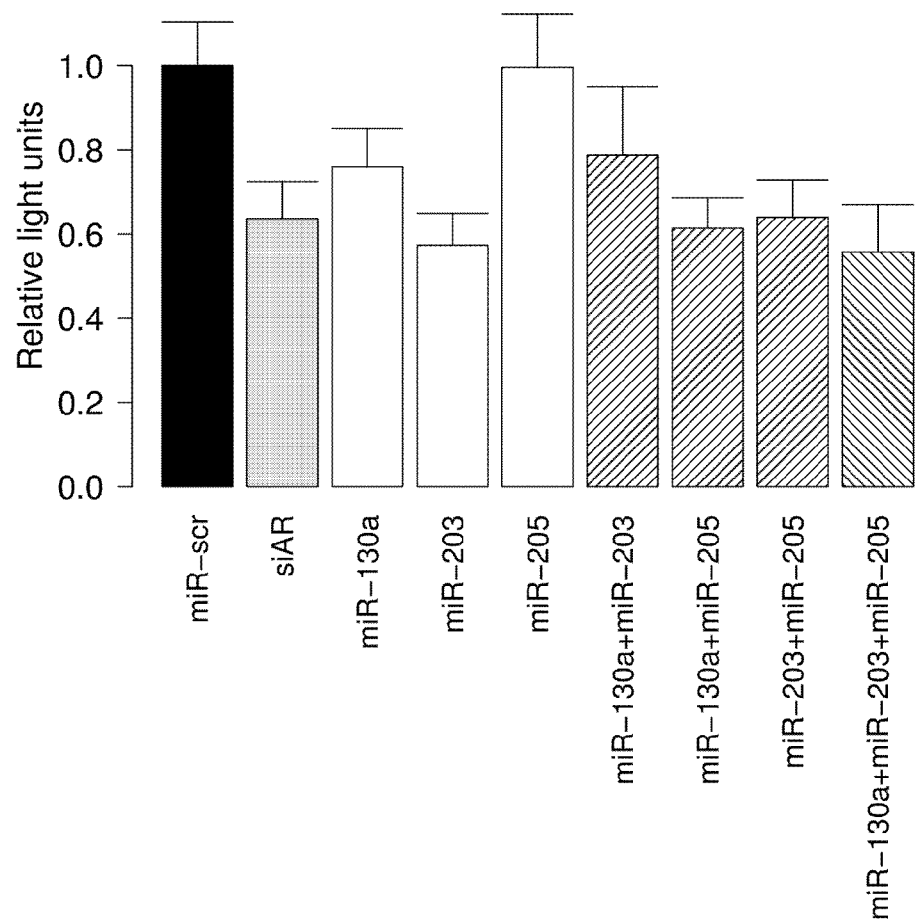
FIG. 4. MiR-130a, miR-203, and miR-205 synergistically suppress AR signaling. (A) Luciferase reporter assays were performed in LNCaP cells 48 h post transfection with the miRNAs or miR-scr and a reporter plasmid containing a luciferase gene under control of an androgen responsive element. Transfection with an siRNA targeting the AR (siAR) was used as a positive control (n=3, data represent mean+Stdv). (B) Western Blot for AR and Actin (endogenous control).

Importantly, reconstitution of 130a, 203 and/or 205 in the LNCaP PCa cell line resulted in marked morphology change, growth arrest, and apoptosis. The inventors therefore propose that miR-130a, miR-203, and/or miR-205 act as tumor suppressor genes in prostate cancer by inter alia targeting androgen receptor transactivating proteins and negatively regulating cell survival. Importantly, using an AR-responsive element (ARE) reporter assay, the inventors further demonstrate inhibition of AR signaling activity by expression of miRNAs 130a, 203 and/or 205 (FIG. 4). From the above it is also clear, that mi-RNAs 130a, 203 and/or 205 also seem to be diagnostic markers, in particular, for later stages of prostate cancer, i.e. hormone refractory stages, metastasis and recurrent tumors. In analogy to the approach described by Kota and colleagues (Cell. 2009 Jun. 12; 137(6):1005-17) the inventors thus propose to use miR-130a, miR-203, and/or miR-205 or combinations thereof to treat PCa, in particular metatstatic and recurrent PCa.

The skilled person is aware of the fact that miRNA are noncoding RNAs of about 19 to about 24 nucleotides which regulate expression of a polynucleotide comprising the target sequence (here for example PDIA3 or ATP-dependent DNA helicase 2 subunit) and that miRNA molecules are processed from longer precursor transcripts that have the ability to form stable hairpin structures. They are processed from longer precursor transcripts that range in size from approximately 70 to 2000 nt or longer, and these precursor transcripts have the ability to form stable hairpin structures. In animals, the enzyme involved in processing miRNA precursors is called Dicer, an RNAse Ill-like protein. Furthermore, it is becoming clear from recent work that at least some miRNA hairpin precursors originate as longer polyadenylated transcripts, and several different miRNAs and associated hairpins can be present in a single transcript. Recent work has also examined the selection of the miRNA strand from the dsRNA product arising from processing of the hairpin by DICER (Schwartz et al., 2003, Cell 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

It follows that from the mature, typically 19 to about 24 nucleotides long double stranded mi-RNA molecule, a "mature" single stranded miRNA molecule is released which hybridizes, typically with the untranslated distal sequence of a protein coding mRNA, or the 3' UTR and leads to degradation of the respective mRNA or inhibits its translation into a polypeptide.

As mentioned above, it is an object of the present invention to provide a pharmaceutical composition comprising an isolated nucleic acid coding for a miRNA comprising or consisting of SEQ ID No:2 or a derivative or fragment thereof; and/or an optionally modified isolated nucleic acid comprising or consisting of SEQ ID No:2 or a derivative or fragment thereof;

and/or an isolated nucleic acid coding for a miRNA comprising or consisting of SEQ ID No:5 or a derivative or fragment thereof; and/or an optionally modified isolated nucleic acid comprising or consisting of SEQ ID No:5 or a derivative or fragment thereof;

and/or an isolated nucleic acid coding for a miRNA comprising or consisting of SEQ ID No:8 or a derivative or fragment thereof; and/or an optionally modified isolated nucleic acid comprising or consisting of SEQ ID No:8 or a derivative or fragment thereof.

One of the objects of the present invention thus resides in the provision of a pharmaceutical composition comprising at least one or combinations of the optionally modified miRNAs 130a, 203 and 205 or fragments or derivatives thereof (see embodiments above), which are each capable of restoring the function of the corresponding endogenous miRNA.

In the following, it will be explained in more detail how this object can inter alia be achieved. If deemed appropriate, the definitions for specific terms as used herein will be included into the following section as well.

As used herein, the term "nucleic acid" is interchangeable with the term "polynucleotide".

The term "coding for" is used herein in the meaning as common in the field. To exemplify this, a specific nucleic acid sequence in direction 5' to 3' on the "coding" strand of a double stranded DNA may be located downstream of a promoter region. Upon assembly of the necessary protein complex including RNA polymerase on the promoter, the RNA polymerase will "recognize and read" the "coding sequence" and produce a corresponding RNA molecule of a specific sequence (the process of "transcription"). Thus, if the final product is e.g. an RNA, such as a miRNA, said specific DNA nucleic acid sequence is said to "code for" said corresponding specific RNA. If the final product is a protein, the DNA codes for a specific mRNA, which then in turn codes for a specific amino acid sequence. After production of the amino acid chain from the mRNA (the process of "translation"), the polypeptide is ultimatively folded into its final conformation. Preferably, the term "coding for" is used herein in connection with RNAs.

As used herein the term "derivative" refers to a polynucleotide sequence that may differ from the polynucleotide sequence it refers to in that one or more nucleotides of the original sequence are substituted by other nucleotides and/or (chemically) modified by methods known to the skilled person, provided that the polynucleotide is still capable of fulfilling its respective function.

A "derivative" may comprise between 0 and 4, i.e. 0, 1, 2, 3 or 4 nucleotide substitutions, deletions or insertions, provided that the polynucleotide is still capable of fulfilling its respective function.

A "derivative" may show at least 50%, preferably at least 60%, preferably at least 70%, preferably at least 75%, at least 76%, at least 77% at least 78% at least 79%, more preferably at least 80%, at least 81%, at least 82%, at least 83%, at least 84%, at least 85%, at least 86%, at least 87%, at least 88% at least 89%, more preferably at least 90%, even more preferably at least 91%, at least 92%, at least 93%, at least 94% least 95%, at least 96%, at least 97% or at least 98% and most preferably at least 99% sequence identity to the polynucleotide sequence it refers to.

As used herein, the term "fragment" generally refers to a polynucleotide of between 10 and 21 nucleotides in length. A fragment may e.g. be 10, 11, 12, 13, 14, 15, 16, 17, 18, 19, 20 or 21 nucleotides in length. A fragment is typically a portion of the polynucleotide it refers to.

The term "modified" as used herein inter alia includes polynucleotides having linkages between nucleotides that differ from typical linkages. Examples of such polynucleotides specifically include 2'-O-methyl-ribonucleotide, a polynucleotide derivative in which a phosphodiester bond in a polynucleotide is converted to a phosphorothioate bond, a polynucleotides derivative in which a phosphodiester bond in a polynucleotide is converted to a N3'-P5' phosphoroamidate bond, a polynucleotide derivative in which a ribose and a phosphodiester bond are converted to a peptide-nucleic acid bond, a polynucleotide derivative in which uracil is substituted with C-5 propynyl uracil, a polynucleotide derivative in which uracil is substituted with C-5 thiazole uracil, a polynucleotide derivative in which cytosine is substituted with C-5 propynyl-cytosine, a polynucleotide derivative in which cytosine is substituted with phenoxazine-modified cytosine, a polynucleotide derivative in which ribose is substituted with 2'-O-propyl ribose, and a polynucleotide derivative in which ribose is substituted with 2'-methoxyethoxy ribose.

One possibility among others to provide a given mi-RNA molecule in a mammalian cell is to introduce into this cell a recombinant nucleic acid molecule coding for or comprising a nucleic acid that will form the above mentioned precursor hairpin-structure, that will serve as a Dicer-substrate, allowing for the production of the "mature" miRNA molecule.

The isolated nucleic acid according to the invention may be a double stranded or single stranded RNA or DNA molecule.

An isolated nucleic acid coding for a miRNA or a derivative or a fragment thereof according to the present invention may be DNA. Thus, the expression may e.g. be achieved by using an expression vector, which includes a polynucleotide sequence that encodes said miRNA.

In a preferred embodiment the expression vector expresses an RNA that forms a hairpin with a loop. In this regard, it can be preferred that the precursor of the corresponding miRNA is expressed; thus, a sequence corresponding to SEQ ID No:1 or a fragment or derivative thereof; SEQ ID No:4 or a fragment or derivative thereof; or SEQ ID No:7 or a fragment or derivative thereof can inter alia be expressed.

The skilled person knows that DNA and RNA contain different bases, that is, DNA is composed of the four bases adenosine, thymine, cytosine and guanine, while in RNA-molecules the base thymine is replaced by the base uracil.

The same applies, mutatis mutandis, for all RNA sequences forming part of the present invention, that is, in order to obtain an uracil-residue in any given RNA sequence, a thymidine-residue has to be used in the corresponding DNA-sequence.

Thus, the skilled person is fully aware, that for the expression and/or production of the following miRNA (Mature miRNA 130a, SEQ ID No:2) CAGUGCAAUG-UUAAAAGGGCAU, the corresponding DNA sequence (SEQ ID No:3) CAGTGCAATGTTAAAAGGGCAT and/or a sequence reverse complementary thereto ATGCCCTTT-TAACATTGCACTG (SEQ ID No:22) can be used.

The same applies for GUGAAAUGUUUAGGACCAC-UAG (Mature miRNA 203, SEQ ID No: 5) and the corresponding DNA-sequence GTGAAATGTTTAGGACCAC-TAG (SEQ ID No:6) and/or a sequence reverse complementary thereto CTAGTGGTCCTAAACATTTCAC (SEQ ID No:23), as well as UCCUUCAUUCCACCG-GAGUCUG (Mature miRNA 205, SEQ ID No: 8) and the corresponding DNA-sequenceTCCTTCATTCCACCG-GAGTCTG (SEQ ID No:9) and/or a sequence reverse complementary thereto CAGACTCCGGTGGAAT-GAAGGA (SEQ ID No:24).

Preferred isolated nucleic acids coding for a miRNA comprising or consisting of SEQ ID No:2 are polynucleotides comprising
  (a) a first polynucleotide sequence comprising SEQ ID No:3 or a fragment or derivative thereof and a second polynucleotide sequence comprising SEQ ID No: 22 or a fragment or derivative thereof.

Preferred isolated nucleic acids coding for a miRNA comprising or consisting of SEQ ID No:5 are polynucleotides comprising
  (b) a first polynucleotide sequence comprising SEQ ID No:6 or a fragment or derivative thereof and a second polynucleotide sequence comprising SEQ ID No: 23 or a fragment or derivative thereof.

Preferred isolated nucleic acids coding for a miRNA comprising or consisting of SEQ ID No:8 are polynucleotides comprising (c) a first polynucleotide sequence comprising SEQ ID No:9 or a fragment or derivative thereof and a second polynucleotide sequence comprising SEQ ID No: 24 or a fragment or derivative thereof.

In a preferred embodiment the polynucleotide according to (a), (b) or (c) is double stranded DNA.

In a preferred embodiment the aforementioned isolated polynucleotide according to (a), (b) or (c) is integrated into an expression vector that directs intracellular synthesis of said miRNA molecule.

In a preferred embodiment, the first polynucleotide sequence is located upstream of the second polynucleotide sequence within the same polynucleotide strand, i.e. SEQ ID No:3 or a fragment or derivative thereof is located upstream of SEQ ID No:22 or a fragment or derivative thereof; or SEQ ID No:6 or a fragment or derivative thereof is located upstream of SEQ ID No:23 or a fragment or derivative thereof; or SEQ ID No:9 or a fragment or derivative thereof is located upstream of SEQ ID No:24 or a fragment or derivative thereof.

In another preferred embodiment a "spacer" or "linker" polynucleotide is located downstream of the first polynucleotide sequence and upstream of the second polynucleotide sequence, i.e. a linker polynucleotide is located downstream of SEQ ID No:3 or a fragment or derivative thereof and upstream of SEQ ID No:22 or a fragment or derivative thereof; or downstream of SEQ ID No:6 or a fragment or derivative thereof and upstream of SEQ ID No:23 or a fragment or derivative thereof; or downstream of SEQ ID No:9 or a fragment or derivative thereof and upstream of SEQ ID No:24 or a fragment or derivative thereof.

In some other embodiments, the second polynucleotide sequence is located upstream of the first polynucleotide sequence within the same polynucleotide strand, i.e. SEQ ID No:22 or a fragment or derivative thereof is located upstream of SEQ ID No:3 or a fragment or derivative thereof; or SEQ ID No:23 or a fragment or derivative thereof is located upstream of SEQ ID No:6 or a fragment or derivative thereof; or SEQ ID No:24 or a fragment or derivative thereof is located upstream of SEQ ID No:9 or a fragment or derivative thereof.

In such embodiments, if a spacer is present, it is preferred that the spacer is located downstream of the second polynucleotide sequence and upstream of the first polynucleotide sequence, i.e. a linker is located downstream of SEQ ID No:22 or a fragment or derivative thereof and upstream of SEQ ID No:3 or a fragment or derivative thereof; or downstream of SEQ ID No:23 or a fragment or derivative thereof and upstream of SEQ ID No:6 or a fragment or derivative thereof; or downstream of SEQ ID No:24 or a fragment or derivative thereof and upstream of SEQ ID No:9 or a fragment or derivative thereof.

Preferably the first and/or second polynucleotide sequence has a length of between 10 and 100, between 12 and 80, between 14 and 60, between 16 and 50, between 17 and 40, between 18 and 30 nucleotides, more preferably between 18 and 26 nucleotides. In a particularly preferred embodiment the first and second polynucleotide consist of a sequence according to SEQ ID No: 3 and SEQ ID No: 22; SEQ ID No:6 and SEQ ID No:23; and SEQ ID No:9 and SEQ ID No:24, respectively.

The terms "upstream" and "downstream" are used herein according to their conventional and well known meaning in the art.

The term "spacer", "spacer polynucleotide" or "linker polynucleotide" as used herein refers to a polynucleotide sequence that acts as a molecular bridge to operably link two different polynucleotides sequences, wherein one portion of the linker is operably linked to a first polynucleotide sequence, and wherein another portion of the linker is operably linked to a second polynucleotides sequence.

In a preferred embodiment the spacer polynucleotide is a DNA sequence. The length of the spacer polynucleotide can vary. The spacer can be several thousand nucleotides in length. Thus, the spacer can e.g. comprise between 5 to 3500 nucleotides. The spacer is preferably 5 to 20 nucleotides in length.

The aforementioned isolated polynucleotide according to (a), (b) or (c) can be single stranded or double stranded. In a preferred embodiment the isolated polynucleotide according to (a), (b) or (c) is double stranded.

It can be preferred that, if at least two coding nucleic acids are used, said at least two nucleic acids are comprised within a single isolated nucleic acid.

In the following, this is exemplary shown for a single isolated nucleic acid molecule comprising the forward and the reverse complementary sequences of the corresponding miRNAs or fragments or derivatives thereof.

Thus, in such recombinant nucleic acid molecules different nucleic acid sequences and such sequences being "reverse complement" thereto may be employed to allow for the production not only of miRNA molecules but also of the corresponding siRNAs, shRNAs, antisense RNAs and the like. The skilled person is aware of the fact that the position of the so-called "sense" (5'-3') and the reverse complement sequence (complementary and 3'-5') can be exchanged. This clearly is also true for the abovementioned recombinant nucleic acid molecules comprising segments, which segments, for example, can have the following configurations:

| miRNA #1 | miRNA#2 | miRNA#3 | (revers #1 | revers #2 | revers #3) |
|---|---|---|---|---|---|
| 5'-3' | 5'-3' | 5'-3' | (3'-5' | 3'-5' | 3'-5') |
| 5'-3' | 5'-3' | 3'-5' | (3'-5' | 3'-5' | 5'-3') |
| 5'-3' | 3'-5' | 5'-3' | (3'-5' | 5'-3' | 3'-5') |
| 5'-3' | 3'-5' | 3'-5' | (3'-5' | 5'-3' | 5'-3') |
| 3'-5' | 5'-3' | 5'-3' | (5'-3' | 3'-5' | 3'-5') |
| 3'-5' | 5'-3' | 3'-5' | (5'-3' | 3'-5' | 5'-3') |
| 3'-5' | 3'-5' | 5'-3' | (5'-3' | 5'-3' | 3'-5') |
| 3'-5' | 3'-5' | 3'-5' | (5'-3' | 5'-3' | 5'-3') |

The same, naturally, applies to the above mentioned nucleic acid segments whose order can also be varied, as for example shown below:

| miRNA#2 | miRNA#1 | miRNA#3 |
|---|---|---| and so on.

Clearly, the same applies to the above mentioned shRNA, siRNA, and antisense RNA molecules.

Such recombinant nucleic acids comprising several of said sequences are of course preferably comprised in vectors or the like as outlined further below.

Further embodiments (A) relating to the above mentioned nucleic acids are referred to in the following.

Thus, an embodiment of the present invention refers to a pharmaceutical composition comprising
   a first recombinant nucleic acid molecule, comprising at least a first sequence corresponding to SEQ ID No:3 and at least a second sequence corresponding to the reverse complement of said first sequence wherein said recombinant nucleic acid molecule is capable of expressing said first and second sequence such that a molecule according to SEQ ID No:2 is produced in a mammalian cell, and/or a second recombinant nucleic acid molecule, comprising at least a first sequence corresponding to SEQ ID No:6 and at least a second sequence corresponding to the reverse complement of said first sequence wherein said recombinant nucleic acid molecule is capable of expressing said first and second sequence such that a molecule according to SEQ ID No:5 is produced in a mammalian cell, and/or a third recombinant nucleic acid molecule, comprising at least a first sequence corresponding to SEQ ID No:9 and at least a second sequence corresponding to the reverse complement of said first sequence wherein said recombinant nucleic acid molecule is capable of expressing said first and second sequence such that a molecule according to SEQ ID No:8 is produced in a mammalian cell.

A preferred embodiment of the invention relates to a pharmaceutical composition, wherein the composition comprises said first, second and third recombinant nucleic acid molecules.

Another preferred embodiment of the invention relates to a pharmaceutical composition, wherein the composition comprises said first and second recombinant nucleic acid molecules or said first and third recombinant nucleic acid molecules or said second and third recombinant nucleic acid molecules.

Another preferred embodiment relates to a pharmaceutical composition comprising said first recombinant nucleic acid molecule or said second recombinant nucleic acid molecule or said third recombinant nucleic acid molecule.

Another preferred embodiment of the invention relates to a pharmaceutical composition comprising
- a first recombinant nucleic acid molecule, comprising at least a first sequence corresponding to SEQ ID No:10 wherein said recombinant nucleic acid molecule is capable of expressing said first sequence such that a molecule according to SEQ ID No:2 is produced in a mammalian cell, and/or
- a second recombinant nucleic acid molecule, comprising at least a first sequence corresponding to SEQ ID No:12 wherein said recombinant nucleic acid molecule is capable of expressing said first sequence such that a molecule according to SEQ ID No:5 is produced in a mammalian cell, and/or
- a third recombinant nucleic acid molecule, comprising at least a first sequence corresponding to SEQ ID No:14 wherein said recombinant nucleic acid molecule is capable of expressing said first sequence such that a molecule according to SEQ ID No:8 is produced in a mammalian cell.

A preferred embodiment of the invention relates to a pharmaceutical composition, wherein the composition comprises said first, second and third recombinant nucleic acid molecules.

Another preferred embodiment of the invention relates to a pharmaceutical composition, wherein the composition comprises said first and second recombinant nucleic acid molecules or said first and third recombinant nucleic acid molecules or said second and third recombinant nucleic acid molecules.

Another preferred embodiment relates to a pharmaceutical composition comprising said first recombinant nucleic acid molecule or said second recombinant nucleic acid molecule or said third recombinant nucleic acid molecule.

Another preferred embodiment of the invention relates to a pharmaceutical composition comprising
- a first recombinant nucleic acid molecule, comprising at least a first sequence corresponding to SEQ ID No:1 wherein said recombinant nucleic acid molecule is capable of expressing said first sequence such that a molecule according to SEQ ID No:2 is produced in a mammalian cell, and/or
- a second recombinant nucleic acid molecule, comprising at least a first sequence corresponding to SEQ ID No:4 wherein said recombinant nucleic acid molecule is capable of expressing said first sequence such that a molecule according to SEQ ID No:5 is produced in a mammalian cell, and/or
- a third recombinant nucleic acid molecule, comprising at least a first sequence corresponding to SEQ ID No:7 wherein said recombinant nucleic acid molecule is capable of expressing said first sequence such that a molecule according to SEQ ID No:8 is produced in a mammalian cell.

A preferred embodiment of the invention relates to a pharmaceutical composition, wherein the composition comprises said first, second and third recombinant nucleic acid molecules.

Another preferred embodiment of the invention relates to a pharmaceutical composition, wherein the composition comprises said first and second recombinant nucleic acid molecules or said second and third recombinant nucleic acid molecules or said first and third recombinant nucleic acid molecules.

Another preferred embodiment relates to a pharmaceutical composition comprising said first recombinant nucleic acid molecule or said second recombinant nucleic acid molecule or said third recombinant nucleic acid molecule.

Of course the skilled person is aware of the fact, that the different above mentioned first and second sequence(s) can be comprised in a single recombinant nucleic acid molecule.

Thus, another embodiment of the present invention relates to a pharmaceutical composition, comprising a recombinant nucleic acid molecule, wherein the recombinant nucleic acid molecule comprises
- a first segment, comprising at least a first sequence corresponding to SEQ ID No:3 and at least a second sequence corresponding to the reverse complement of said first sequence wherein said recombinant nucleic acid molecule is capable of expressing said first and second sequence(s) such that a molecule according to SEQ ID No:2 is produced in a mammalian cell, and/or
- a second segment, comprising at least a first sequence corresponding to SEQ ID No:6 and at least a second sequence corresponding to the reverse complement of said first sequence wherein said recombinant nucleic acid molecule is capable of expressing said first and second sequence(s) such that a molecule according to SEQ ID No:5 is produced in a mammalian cell, and/or
- a third segment, comprising at least a first sequence corresponding to SEQ ID No:9 and at least a second sequence corresponding to the reverse complement of said first sequence wherein said recombinant nucleic acid molecule is capable of expressing said first and second sequence(s) such that a molecule according to SEQ ID No:8 is produced in a mammalian cell In a preferred embodiment the pharmaceutical composition comprises a recombinant nucleic acid molecule comprising said first, second and third segments.

Another embodiment of the present invention relates to a pharmaceutical composition comprising a recombinant nucleic acid molecule comprising said first and second segments or said first and third segments or said second and third segments.

Another embodiment of the present invention relates to a pharmaceutical composition comprising a recombinant nucleic acid molecule comprising said first segment or said second segment or said third segment.

Another embodiment of the present invention relates to a pharmaceutical composition, comprising a recombinant nucleic acid molecule, wherein the recombinant nucleic acid molecule comprises
  a first segment, comprising at least a first sequence corresponding to SEQ ID No:10 wherein said recombinant nucleic acid molecule is capable of expressing said first sequence such that a molecule according to SEQ ID No:2 is produced in a mammalian cell, and/or
  a second segment, comprising at least a first sequence corresponding to SEQ ID No:12 wherein said recombinant nucleic acid molecule is capable of expressing said first sequence such that a molecule according to SEQ ID No:5 is produced in a mammalian cell, and/or
  a third segment, comprising at least a first sequence corresponding to SEQ ID No:14 wherein said recombinant nucleic acid molecule is capable of expressing said first sequence such that a molecule according to SEQ ID No:8 is produced in a mammalian cell.

In a preferred embodiment the pharmaceutical composition comprises a recombinant nucleic acid molecule comprising said first, second and third segments.

Another embodiment of the present invention relates to a pharmaceutical composition comprising a recombinant nucleic acid molecule comprising said first and second segments or said first and third segments or said second and third segments.

Another embodiment of the present invention relates to a pharmaceutical composition comprising a recombinant nucleic acid molecule comprising said first segment or said second segment or said third segment.

Another embodiment of the present invention relates to a pharmaceutical composition, comprising a recombinant nucleic acid molecule, wherein the recombinant nucleic acid molecule comprises
  a first segment, comprising at least a first sequence corresponding to SEQ ID No:1 wherein said recombinant nucleic acid molecule is capable of expressing said first sequence such that a molecule according to SEQ ID No:2 is produced in a mammalian cell, and/or
  a second segment, comprising at least a first sequence corresponding to SEQ ID No:4 wherein said recombinant nucleic acid molecule is capable of expressing said first sequence such that a molecule according to SEQ ID No:5 is produced in a mammalian cell, and/or
  a third segment, comprising at least a first sequence corresponding to SEQ ID No:7 wherein said recombinant nucleic acid molecule is capable of expressing said first sequence such that a molecule according to SEQ ID No:8 is produced in a mammalian cell.

In a preferred embodiment the pharmaceutical composition comprises a recombinant nucleic acid molecule comprising said first, second and third segments.

Another embodiment of the present invention relates to a pharmaceutical composition comprising a recombinant nucleic acid molecule comprising said first and second segments or said first and third segments or said second and third segments.

Another embodiment of the present invention relates to a pharmaceutical composition comprising a recombinant nucleic acid molecule comprising said first segment or said second segment or said third segment.

It is apparent from the foregoing that the above embodiments (A) of the invention relate inter alia to the production and/or provision of the miRNA molecules 130a, 203 and 205 according to SEQ ID Nos:2, 5 and 8 in mammalian cells. However, the skilled person is aware of the fact that also slight variations of the miRNA molecules of the invention are likely to have similar superior effects as described in the present application.

In yet another preferred embodiment of the pharmaceutical compositions of the embodiments (A), said first nucleic acid sequence has no more than four, three, two or one mismatches to a nucleic acid sequence selected from SEQ ID No:2, SEQ ID No:5 and SEQ ID No:8.

In yet another embodiment of the pharmaceutical composition of the embodiments (A), said first nucleic acid sequence comprises, consists of, or has at least about 85%, 90%, 95%, or 100% nucleic acid sequence identity to the sequence corresponding SEQ ID No:2 and/or SEQ ID No:5 and/or SEQ ID No:8.

In yet another preferred embodiment of the pharmaceutical composition of the embodiments (A) said first nucleic acid sequence of any previous aspect comprises or is identical to a nucleic acid sequence selected from SEQ ID No:2, SEQ ID No:5 and SEQ ID No:8.

End of Embodiments (A)

The "recombinant nucleic acid molecules" of the invention preferably comprise all vectors, plasmids, cosmids, viruses and other vectors used for introducing nucleic acids into mammalian cells.

Thus, the present invention particularly relates to a pharmaceutical composition comprising an expression vector comprising the aforementioned isolated polynucleotide according to (a), (b) and/or (c) or combinations thereof as exemplary outlined above for a combination of all of them.

In a preferred embodiment the vector allows for the production of double stranded RNA or single stranded RNA. The expression vector is preferably a eukaryotic expression vector such as e.g. a plasmid, a minichromosome, a cosmid, a bacterial phage, a retroviral vector or any other vector known to the skilled person. The skilled person will be familiar with how to select an appropriate vector according to the specific need.

One example of a suitable expression vector is pLenti6/V5-DEST (e.g. Invitrogen).

Another example of a suitable expression vector which allows for the production of dsRNA directly in the target cell is the so-called pSUPER (available e.g. from OligoEngine, Inc., Seattle, Wash., United States of America). The vector itself and the mechanism how the dsRNA is produced by using said vector is e.g. described in Brummelkamp et al., 2002, Science, Vol. 296, pages 550-553. Another example of such a vector named pSilencer (available from Ambion) was developed by Sui et al., 2002, Proc. Natl. Acad. Sci. Vol. 99, pages 5515-5520.

Certain embodiments (B) relating to the above mentioned vectors are referred to in the following.

In a preferred embodiment of the pharmaceutical compositions of the invention said recombinant nucleic acid molecule is a vector suitable for expression of nucleic acid sequences in a mammalian cell.

In an even more preferred embodiment of the pharmaceutical composition said recombinant nucleic acid molecule comprises a vector for transducing a mammalian cell which encodes the nucleotide sequence of any of the above mentioned embodiments and comprises regulatory sequences operatively linked thereto to allow transcription of said sequence in said cell.

Another preferred embodiment of the invention relates to pharmaceutical compositions, recombinant nucleic acid molecules and the nucleic acid molecules of any previous aspect, wherein said recombinant nucleic acid molecule is a vector comprising:
- a promoter being functional in mammalian cells,
- operatively linked thereto said first nucleic acid sequence, wherein said first nucleic acid sequence encodes for a nucleic acid molecule that is reverse complementary or identical to a nucleic acid selected from the group consisting of SEQ ID No:3, SEQ ID No:6 and SEQ ID No:9 and at least a second sequence being reverse complementary to said first sequence, and
- a termination sequence.

Another preferred embodiment of the invention relates to a pharmaceutical composition, wherein said recombinant nucleic acid molecule is a vector comprising:
- a promoter being functional in mammalian cells,
- operatively linked thereto said first nucleic acid sequence, wherein said first nucleic acid sequence encodes for a nucleic acid molecule that is reverse complementary or identical to a nucleic acid corresponding to SEQ ID No:3 or SEQ ID No:6 or SEQ ID No:9 and at least a second sequence being reverse complementary to said first sequence, and
- a termination sequence.

Another preferred embodiment of the invention relates to a pharmaceutical composition, comprising a combination of three of the above mentioned pharmaceutical compositions, wherein said recombinant nucleic acid molecule is a vector, wherein said first nucleic acid sequences encode for nucleic acid molecules that are reverse complementary or identical to nucleic acids corresponding to SEQ ID No 3, SEQ ID No 6 and SEQ ID No:9, respectively.

Another preferred embodiment of the invention relates to a pharmaceutical composition, comprising a combination of two of the above-mentioned pharmaceutical compositions, wherein said recombinant nucleic acid molecules are vectors, wherein said first nucleic acid sequences encode for nucleic acid molecules that are reverse complementary or identical to nucleic acids corresponding to SEQ ID No 3 and SEQ ID No 6, respectively, or SEQ ID No 3 and SEQ ID No:9, respectively, or SEQ ID No 6 and SEQ ID No:9, respectively.

Yet another preferred embodiment of the invention relates to a pharmaceutical composition, wherein said recombinant nucleic acid molecule is a vector comprising:
- a promoter being functional in mammalian cells,
- operatively linked thereto at least a first nucleic acid sequence, wherein said first nucleic acid sequence encodes for a nucleic acid molecule that is selected from the group consisting of SEQ ID No:10, SEQ ID No:12 and SEQ ID No:14, and
- a termination sequence.

Another preferred embodiment of the invention relates to a pharmaceutical composition, wherein said recombinant nucleic acid molecule is a vector comprising:
- a promoter being functional in mammalian cells,
- operatively linked thereto at least a first nucleic acid sequence, wherein said first nucleic acid sequence encodes for a nucleic acid molecule corresponding to SEQ ID No:10 or SEQ ID No:12 or SEQ ID No:14, and
- a termination sequence.

Another preferred embodiment of the invention relates to a pharmaceutical composition, comprising a combination of three of the above-mentioned pharmaceutical compositions, wherein said recombinant nucleic acid molecules are vectors, wherein said first nucleic acid sequences encode for nucleic acid molecules corresponding to SEQ ID No: 10, SEQ ID No: 12 and SEQ ID No:14, respectively.

Another preferred embodiment of the invention relates to a pharmaceutical composition, comprising a combination of two of the above-mentioned pharmaceutical compositions, wherein said recombinant nucleic acid molecules are vectors, wherein said first nucleic acid sequences encode for nucleic acid molecules corresponding to SEQ ID No: 10 and SEQ ID No: 12, respectively, or SEQ ID No: 10 and SEQ ID No: 14, respectively, or to SEQ ID No: 14 and SEQ ID No: 16, respectively.

Yet another preferred embodiment of the invention relates to a pharmaceutical composition, wherein said recombinant nucleic acid molecule is a vector comprising:
- a promoter being functional in mammalian cells,
- operatively linked thereto at least a first nucleic acid sequence, wherein said first nucleic acid sequence encodes for a nucleic acid molecule that is selected from the group consisting of SEQ ID No:1, SEQ ID No:4 and SEQ ID No:7, and
- a termination sequence.

Another preferred embodiment of the invention relates to a pharmaceutical composition, wherein said recombinant nucleic acid molecule is a vector comprising:
- a promoter being functional in mammalian cells,
- operatively linked thereto at least a first nucleic acid sequence, wherein said first nucleic acid sequence encodes for a nucleic acid molecule corresponding to SEQ ID No:1 or SEQ ID No:4 or SEQ ID No:7, and
- a termination sequence.

Another preferred embodiment of the invention relates to a pharmaceutical composition, comprising a combination of three of the above-mentioned pharmaceutical compositions, wherein said recombinant nucleic acid molecules are vectors, wherein said first nucleic acid sequences encode for nucleic acid molecules corresponding to SEQ ID No: 1, SEQ ID No: 4 and SEQ ID No:7, respectively.

Another preferred embodiment of the invention relates to a pharmaceutical composition, comprising a combination of two of the above-mentioned pharmaceutical compositions, wherein said recombinant nucleic acid molecules are vectors, wherein said first nucleic acid sequences encode for nucleic acid molecules corresponding to SEQ ID No: 1 and SEQ ID No: 4, respectively, or SEQ ID No: 1 and SEQ ID No: 7, respectively, or SEQ ID No: 4 and SEQ ID No: 7, respectively.

Yet another embodiment of the present invention relates to a pharmaceutical composition, comprising a recombinant nucleic acid molecule, wherein the recombinant nucleic acid molecule is a vector comprising
- a promoter, being functional in mammalian cells,
- a first segment, comprising at least a first sequence corresponding to SEQ ID No:3 and at least a second sequence corresponding to the reverse complement of said first sequence, and/or
- a second segment, comprising at least a first sequence corresponding to SEQ ID No:6 and at least a second sequence corresponding to the reverse complement of said first sequence, and/or
- a third segment, comprising at least a first sequence corresponding to SEQ ID No:9 and at least a second sequence corresponding to the reverse complement of said first sequence, and
- a terminator sequence.

In a preferred embodiment the pharmaceutical composition comprises a recombinant nucleic acid molecule wherein the recombinant nucleic acid molecule is a vector comprising said first, second and third segments.

Another embodiment of the present invention relates to a pharmaceutical composition comprising a recombinant nucleic acid molecule wherein the recombinant nucleic acid molecule is a vector comprising said first and second segments or said first and third segments or said second and third segments.

Another embodiment of the present invention relates to a pharmaceutical composition comprising a recombinant nucleic acid molecule wherein the recombinant nucleic acid molecule is a vector comprising said first segment or said second segment or said third segment.

Yet another embodiment of the present invention relates to a pharmaceutical composition, comprising a recombinant nucleic acid molecule, wherein the recombinant nucleic acid molecule is a vector comprising
  a promoter, being functional in mammalian cells,
  a first segment, comprising at least a first sequence corresponding to SEQ ID No:10, and/or
  a second segment, comprising at least a first sequence corresponding to SEQ ID No:12, and/or
  a third segment, comprising at least a first sequence corresponding to SEQ ID No:14, and
  a terminator sequence.

In a preferred embodiment the pharmaceutical composition comprises a recombinant nucleic acid molecule wherein the recombinant nucleic acid molecule is a vector comprising said first, second and third segments.

Another embodiment of the present invention relates to a pharmaceutical composition comprising a recombinant nucleic acid molecule wherein the recombinant nucleic acid molecule is a vector comprising said first and second segments or said first and third segments or said second and third segments.

Another embodiment of the present invention relates to a pharmaceutical composition comprising a recombinant nucleic acid molecule wherein the recombinant nucleic acid molecule is a vector comprising said first segment or said second segment or said third segment.

Yet another embodiment of the present invention relates to a pharmaceutical composition, comprising a recombinant nucleic acid molecule, wherein the recombinant nucleic acid molecule is a vector comprising
  a promoter, being functional in mammalian cells,
  a first segment, comprising at least a first sequence corresponding to SEQ ID No:1, and/or
  a second segment, comprising at least a first sequence corresponding to SEQ ID No:4, and/or
  a third segment, comprising at least a first sequence corresponding to SEQ ID No:7, and
  a terminator sequence.

In a preferred embodiment the pharmaceutical composition comprises a recombinant nucleic acid molecule wherein the recombinant nucleic acid molecule is a vector comprising said first, second and third segments.

Another embodiment of the present invention relates to a pharmaceutical composition comprising a recombinant nucleic acid molecule wherein the recombinant nucleic acid molecule is a vector comprising said first and second segments or said first and third segments or said second and third segments.

Another embodiment of the present invention relates to a pharmaceutical composition comprising a recombinant nucleic acid molecule wherein the recombinant nucleic acid molecule is a vector comprising said first segment or said second segment or said third segment.

According to another preferred embodiment, the present invention relates to a pharmaceutical composition wherein said recombinant nucleic acid molecule is a vector comprising:
  a promoter being functional in mammalian cells,
  operatively linked thereto said first sequence encoding for
    a nucleic acid molecule that is reverse complementary and/or identical to a nucleic acid selected from the group consisting of SEQ ID No:3, SEQ ID No:6 and SEQ ID No:9, optionally a spacer nucleic acid sequence and a second nucleic acid sequence being reverse complementary to said first sequence, and
  a termination sequence.

According to another preferred embodiment of the pharmaceutical composition of the invention, said recombinant nucleic acid molecule is a vector comprising:
  a promoter being functional in mammalian cells,
  operatively linked thereto said first sequence encoding for
    a nucleic acid molecule that is reverse complementary and/or identical to a nucleic acid corresponding to SEQ ID No:3 or SEQ ID No:6 or SEQ ID No:9, optionally a spacer nucleic acid sequence and a second nucleic acid sequence being reverse complementary to said first sequence, and
  a termination sequence.

Another preferred embodiment of the invention relates to a pharmaceutical composition, comprising a combination of three of the above-mentioned pharmaceutical compositions, wherein said recombinant nucleic acid molecules are vectors, wherein said first nucleic acid sequences encode for nucleic acid molecules corresponding to SEQ ID No: 3, SEQ ID No: 6 and SEQ ID No:9, respectively.

Another preferred embodiment of the invention relates to a pharmaceutical composition, comprising a combination of two of the above-mentioned pharmaceutical compositions, wherein said recombinant nucleic acid molecules are vectors, wherein said first nucleic acid sequences encode for nucleic acid molecules corresponding to SEQ ID No: 3 and SEQ ID No: 6, respectively or SEQ ID No: 3 and SEQ ID No: 9, respectively or SEQ ID No: 6 and SEQ ID No: 9, respectively.

Thus, the invention also preferably provides vectors and expression vectors encoding the nucleic acid molecules of any previous aspect.

It is understood that said vectors encoding the nucleic acid molecules of any previous aspect of course are preferably also capable of expressing said at least first (and at least second) sequence(s) such that the miRNA molecules of the invention according to SEQ IDs No:2, 5 and 8 are produced in a mammalian cell, depending on the nature of the first (and second) sequence(s).

In one embodiment, the vector is a retroviral, adenoviral, adeno-associated viral, or lentiviral vector.

According to the invention, promoters and other regulatory elements, include constitutive or inducible promoters, tissue-preferred regulatory elements and/or promoters, and enhancers.

Such promoters comprise, but are not limited to, polymerase III (pol III) transcription units such as the U6- or histone H1-promoter, inducible pol III promoters such as a tetracycline-inducible version H1 promoter [74]. Further, also polymerase II transcription units and/or promoters have been described for the expression of miRNAs, shRNAs, siRNAs and the like [75] and such promoters also from part of the present invention.

A preferred embodiment relates to the above described pharmaceutical compositions of any previous aspect of the invention, wherein the vector is pSUPER.

An even more preferred embodiment of the invention relates to the above described pharmaceutical compositions, wherein the vector is pSUPER and the nucleic acid sequence is selected from SEQ ID No:1, SEQ ID NO.4 and SEQ ID No.7.

An even more preferred embodiment of the invention relates to the above described pharmaceutical compositions, wherein the vector is pSUPER and the nucleic acid sequence is selected from SEQ ID No:3, SEQ ID NO.6 and SEQ ID No.9.

A most preferred embodiment of the invention relates to the above described pharmaceutical compositions, wherein the vector is pSUPER and the nucleic acid sequence is selected from SEQ ID No:10, SEQ ID NO.12 and SEQ ID No.14.

It is apparent from the foregoing that the above embodiments (B) of the invention relate inter alia to the production and/or provision of the miRNA molecules 130a, 203 and 205 according to SEQ ID Nos:2, 5 and 8 in mammalian cells. However, the skilled person is aware of the fact that also slight variations of the miRNA molecules of the invention are likely to have similar superior effects as described in the present application.

In yet another preferred embodiment of the pharmaceutical compositions of the embodiments (B), said first nucleic acid sequence of any previous aspect has no more than four, three, two or one mismatches to a nucleic acid sequence selected from SEQ ID No:2, SEQ ID No:5 and SEQ ID No:8.

In yet another embodiment of the pharmaceutical composition of the embodiments (B), said first nucleic acid sequence comprises, consists of, or has at least about 85%, 90%, 95%, or 100% nucleic acid sequence identity to the sequence corresponding SEQ ID No:2 and/or SEQ ID No:5 and/or SEQ ID No:8.

In yet another preferred embodiment of the pharmaceutical composition of the embodiments (B), said first nucleic acid sequence comprises or is identical to a nucleic acid sequence selected from SEQ ID No:2, SEQ ID No:5 and SEQ ID No:8.
End of Embodiments (B)

Certain embodiments (C) relating to the above mentioned stem loop structures are referred to in the following.

The skilled person is aware of the fact that the miRNAs 130a, 203 and 205 are also present in longer so-called "precursor" or "pre miRNA" molecules that form stem-loop structures which serve as Dicer-substrates (cf. above) and that the miRNAs of the invention may thus also be obtained or produced by the expression of the respective pre-miRNA.

Thus, another embodiment of the invention relates to the above-mentioned pharmaceutical compositions comprising recombinant nucleic acid molecules and relates to the above-mentioned recombinant nucleic acid molecules comprising segments, wherein said first and said second nucleic acid sequences are comprised in stem-loop forming nucleic acids, wherein the stem-loop forming nucleic acids are selected from the group consisting of SEQ ID No:1, SEQ ID No:4, SEQ ID No:7.

In a preferred embodiment said stem-loop forming nucleic acid sequences have a length of between 35 to 3500 nucleotides, preferably of between 35 to 2000 nucleotides, more preferably of between 35 to 120 nucleotides.

Alternatively, synthetic or artificial stem-loop forming nucleic acid sequences can be designed that are also suitable for producing or obtaining the miRNAs of the invention.

Thus, another embodiment of the invention relates to the above-mentioned pharmaceutical compositions comprising recombinant nucleic acid molecules and recombinant nucleic acid molecules comprising segments, wherein said first and said second nucleic acid sequences are comprised in stem-loop forming nucleic acids, wherein the stem-loop forming nucleic acids are selected from the group consisting of SEQ ID No:10, SEQ ID No:12 and SEQ ID No:14.

In a preferred embodiment said stem-loop forming nucleic acid sequences have a length of between 35 to 3500 nucleotides, preferably between 35 to 2000 nucleotides, more preferably between 35 to 120 nucleotides.

Another preferred embodiment of the invention relates to the above-mentioned pharmaceutical compositions according to any of the previous aspects wherein said first and said second nucleic acid sequences are comprised in stem-loop forming nucleic acids, wherein the stem-loop forming nucleic acids are selected from the group consisting of SEQ ID No:1, SEQ ID No:4, SEQ ID No:7, SEQ ID No:10, SEQ ID No:12 and SEQ ID No:14.
End of Embodiments (C)

Alternatively, the miRNAs of the invention can also be administered in the form of RNA molecules.

Thus, in the following, the optionally modified (see above) isolated nucleic acid comprising or consisting of SEQ ID No:2 or SEQ ID No:5 or SEQ ID No:8 or derivatives or fragments thereof will be referred to in more detail.

Preferably, the isolated polynucleotide according to the invention is a single stranded or double stranded RNA molecule.

Preferably, the RNA molecule has a length of between 10 and 200, between 12 and 150, between 12 to 80, between 14 and 60, between 16 and 50, between 17 and 40, more preferably between 18 and 30 nucleotides and most preferably between 18 and 26 nucleotides.

If the isolated polynucleotide according to the invention is a double stranded RNA, e.g. a double stranded miRNA, it is preferred that the antisense strand of said double stranded RNA molecule comprises or consists of SEQ ID No:2 or SEQ ID No:5 or SEQ ID No:8 or a corresponding fragment or derivative thereof and the sense strand of said double stranded RNA molecule comprises or consists of a sequence reverse complementary to SEQ ID No:2 (i.e. SEQ ID No:22) or SEQ ID No:5 (i.e. SEQ ID No:23) or SEQ ID No:8 (i.e. SEQ ID No:24) or a corresponding fragment or derivative thereof.

In another preferred embodiment an isolated polynucleotide according to the invention may be a morpholino molecule.

Morpholino molecules may for example be used in cases where increased stability of the antisense molecule against cellular nucleases is particularly desirable.

In a preferred embodiment morpholino molecules are used as single-stranded polynucleotides.

In another embodiment, heteroduplexes of a morpholino strand and a complementary polynucleotide strand may be used.

The person skilled in the art will be familiar with the concept of morpholino antisense technology and will know how to synthesize and use suitable morpholino molecules. Reference can e.g. also be made to: Summerton J, Weller D, Antisense Nucleic Acid Drug Dev. 1997 June; 7(3):187-95.

Certain embodiments (D) relating to the above mentioned optionally modified nucleic acids are referred to in the following.

In a further preferred embodiment, the present invention relates to a pharmaceutical composition comprising at least one nucleic acid molecule, wherein the at least one nucleic acid molecule comprises a nucleic acid selected from the group consisting of SEQ ID No:2, SEQ ID No:5 and SEQ ID No:8 or a nucleic acid molecule that is reverse complementary thereto.

In yet another preferred embodiment of this pharmaceutical composition of the invention said at least one nucleic acid molecule comprises at least one oligonucleotide.

Yet another preferred embodiment of the invention is a pharmaceutical composition, wherein the at least one nucleic acid molecule comprises at least one modified oligonucleotide.

In another preferred embodiment of the pharmaceutical compositions of the invention said at least one nucleic acid molecule comprises at least one oligonucleotide, selected from the group consisting of SEQ ID No:2, SEQ ID No:5 and SEQ ID No:8.

Another preferred embodiment of the invention relates to the above-mentioned pharmaceutical composition, wherein the at least one oligonucleotide comprises SEQ ID No:2 or SEQ ID No:5 or SEQ ID No:8.

Another preferred embodiment of the invention relates to the above-mentioned pharmaceutical composition, wherein the at least one nucleic acid molecule comprises two oligonucleotides selected from the group consisting of SEQ ID No:2, SEQ ID No:5 and SEQ ID No:8.

Another preferred embodiment of the invention relates to the above-mentioned pharmaceutical composition, wherein the at least one oligonucleotide comprises two oligonucleotides corresponding to SEQ ID No:2 and SEQ ID No:5 or SEQ ID No:2 and SEQ ID No:8 or SEQ ID No:5 and SEQ ID No:8.

Yet another preferred embodiment of the invention relates to the above-mentioned pharmaceutical composition, wherein the at least one oligonucleotide comprises three oligonucleotides selected from the group consisting of SEQ ID No:2, SEQ ID No:5 and SEQ ID No:8.

Yet another preferred embodiment of the invention relates to the above-mentioned pharmaceutical composition, wherein the at least one oligonucleotide comprises three oligonucleotides with each at least 19 nucleotides, at least 20 nucleotides, at least 21 nucleotides, at least 22 nucleotides, at least 23 nucleotides, at least 24 nucleotides, at least 25 nucleotides with a sequence identity of at least preferably 40%, at least preferably 50%, at least preferably 60%, at least preferably 70% and/or 75%, especially preferred at least 80%, 82%, 84%, 86% and/or 88%, particularly preferred at least 90%, 92% and/or 94% and most preferred at least 95%, 96%, 97%, 98% and/or 99% to the nucleic acid sequences corresponding to SEQ ID No:2, SEQ ID No:5 and SEQ ID No:8

Another preferred embodiment of the invention relates to a pharmaceutical composition wherein the at least one oligonucleotide has no more than four, three, two or one mismatches to a nucleic acid sequence selected from SEQ ID No:2, SEQ ID No:5 and SEQ ID No:8.

Another preferred embodiment of the invention relates to a pharmaceutical composition, wherein the at least one oligonucleotide comprises or consists of 15, 16, 17, 18, 19, 20, 21, 22, 23, 24 or 25 linked nucleotides.

Another preferred embodiment of the invention relates to the above-mentioned pharmaceutical composition, wherein the at least one oligonucleotide is a double stranded oligonucleotide.

Yet another preferred embodiment of the invention relates to the above-mentioned pharmaceutical composition, wherein the at least one oligonucleotide is a double stranded oligonucleotide having 5' or 3' overhangs.

Yet another preferred embodiment of the invention relates to the abovementioned a pharmaceutical composition, wherein the at least one oligonucleotide is a double stranded oligonucleotide having no 5' or 3' overhangs.

End of Embodiments (D)

As mentioned above, it is an object of the invention to provide pharmaceutical compositions for the treatment of a neoplastic condition, preferably cancer, more preferably prostate cancer.

Thus, a preferred embodiment of the invention relates to the pharmaceutical composition of the invention for the combined treatment of prostate cancer together with an androgen-depletion therapy.

A particularly preferred embodiment relates to the pharmaceutical composition according to the invention for the treatment of hormone-refractory prostate cancer.

An even more preferred embodiment relates to the pharmaceutical composition according to the invention for the treatment of metastatic prostate cancer.

An even more preferred embodiment relates to the pharmaceutical composition according to the invention for the treatment of recurrent prostate cancer.

Yet another preferred embodiment of the invention relates to the use of a pharmaceutical composition according to the invention for the manufacture of a medicament for the treatment of a neoplastic condition, preferably cancer, more preferably prostate cancer.

Yet another preferred embodiment of the invention relates to the use of a pharmaceutical composition according to the invention for the manufacture of a medicament for the combined treatment of prostate cancer together with an androgen-depletion therapy.

A particularly preferred embodiment relates to the use of a pharmaceutical composition according to the invention for the manufacture of a medicament for the treatment of hormone-refractory prostate cancer.

An even more preferred embodiment relates to the use of a pharmaceutical composition according to the invention for the manufacture of a medicament for the treatment of metastatic prostate cancer.

An even more preferred embodiment relates to the use of a pharmaceutical composition according to the invention for the manufacture of a medicament for the treatment of recurrent prostate cancer.

A pharmaceutical composition according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures.

Thus, a preferred embodiment of the invention relates to a pharmaceutical composition, wherein said pharmaceutical composition is suitable for rectal, oral, inhalative, percutaneous, intravenous (i.v.) or intramuscular (i.m.) or any other route of administration or for implantation.

For the production of pills, tablets, sugar-coated tablets and hard gelatin capsules for example, lactose, starch, for example maize starch, or starch derivatives, talc, stearic acid or its salts, etc may be used. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc.

In some embodiments the pharmaceutical compositions can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Thus, a preferred embodiment of the invention relates to the above-mentioned pharmaceutical composition, wherein said pharmaceutical composition comprises additionally pharmaceutically acceptable excipients selected from the group comprising fillers, lubricants, buffers, salts or preservatives.

Such pharmaceutically acceptable excipients may comprise fillers, anti-stacking agents, lubricants, plasticizers, buffers, stabilizing amino acids, preservatives etc. The precise nature of the excipients will depend on the specific pharmaceutical dosage form comprising the pharmaceutical composition and its way of administration.

Examples of further suitable excipients for the various different forms of pharmaceutical compositions described herein may e.g. be found in the "Handbook of Pharmaceutical Excipients", 2nd Edition, (1994), Edited by A Wade and P J Weller.

In some embodiments the pharmaceutical compositions may be sustained release formulations.

Thus, depending on the dosage forms, suitable embodiments will be considered by the skilled person such as sustained release compositions in the case of oral dosage forms or implantable depot dosage forms. Sustained release dosage forms may be e.g. of the matrix type which may be formed from acrylic polymers, cellulose derivatives etc., of the coating type or the osmotic driven type etc.

In some embodiments, the pharmaceutical compositions according to the invention may comprise the corresponding nucleic acid coding for a miRNA (i.e. either miRNA 130a, 203 and/or 205) or a derivative or a fragment thereof and/or the optionally modified nucleic acid comprising or consisting of a miRNA (i.e. either miRNA 130a, 203 and/or 205) as the only pharmaceutically active agent(s). This may also apply for pharmaceutical compositions comprising different combinations of said miRNAs.

In some embodiments relating to the treatment of prostate cancer, the pharmaceutical composition according to the invention in addition to the nucleic acids of the present invention may further comprise an active agent suitable for the treatment of prostate cancer. Such an agent may e.g. be a chemotherapeutic agent.

Chemotherapeutic agents which are particularly suited for the treatment of prostate cancer include e.g. leuprolide acetate (Lupron), goserelin acetate (Zoladex), bicalutamide, casodex, cyproterone acetate, flutamide (Eulexin), nilutamide (Nilandron), aminoglutethimide (Cytadren), diethylstilbestrol, finasteride (Proscar), ketoconazole (Nizoral), megestrol acetate (Megace), suramin, estramustine phosphate sodium (Emcyt), taxanes, prednisone, paclitaxel, doxorubicin, zoledronic acid, pamidronate, atrasentan, estramustine phosphate aminogluthetimide, ketoconazole, corticosteroids, etoposide, cyclophosphamide, degarelix, (Novantrone), docetaxel (Taxotere), paclitaxel (Taxol).

In other preferred embodiments separate compositions comprising the aforementioned active agents or separate therapies such as an androgen-depletion therapy may be administered to a subject in combination with a pharmaceutical composition according to the present invention in order to treat prostate cancer.

However, as mentioned above, there is presently no therapy in order to treat hormone-refractory prostate cancer. Hormone-refractory prostate cancer seems to be associated with more advanced stages of prostate cancer, which is mostly also metastatic and corresponds to an androgen-independent state of the disease. Clearly, endocrine therapy can no longer be applied in case of hormone-refractory prostate cancer. Further, the chemotherapeutic agents as mentioned above do not seem to provide a sufficiently efficient treatment of hormone-refractory prostate cancer.

In this regard, it should be noted that the inventors of the present invention could inter alia show (see Example section) that all three miRNAs, i.e. miRNA 130a, miRNA 203 and miRNA 205, particularly miRNA 203, alone as well as combinations of said miRNAs, seem to target regulatory molecules of the most important pathways implicated inter alia in a hormone-refractory state of prostate cancer, i.e. regulatory molecules of the AR ("Androgen receptor") pathway and the MAPK ("MAP-kinase") pathway. As can be derived from FIG. 7B, the two pathways seem to be key players for growth and survival of tumour cells.

Since the miRNAs discovered by the inventors seem to target inter alia co-activators of the AR pathway, said co-activators seem to be downregulated and/or inhibited independent of the hormonal state of the prostate cancer, i.e. whether the tumour still responds to hormone therapy or not. Further, since the miRNAs discovered by the inventors seem to target essential regulators of the MAPK pathway as well, the downregulation and/or inhibition of said regulators again seems to be independent of the hormonal state of the prostate cancer. Finally, since both pathways, i.e. the AR pathway and the MAPK pathway, seem to be targeted, the activity of the miRNAs of the present invention seems to be synergistic.

Summarizing the above, the pharmaceutical compositions of the present invention, which are capable of restoring the function of the endogenous miRNAs 130a, miRNA 203 and/ or miRNA 205, seem to be particularly suitable for use in the treatment of hormone-refractory prostate cancer.

Further preferred embodiments (E) related to this aspect are listed in the following. As demonstrated inter alia below, the concomitant expression of miRNA 130a, 203 and 205 seems to inhibit the signaling through the androgen receptor signaling pathway.

Thus, another preferred embodiment of the present invention relates to any of the above mentioned pharmaceutical compositions of the invention, wherein the composition is capable of interfering with, inhibiting or reducing the activity of the androgen-receptor signaling pathway.

In a preferred embodiment, the decrease in AR-signaling is by at least about 5%, 10%, 25%, 50%, 75%, 80%, 90% or even by 100% as compared to activity of AR-signaling in an untreated specimen.

Another object of the present invention relates to any of the above mentioned pharmaceutical compositions of the invention, wherein the composition is capable of reducing the expression of at least one gene in a mammalian cell.

Another preferred embodiment relates to any of the above mentioned pharmaceutical compositions, wherein the composition is capable of reducing the expression of the PDIA3-gene.

Another preferred embodiment relates to any of the above mentioned pharmaceutical compositions, wherein the composition is capable of reducing the expression of the gene encoding ATP-dependent DNA helicase 2 subunit.

In a preferred embodiment, the decrease in expression of the PDIA3 is by at least about 5%, 10%, 25%, 50%, 75%, or even by 100% as compared to the expression level of PDIA3 in an untreated specimen.

In a preferred embodiment, the decrease in expression of the ATP-dependent DNA helicase 2 subunit is by at least about 5%, 10%, 25%, 50%, 75%, or even by 100% as compared to the expression level of ATP-dependent DNA helicase 2 subunit in an untreated specimen.

As mentioned below the target gene of miRNAs 130a, 203 and 205, ATP-dependent DNA helicase 2 subunit, plays a role in neuroectodermal tumors, lung carcinoma esophageal cancer and cervical carcinoma.

It is another object of the invention to provide the above described pharmaceutical compositions for the treatment of neuroectodermal tumors, lung carcinoma esophageal cancer and cervical carcinoma.

Another embodiment relates to the use of a pharmaceutical composition according to the invention for the manufacture of a medicament for the treatment of neuroectodermal tumors, lung carcinoma esophageal cancer and cervical carcinoma.

End of Embodiments (E)

Another aspect of the present invention relates to a method for detecting, grading and/or prognosing cancer comprising the step of determining in a sample from a subject the expression level of a miRNA selected from the group consisting of miRNA 130a and/or miRNA 203 and/or miRNA 205.

"Expression level" of a given miRNA as used herein can also be understood as referring to the "level" of said miRNA or to the "amount" of said miRNA.

The methods according to the invention are preferably performed in vitro.

In one embodiment, determining said expression level(s) is e.g. achieved by contacting the sample from the subject with a detecting agent specific for the corresponding miRNA. In some embodiments, the amount of more than one miRNA selected from the group as mentioned above may be detected in parallel within one sample by applying detecting agents with corresponding selectivities. A detecting agent is specific for a given target, if it binds said target with a higher affinity than any other compound in a sample (i.e. a non-target). Preferably, a detecting agent specific for a given target binds to said target only and does not bind at all to a non-target.

A particularly suitable detecting agent may be an oligonucleotide probe. In a preferred embodiment, the oligonucleotide probe is a single stranded RNA molecule.

The oligonucleotide probe is specific for miRNA 130a and/or miRNA 203 and/or miRNA 205 if it is capable of hybridizing to miRNA 130a and/or miRNA 203 and/or miRNA 205 under highly stringent conditions.

As used herein the term "hybridize" or "hybridizes" refers to the hybridization of a first to a second polynucleotide. To determine whether two polynucleotides hybridize to each other, the skilled person will preferably conduct hybridization experiments in vitro under moderate or stringent hybridization conditions.

Hybridization assays and conditions are known to those skilled in the art and can be found, for example, in Current Protocols in Molecular Biology, John Wiley & Sons, N.Y., 6.3.1-6.3.6, 1991. Stringent conditions may e.g. be conditions in which hybridization takes place in 6× sodium chloride/sodium citrate (SSC) at 45° C., followed by a wash in 0.2× SSC, 0.1% SDS at 65° C.

Another suitable detecting agent may be an antibody or an aptamer. Preferably, the antibody is a monoclonal or polyclonal antibody. In some embodiments the detecting agent may also be selected from antibody variants or fragments such as e.g. single chain antibodies, diabodies, minibodies, single chain Fv fragments (sc(Fv)), sc(Fv)$_2$ antibodies, Fab fragments or a F(ab')$_2$ fragments.

In a preferred embodiment, a detecting agent as described herein may comprise a detectable label. Any suitable label, which can be attached to the detecting agent may be used. In one preferred embodiment the detectable label is covalently or non-covalently attached to the detecting agent. Examples of labels that may be attached to the detecting agent include e.g. fluorescent dyes such as e.g. Cyanine dyes, e.g. Cyanine 3, Cyanine 5 or Cyanine 7, Alexa Fluor dyes, e.g. Alexa 594, Alexa 488 or Alexa 532, fluorescein family dyes, R-Phycoerythrin, Texas Red and rhodamine. Detecting agents may also be labeled with enzymes such as e.g. horseradish peroxidase, alkaline phosphatase or beta-lactamase, radioisotopes such as e.g. $^3H$, $^{14}C$, $^{32}P$, $^{33}P$, $^{35}S$ or $^{125}I$ or metal such as e.g. gold. In another preferred embodiment the detecting agent may also be detected by a secondary detecting agent comprising a label as described above. Preferably a secondary detecting agent is capable of specifically binding to the above described detecting agent. In a particularly preferred embodiment a secondary detecting agent is an antibody.

In some embodiments, said expression level(s) may e.g. be detected in methods involving histological or cell-biological procedures. In some embodiments, visual techniques, such as light microscopy or immunofluoresence microscopy, or flow cytometry or luminometry may be used.

The expression level of miRNA 130a and/or miRNA 203 and/or miRNA 205 may be determined by any suitable technique known in the art. Thus, determining the amount of said miRNAs may e.g. be achieved by in situ hybridization, northern blotting, RNAse protection assays and PCR-based methods, such as e.g. reverse transcription PCR and real time quantitative PCR. The skilled person will know how to perform these methods. In some embodiments total RNA may be isolated from the sample from the subject prior to determining the amount of mRNA.

In further preferred embodiments, determining said expression level(s) in the sample from the subject may be performed alongside measuring or determining the amount of other compounds or factors, such as e.g. determining the level of prostate-specific antigen (PSA) in the same sample or in a different sample from the same subject.

The term "detecting cancer" as used herein means that the presence of a cancerous disease or disorder may be identified in a subject or in a sample from a subject. Preferably, said subject is previously not known to suffer from cancer. In one preferred embodiment the subject is suspected to suffer from cancer. The term "detecting cancer" as used herein is thus meant to encompass "diagnosing cancer". The terms "detecting cancer" and "diagnosing cancer" may be used interchangeably.

The determination or identification of a cancerous disease or disorder may e.g. be accomplished by comparing the expression level of miRNA 130a and/or miRNA 203 and/or miRNA 205 determined in the sample from the subject to the expression level of the respective compound(s) being present in a control as herein described below.

The term "grading cancer" as used herein refers to classifying the cancer by determining certain features of the cancer, such as e.g. its aggressiveness and its prognosis.

The inventors of the present invention have inter alia surprisingly found that decreased levels of miRNA 130a and/or miRNA 203 and/or miRNA 205 seems to correlate with high Gleason scores in human prostate cancer. Therefore, in one preferred embodiment, "grading cancer", preferably prostate cancer, more preferably hormone-refractory prostate cancer, in the context of the present invention may be performed by correlating the amount of miRNA 130a and/or miRNA 203 and/or miRNA 205 determined in the sample from the subject to a cancer grade, preferably a prostate cancer grade such as a hormone-refractory prostate cancer.

Correlating the amount of miRNA 130a and/or miRNA 203 and/or miRNA 205 determined in the sample from the subject to a cancer grade may for example be achieved by comparing the amount of miRNA 130a and/or miRNA 203 and/or miRNA 205 determined in the sample to previously determined values for the amount of miRNA 130a and/or miRNA 203 and/or miRNA 205, which were determined in one or more control sample(s) from subjects known to suffer from cancer, preferably prostate cancer, and which were assigned to different tumor grades, preferably to different Gleason scores.

The term "prognosing cancer" as used herein refers to the prediction of the course or outcome of a diagnosed or detected cancerous disease, e.g. during a certain period of time, e.g. during treatment or after treatment. The term may also refer to a determination of chance of survival or recovery from the cancerous disease, as well as to a prediction of the expected survival time of a subject.

For example, the amount of miRNA 130a and/or miRNA 203 and/or miRNA 205 may be determined in a sample from a subject at a given point of time and compared to the respective amount of miRNA 130a and/or miRNA 203 and/or miRNA 205 determined in a sample from the same subject at a later point of time, wherein a decrease or increase, respectively, in the amount of miRNA 130a and/or miRNA 203 and/or miRNA 205 indicates cancer cell proliferation or cancer regression, respectively. Such an approach may e.g. be used during cancer treatment, e.g. during application of anti-cancer medication to a subject suffering from cancer.

Thus, in a preferred embodiment, the methods according to the invention may be used to monitor the efficacy of cancer treatment in vitro. The efficacy of cancer treatment may e.g. be monitored by detecting the amount of miRNA 130a and/or miRNA 203 and/or miRNA 205 in different samples from a subject that were provided over a given period of time while the subject from which the samples were derived was subjected to anti-cancer treatment. A decrease or increase in the amount of miRNA 130a and/or miRNA 203 and/or miRNA 205 in samples provided from the subject over a given period of time may then indicate the efficacy of anti-cancer treatment.

In a preferred embodiment, the above method further comprises the step of comparing the amount of miRNA 130a and/or miRNA 203 and/or miRNA 205 determined in the sample from the subject to the amount of the respective compound(s) determined in a control. The term "respective compound(s)" means that the amount of each compound in the sample is compared to the amount of the respective compound in the control.

In a preferred embodiment, the control is a sample from a healthy subject. In a preferred embodiment a lower amount of miRNA 130a and/or miRNA 203 and/or miRNA 205 determined in the sample from the subject in comparison to the control indicates the presence of cancer in the subject. The term "lower amount" means that the amount of miRNA 130a and/or miRNA 203 and/or miRNA 205 determined in the sample from the subject is preferably at least 2 fold, at least 3 fold, at least 4 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, at least 500 fold, at least 1000 fold or at least 10000 fold lower than in the control.

In some other preferred embodiments, preferably in cases where grading of the cancer is desired, the control may also be a sample derived from a subject known to suffer from cancer, i.e. a subject that has been independently diagnosed with cancer, preferably with prostate cancer. Preferably a control derived from a subject known to suffer from cancer has previously been subjected to cancer grading. Thus, in one preferred embodiment the amount of miRNA 130a and/or miRNA 203 and/or miRNA 205 determined in the sample from the subject in comparison to the control may indicate the grade of the cancer present in the subject.

In a preferred embodiment, the amount of miRNA 130a and/or miRNA 203 and/or miRNA 205 in the control may be determined in parallel to the amount of miRNA 130a and/or miRNA 203 and/or miRNA 205 in the sample from the subject.

In another preferred embodiment, the control may be a predetermined value. Such a value may e.g. be based on the results of previous experiments determining the amount of miRNA 130a and/or miRNA 203 and/or miRNA 205 in one or more samples from a healthy subject or a subject known to suffer from cancer, preferably prostate cancer. In some embodiments a predetermined value may be derivable from a database.

In a preferred embodiment, the amount of miRNA 130a and/or miRNA 203 and/or miRNA 205 may be compared to more than one control, e.g. to 2, 3, 4, 5, 6, 7, 8, 9, 10, 20, 30, 40, 50, 60, 70, 80, 90, 100 or more than 100 controls.

Preferably, the sample from the subject used in the methods according to the invention is separated from the body of the subject. The sample may be solid or liquid. In a preferred embodiment the sample from the subject is a body fluid or tissue sample, preferably a prostate tissue sample. Preferably, the tissue sample is derived from a cancer tissue, most preferably a prostate cancer tissue. Tissue samples may e.g. be fresh or frozen tissue samples or fixed paraffin embedded samples. In one preferred embodiment the sample may be a biopsy or resection sample.

Preferably, the body fluid is blood, plasma, urine, saliva, serum, semen, prostate fluid or seminal fluid.

In some embodiments, a liquid sample may be enriched for cells of interest, e.g. prostate cells. Enrichment may be performed by any method known to the skilled person. Enrichment may e.g. be achieved by using a solid support, e.g. a column, coated with a specific antibody, such as e.g. a prostate specific antibody. Alternatively, enrichment may e.g. also be achieved by using filtration methods or by immobilizing specific aptamers on a microfluidic channel and pumping the liquid sample through the device.

In a further aspect the present invention relates to a diagnostic kit for detecting, grading, and/or prognosing cancer comprising a detecting agent specific for miRNA 130a and/or miRNA 203 and/or miRNA 205.

Preferably, the diagnostic kit according to the invention contains one or more detecting agents specific for miRNA 130a and/or miRNA 203 and/or miRNA 205. If the diagnostic kit according to the invention comprises more than one detecting agent, said detecting agents are preferably each specific for one compound selected from the group of miRNA 130a and miRNA 203 and miRNA 205.

Suitable detecting agents have been described herein above. The diagnostic kit may further comprise additional components or reagents that may be suitable for performing the methods according to the invention, such as e.g. buffers or controls. The components contained in the diagnostic kit may be comprised in one or more containers. The diagnostic kit according to the present invention may also comprise an instruction leaflet, which indicates how to use the diagnostic kit and its components.

As mentioned above, the inventors have surprisingly found that cancer, particularly prostate cancer, seems to be associated with a downregulation of miRNA 130a and miRNA 203 and miRNA 205. The present invention in a further aspect thus relates to the use of miRNA 130a and miRNA 203 and miRNA 205 as marker for cancer, preferably prostate cancer, and more preferably hormone-refractory prostate cancer, wherein a downregulation and/or absence of at least one of said miRNAs is indicative for said cancer.

Further embodiments (F) related thereto are mentioned in the following:

Given the fact, that the expression of miRNAs 130a, 203 and 205 seems to decrease depending on the stage of the tumor, that is, the more advanced the stage the lower the expression, the skilled person is aware that the expression-level of miRNAs 130a, 203 and 205 may be used as a diagnostic marker for prostate cancer samples.

Thus another object of the present invention is a method of diagnosing prostate cancer in an individual, comprising the steps of
  a) obtaining a cellular sample from an individual being potentially afflicted with prostate cancer;
  b) determining the expression level of miRNAs 130a, 203 and 205 in said cellular sample outside the individual's body;
  c) comparing said expression level of miRNAs 130a, 203 and 205 with expression level of miRNAs 130a, 203 and 205 in a cellular sample obtained from an individual not afflicted with prostate cancer;
  d) determining the occurrence of prostate cancer by observing a decreased expression level of miRNAs 130a, 203 and 205 in b) compared to c).

The sample is preferably outside the human or animal body.

The same applies for the possibility to define or identify the exact stage of prostate cancer in an individual.

Thus another object of the present invention is a method of grading prostate cancer in an individual, comprising the steps of
  a) obtaining a cellular sample from an individual being potentially afflicted with prostate cancer;
  b) determining the expression level of miRNAs 130a, 203 and 205 in said cellular sample outside the individual's body;
  c) comparing said expression level of miRNAs 130a, 203 and 205 with expression level of miRNAs 130a, 203 and 205 in cellular samples of different stages of prostate cancer;
  d) determining the stage of prostate cancer by comparing the expression level of miRNAs 130a, 203 and 205 between b) and c).

The sample is preferably outside the human or animal body.

End of Embodiments (F)

Further preferred embodiments of the invention relate to:
1. A pharmaceutical composition comprising
   an isolated nucleic acid coding for a miRNA comprising or consisting of SEQ ID No:2 or a derivative or fragment thereof; and/or
   an optionally modified isolated nucleic acid comprising or consisting of SEQ ID No:2 or a derivative or fragment thereof;
   for use in the treatment of prostate cancer.
2. Pharmaceutical composition according to 1, wherein the composition is for use in the treatment of hormone-refractory prostate cancer.
3. Pharmaceutical composition according to 1 or 2, wherein said derivative displays a sequence identity of 70%, preferably of 80%, and most preferably of 90% to the SEQ ID No:2.
4. Pharmaceutical composition according to 1 to 3, wherein said fragment corresponds to a portion of 18, preferably of 20 and most preferably of 21 nucleotides of the SEQ ID No:2.
5. Pharmaceutical composition according to 1 to 4, wherein said isolated nucleic acid coding for said miRNA is a double stranded DNA.
6. Pharmaceutical composition according to 5, wherein said double stranded DNA codes for a precursor of said miRNA, which is then processed to said miRNA, wherein said precursor preferably comprises a stem-loop structure.
7. Pharmaceutical composition according to 5, wherein said double stranded DNA comprises the SEQ ID No:3 or a derivative or fragment thereof and the SEQ ID No:22 or a fragment or derivative thereof within the same polynucleotide strand, optionally separated by a spacer.
8. Pharmaceutical composition according to 1 to 4, wherein said optionally modified isolated nucleic acid is a single stranded or doubled stranded RNA, preferably of a length of 18 to 25, more preferably of 19 to 24 and most preferably of 20 to 22 nucleotides.
9. Pharmaceutical composition according to any of 1 to 4, 7 or 8, wherein said nucleic acid is modified by at least one modification selected from the group consisting of a 2'-O-methyl-ribonucleotide, a phosphorothioate bond, a N3'-P5' phosphoroamidate bond, a peptide-nucleic acid bond, a C-5 thiazole uracil, a C-5 propynyl-cytosine, a phenoxazine-modified cytosine, a 2'-β-propyl ribose and a 2'-methoxyethoxy ribose.
10. Pharmaceutical composition according to any of 1 to 9, wherein said composition additionally comprises
   an isolated nucleic acid coding for a miRNA comprising or consisting of SEQ ID No:5 or a derivative or fragment thereof; and/or
   an optionally modified isolated nucleic acid comprising or consisting of SEQ ID No:5 or a derivative or fragment thereof; and/or
   an isolated nucleic acid coding for a miRNA comprising or consisting of SEQ ID No:8 or a derivative or fragment thereof; and/or
   an optionally modified isolated nucleic acid comprising or consisting of SEQ ID No:8 or a derivative or fragment thereof,
   wherein said isolated nucleic acids coding for said miRNAs are optionally comprised within a single isolated nucleic acid.

11. A method for detecting, grading and/or prognosing prostate cancer, preferably hormone-refractory prostate cancer, comprising the step of determining in a sample from a subject the expression level of miRNA 130a, optionally in combination with the expression level(s) of miRNA 203 and/or miRNA 205.

12. The method according to 11, further comprising the step of comparing said expression level(s) determined in the sample from the subject to the expression level(s) of the respective compound(s) determined in a control.

13. The method according to 11 or 12, wherein the sample from the subject is a body fluid or tissue sample, preferably a prostate tissue sample.

14. The method according to 13, wherein the body fluid is selected from the group of blood, plasma, urine, saliva, serum, semen, prostate fluid or seminal fluid.

15. A diagnostic kit for detecting, grading and/or prognosing prostate cancer, preferably hormone-refractory prostate cancer, comprising a detecting agent specific for miRNA 130a, optionally in combination with a detecting agent specific for miRNA 203 and/or miRNA 205.

16. The diagnostic kit according to 15, wherein the detecting agent is an antibody, an aptamer or an oligonucleotide probe.

17. Use of miRNA 130a, optionally in combination with miRNA 203 and/or miRNA 205, as marker for prostate cancer, preferably hormone-refractory prostate cancer.

Still further preferred embodiments of the invention relate to:

1. A pharmaceutical composition comprising at least two isolated nucleic acids from different subgroups selected from the group of subgroups consisting of
    subgroup A: an isolated nucleic acid coding for a miRNA comprising or consisting of SEQ ID No:2 or a derivative or fragment thereof; and/or
    an optionally modified isolated nucleic acid comprising or consisting of SEQ ID No:2 or a derivative or fragment thereof; and
    subgroup B: an isolated nucleic acid coding for a miRNA comprising or consisting of SEQ ID No:5 or a derivative or fragment thereof; and/or an optionally modified isolated nucleic acid comprising or consisting of SEQ ID No:5 or a derivative or fragment thereof; and
    subgroup C: an isolated nucleic acid coding for a miRNA comprising or consisting of SEQ ID No:8 or a derivative or fragment thereof; and/or
    an optionally modified isolated nucleic acid comprising or consisting of SEQ ID No:8 or a derivative or fragment thereof.

2. Pharmaceutical composition according to 1, wherein the composition is for use in the treatment of cancer, preferably prostate cancer.

3. Pharmaceutical composition according to 1 or 2, wherein the composition is for use in the treatment of hormone-refractory prostate cancer.

4. Pharmaceutical composition according to 1 to 3, wherein said derivative displays a sequence identity of 70%, preferably of 80%, and most preferably of 90% to the SEQ ID No:2.

5. Pharmaceutical composition according to 1 to 4, wherein said fragment corresponds to a portion of 18, preferably of 20 and most preferably of 21 nucleotides of the SEQ ID No:2.

6. Pharmaceutical composition according to 1 to 5, wherein said isolated nucleic acid coding for said miRNA is a double stranded DNA.

7. Pharmaceutical composition according to 6, wherein said double stranded DNA codes for a precursor of said miRNA, which is then processed to said miRNA, wherein said precursor preferably comprises a stem-loop structure.

8. Pharmaceutical composition according to 7, wherein said double stranded DNA coding for a miRNA comprising or consisting of SEQ ID No:2 or a derivative or fragment thereof comprises the SEQ ID No:3 or a derivative or fragment thereof and the SEQ ID No:22 or a fragment or derivative thereof within the same polynucleotide strand, optionally separated by a spacer; and wherein said double stranded DNA coding for a miRNA comprising or consisting of SEQ ID No:5 or a derivative or fragment thereof comprises the SEQ ID No:6 or a derivative or fragment thereof and the SEQ ID No:23 or a fragment or derivative thereof within the same polynucleotide strand, optionally separated by a spacer; and wherein said double stranded DNA coding for a miRNA comprising or consisting of SEQ ID No:8 or a derivative or fragment thereof comprises the SEQ ID No:9 or a derivative or fragment thereof and the SEQ ID No:24 or a fragment or derivative thereof within the same polynucleotide strand, optionally separated by a spacer; wherein said isolated nucleic acids coding for said miRNAs are optionally comprised within a single isolated nucleic acid.

9. Pharmaceutical composition according to 1 to 5, wherein said optionally modified isolated nucleic acid is a single stranded or doubled stranded RNA, preferably of a length of 18 to 25, more preferably of 19 to 24 and most preferably of 20 to 22 nucleotides.

10. Pharmaceutical composition according to any of 1 to 5, 8 or 9, wherein said nucleic acid is modified by at least one modification selected from the group consisting of a 2'-O-methyl-ribonucleotide, a phosphorothioate bond, a N3'-P5' phosphoroamidate bond, a peptide-nucleic acid bond, a C-5 thiazole uracil, a C-5 propynyl-cytosine, a phenoxazine-modified cytosine, a 2'-β-propyl ribose and a 2'-methoxyethoxy ribose.

11. Pharmaceutical composition according to any of 1 to 10, wherein said composition comprises at least one isolated nucleic acids from each of the different subgroups A, B and C.

12. A method for detecting, grading and/or prognosing cancer, preferably prostate cancer, more preferably hormone-refractory prostate cancer, comprising the step of determining in a sample from a subject the expression level of at least two miRNAs selected from the group consisting of miRNA 130a, miRNA 203 and miRNA 205.

13. The method according to 12, further comprising the step of comparing said expression level(s) determined in the sample from the subject to the expression level(s) of the respective compound(s) determined in a control.

14. The method according to 12 or 13, wherein the sample from the subject is a body fluid or tissue sample, preferably a prostate tissue sample.

15. The method according to 14, wherein the body fluid is selected from the group of blood, plasma, urine, saliva, serum, semen, prostate fluid or seminal fluid.

16. A diagnostic kit for detecting, grading and/or prognosing cancer, preferably prostate cancer, more preferably hormone-refractory prostate cancer, comprising at least one detecting agent specific for at least two miRNAs selected from the group consisting of miRNA 130a, miRNA 203 and miRNA 205.

17. The diagnostic kit according to 16, wherein the detecting agent is an antibody, an aptamer or an oligonucleotide probe.

18. Use of at least two miRNAs selected from the group consisting of miRNA 130a, miRNA 203 and miRNA 205 as marker for prostate cancer, preferably hormone-refractory prostate cancer.

Definitions

It is to be understood that the term "comprise", and variations such as "comprises" and "comprising" is not limiting. For the purpose of the present invention the term "consisting of" is considered to be a preferred embodiment of the term "comprising". If hereinafter a group is defined to comprise at least a certain number of embodiments, this is meant to also encompass a group which preferably consists of these embodiments only.

As used in this application, "microRNAs" (miRNA) are single-stranded RNA molecules generally of 15 to 25 nucleotides in length excised from 50- to 120-nucleotide shRNA precursors involved in the regulation of expression of protein-coding genes (PCGs), which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression. microRNAs are processed from their longer pri-miRNA precursor transcripts that range in size from approximately 50 to 3500 nt. In animals, the enzyme involved in processing miRNA precursors is called Dicer, an RNAse Ill-like protein [76, 77, 78] Furthermore, it is becoming clear from recent work that at least some miRNA hairpin precursors originate as longer polyadenylated transcripts, and several different miRNAs and associated hairpins can be present in a single transcript [79].

"pri-miRNAs" or "primary miRNAs" are long, polyadenylated RNAs transcribed by RNA polymerase II that encode miRNAs. "pre-miRNAs" are primary miRNAs that have been processed to form a shorter sequence that has the capacity to form a stable hairpin and is further processed to release a miRNA. In plants both processing steps are carried out by dicerlike and it is therefore difficult to functionally differentiate between "pri-miRNAs" and "pre-miRNAs". Therefore, a precursor miRNA, or a primary miRNA, is functionally defined herein as a nucleotide sequence that is capable of producing a miRNA. Given this functional definition, and as will be clear from the Examples and discussion herein, a precursor miRNA, primary miRNA and/or a miRNA of the invention can be represented as a ribonucleic acid or, alternatively, in a deoxyribonucleic acid form that "corresponds substantially" to the precursor miRNA, primary miRNA and/or miRNA. It is understood that the DNA in its double-stranded form will comprise a strand capable of being transcribed into the miRNA precursor described. Expression constructs, recombinant DNA constructs, and transgenic organisms incorporating the miRNA encoding DNA that results in the expression of the described miRNA precursors are described.

"pre-miRNAs" are primary miRNAs that have been processed to form a shorter sequence that has the capacity to form a stable hairpin and is further processed to release a miRNA. Therefore, a precursor miRNA, or a primary miRNA, is functionally defined herein as a nucleotide sequence that is capable of producing a miRNA. Given this functional definition, and as will be clear from the Examples and discussion herein, a precursor miRNA, primary miRNA and/or a miRNA of the invention can be represented as a ribonucleic acid or, alternatively, in a deoxyribonucleic acid form that "corresponds substantially" to the precursor miRNA, primary miRNA and/or miRNA. It is understood that the DNA in its double-stranded form will comprise a strand capable of being transcribed into the miRNA precursor described.

The term "sense" is used to denote that typically the polarity of a given DNA/RNA-sequence is given as being 5'-3'. Along the same lines, the term "antisense" denotes that a sequence is given in the 3'-5' direction.

The term "nucleic acid" or "polynucleotide" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (Pl, PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, tRNA, vRNA, and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues [80, 81].

"Nucleotides" contain a sugar deoxyribose (DNA) or ribose (RNA), a base, and a phosphate group. Nucleotides are linked together through the phosphate groups.

"Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "sequence identity" as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment.

As used in this application, "complementary" refers to the base pairing relationship between strands of nucleic acids arranged in an antiparallel manner, such that the strands will hybridize with sufficient strength under intracellular conditions.

As used in this application, the term "reverse complement" refers to a nucleic acid that can hybridize with another given nucleic acid sequence on the same strand of a given nucleic acid molecule because of it's complementary and the polarity relative to the other sequence. If, for example a first sequence features a 5'-3' sequence of AATTGGCA; then the according "reverse complement" or "reverse complementary" sequence to the first sequence would be on the same strand of DNA and have the 5'-3' sequence of TGCCAATT. If topologically there is a possibility for base pairing of these two sequences, i.e. there is, for example, a non-self-pairing "spacer" sequence between these two sequences long enough to allow for base pairing of the two abovementioned sequences, a so called "stem-loop" sequence would form, in which the hybridized sequences woud form the "stem", and the non-self hybridizing spacer would form the "loop". These "stem-loop" structures are substrates for enzymes like Dicer etc. that thus release miRNAs, shRNAs, siRNAs from such or other precursors.

As used in this application, the term "gene product" refers to the product of transcription or translation of a gene sequence. This may include RNA or protein products, including or regardless of later processing or conformational changes.

As used in this application, the term "3'-UTR" or "3'-untranslated region" is a particular section of messenger RNA (mRNA) that follows the coding region. This region contains transcription and translation regulating sequences.

As used herein, "encodes" or "encoding" refers to a DNA sequence which can be processed to generate an RNA and/or polypeptide. As used herein, "expression" or "expressing" refers to production of a functional product, such as, the generation of an RNA transcript from an introduced construct, an endogenous DNA sequence, or a stably incorporated heterologous DNA sequence. The term may also refer to a polypeptide produced from an mRNA generated from any of the above DNA precursors. Thus, expression of a nucleic acid fragment may refer to transcription of the nucleic acid fragment (e.g., transcription resulting in mRNA or other functional RNA) and/or translation of RNA into a precursor or mature protein (polypeptide).

As used in this application, the term "reduce the expression of a gene" refers to the reduction of the amount of a product of the gene. This includes RNA and proteins in all forms.

As used in this application the term "spacer" or "linker" refers to a stretch of nucleotides that is interspersed between two nucleic acid sequences that can hybridize with each other to form a so-called "stem-loop" structure.

The spacer may be made up of a nucleic acid sequence that cannot self hybridize, thus it may form the "loop" in the "stem-loop"-structure.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

By "vector" is meant a nucleic acid molecule, for example, a plasmid, cosmid, or bacteriophage, that is capable of replication in a host cell. Preferably, a vector is an expression vector that is a nucleic acid construct, generated recombinantly or synthetically, bearing a series of specified nucleic acid elements that enable transcription of a nucleic acid molecule in a host cell. Typically, expression is placed under the control of certain regulatory elements, including constitutive or inducible promoters, tissue-preferred regulatory elements, and enhancers. Transducing viral (e.g., retroviral, adenoviral, lentiviral and adeno-associated viral) vectors can be used for somatic cell gene therapy, especially because of their high efficiency of infection and stable integration and expression [82,83]. For example, a polynucleotide encoding a nucleic acid molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Eglitis et al., BioTechniques 6:608-614, 1988;). Retroviral vectors are particularly well developed and have been used in clinical settings (Rosenberg et al., N. Engl. J. Med 323:370, 1990).

By "operably linked" is meant that a first polynucleotide is positioned adjacent to a second polynucleotide that directs transcription of the first polynucleotide when appropriate molecules (e.g., transcriptional activator proteins) are bound to the second polynucleotide. By "positioned for expression" is meant that the polynucleotide of the invention (e.g., a DNA molecule) is positioned adjacent to a DNA sequence that directs transcription and translation of the sequence (i.e., facilitates the production of, for example, a microRNA molecule described herein) As used in this application "oligonucleotides" means a short sequence of nucleic acids, no more than 200 bases long. An oligonucleotide may be made of DNA, RNA or a combination, and may be chemically modified to increase stability.

As used in this application the term "chemically modified" or "modified" refers to oligonucleotides and/or nucleic acid molecules based on 2'-modified oligonucleotides containing oligodeoxynucleotide gaps with some or all internucleotide linkages modified to phosphorothioates for nuclease resistance. The presence of methylphosphonate modifications increases the affinity of the oligonucleotide for its target RNA and thus reduces the IC50. This modification also increases the nuclease resistance of the modified oligonucleotide. It is understood that the methods and reagents of the present invention may be used in conjunction with any technologies that may be developed to enhance the stability or efficacy of an inhibitory nucleic acid molecule. Such nucleic acid molecules include nucleobase oligomers containing modified backbones or non-natural internucleoside linkages. Oligomers having modified backbones include those that retain a phosphorus atom in the backbone and those that do not have a phosphorus atom in the backbone. For the purposes of this specification, modified oligonucleotides that do not have a phosphorus atom in their internucleoside backbone are also considered to be nucleobase oligomers.

Nucleobase oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest- ers, and boranophosphates. Various salts, mixed salts and free acid forms are also included.

Nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Nucleobase oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleobase oligomer, particularly the 3' position of the sugar on the 3' terminal nucleotide.

Nucleobase oligomers may also have sugar mimetics such as cyclobutyl moieties in place of the pentofuranosyl sugar. In other nucleobase oligomers, both the sugar and the internucleoside linkage, i.e., the backbone, can be replaced with novel groups. Methods for making and using these nucleobase oligomers are described, for example, in "Peptide Nucleic Acids (PNA): Protocols and Applications" Ed. P. E. Nielsen, Horizon Press, Norfolk, United Kingdom, 1999. Representative Further teaching of PNA compounds can be found in Nielsen et al., Science, 1991, 254, 1497-1500. In other embodiments, a single stranded modified nucleic acid molecule (e.g., a nucleic acid molecule comprising a phosphorothioate backbone and 2'-O-Me sugar modifications is conjugated to cholesterol. Such conjugated oligomers are known as "antagomirs." Methods for silencing microRNAs in vivo with antagomirs are described, for example, in Krutzfeldt et al., Nature 438: 685-689.

As used in this application, "shRNA" means short hairpin RNA. It is a sequence of RNA that makes a tight hairpin turn that can be used to silence gene expression via RNA interference. The shRNA hairpin structure is cleaved by the cellular machinery and are precursors to miRNA.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, prostate, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers.

As used herein, a "tumor" comprises one or more cancerous cells.

As used in this application, the terms "treatment" or "treating" refer to the application of an agent with the intent to produce a benefit to a patient being treated. Such a benefit need not be a complete or permanent cure, but may be only a lessening of the rate at which tumorigenesis is occurring, thereby delaying onset or progression of metastases, particularly to bone and lung. In addition, such treatment need not in actuality produce the beneficial, as long is it is given with the intention of obtaining a result.

The term "isolated" in the context of the present invention indicates that a polynucleotide has been removed from its natural environment and/or is presented in a form in which it is not found in nature.

The term "subject" as used herein preferably refers to a human. However, veterinary applications are also in the scope of the present invention. The term "subject" can therefore also refer to an animal, preferably a mammal such as e.g. non-human primates, mice, rats, rabbits, guinea pigs, dogs, cats, cattle, horses, sheep, pigs, goats and the like.

The term "aptamer" as used herein refers to a polynucleotide that has a specific binding affinity for a target compound or molecule of interest, e.g. a nucleotide. Aptamers may e.g. be RNA, single stranded DNA, modified RNA or modified DNA molecules. The preparation of aptamers is well known in the art and may involve, inter alia, the use of combinatorial RNA libraries to identify binding sites (reference may e.g. be made to Gold (1995), Ann. Rev. Biochem 64, 763-797).

EXAMPLES

Example 1

Expression of miRNAs in Prostate Cell Lines and Prostate Tumors

Using microarray based microRNA expression analysis of the PCa cell lines LNCaP, PC3 and Du-145 compared to the normal prostate epithelial cell line RWPE-1, the inventors identified 30 miRNAs that were significantly differentially expressed (p<0.0001) (11 up- and 19 downregulated) between the 'normal' and 'cancer' state (FIG. 1A), among them:

miR-130a (p-value = 0.0000456); Stem loop sequence
Acc. No. MI0000448 (mature sequence bold):
(SEQ ID No: 1)
UGCUGCUGGCCAGAGCUCUUUUCACAUUGUGCUACUGUCUGCACCUGU

CACUAGCAGUGCAAUGUUAAAAGGGCAUUGGCCGUGUAGUG;

Mature sequence Acc. Nr. MIMAT0000425 (Nt 55-76:)
(SEQ ID No: 2)
CAGUGCAAUGUUAAAAGGGCAU miR-203(p-value = 0.0000206); Stem loop sequence
Acc. No. MI0000283 (mature sequence bold):
(SEQ ID No: 4)
GUGUUGGGGACUCGCGCGCUGGGUCCAGUGGUUCUUAACAGUUCAACA

GUUCUGUAGCGCAAUUGUGAAAUGUUUAGGACCACUAGACCCGGCGG

GCGCGGCGACAGCGA;

Mature sequenceAcc. MIMAT0000264 (Nt 65-86:)
(SEQ ID No: 5)
GUGAAAUGUUUAGGACCACUAG miR-205 (p-value = 0.0000000631); Stem loop
sequence Acc. No. MI0000285 (mature sequence bold:)
(SEQ ID No: 7)
AAAGAUCCUCAGACAAUCCAUGUGCUUCUCUUGUCCUUCAUUCCACCG

GAGUCUGUCUCAUACCCAACCAGAUUUCAGUGGAGUGAAGUUCAGGA

GGCAUGGAGCUGACA;

Mature sequence Acc. No. MIMAT0000266 (Nt. 34-55):
(SEQ ID No: 8)
UCCUUCAUUCCACCGGAGUCUG The downregulation of miRNA 130a, 203 and 205 could be confirmed by quantitative RT-PCR (see FIG. 1B) and in tissue samples classified according to the Gleason score (see FIG. 1C). The Gleason score is the most frequently used grading system for prostate cancer and is based on scoring the two most predominant glandular differentiation patterns in the sample [30].

Example 2

Figure 2A:
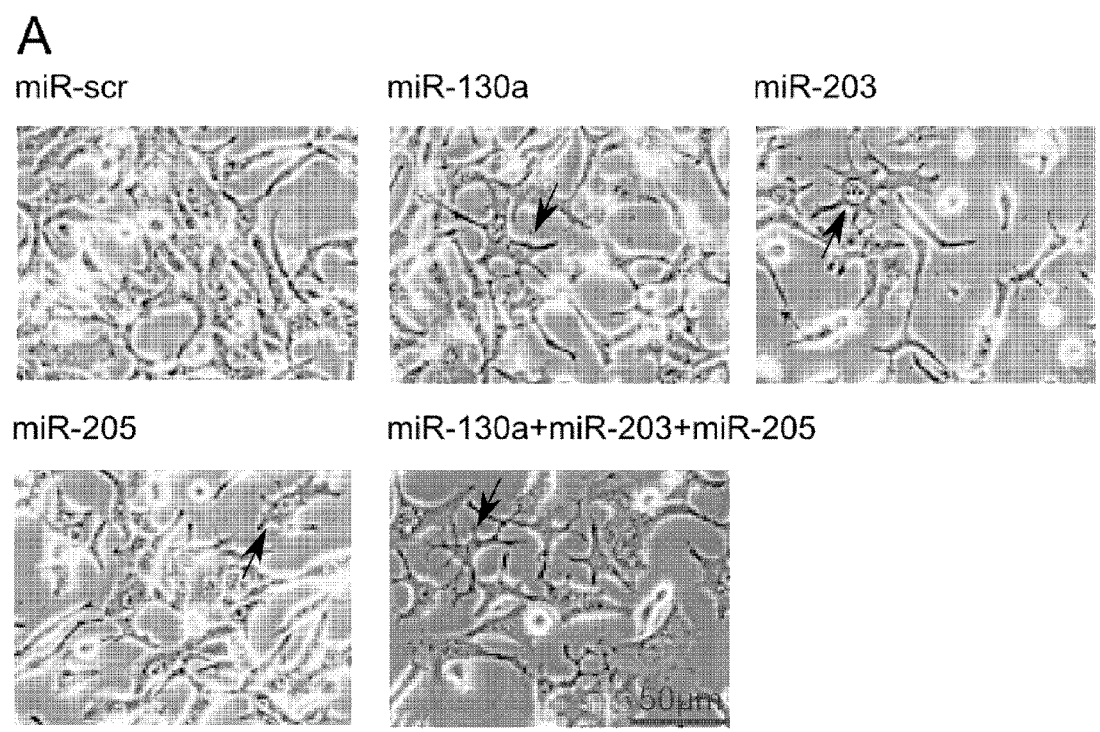
FIG. 2. MiR-130a, miR-203, and miR-205 reconstitution impairs growth of LNCaP cells. (A) LNCaP cells were transfected with miR-scr as a control or miR-130a, miR-203, miR-205 or any combination. Compared to miR-scr, reconstitution of the miRNAs separately or in combination induced a neuronal or dendritic-like morphology (indicated by arrows), 48 h post-transfection, as assessed by microscopy. (B-E) LNCaP cells were transfected with miRNA and miR-scr expression vectors, respectively, and (B) cell numbers were assessed at the indicated time points by cell counting using a Neubauer chamber (n=3 to 5). Cell numbers were normalized to day 3 to eliminate variation in viability due to electroporation observed within the first two days post-transfection. (C) Apoptosis was measured at the indicated time points using a caspase 3/7 assay (n=3 to 5). (D) Influence of the three miRNAs on the cell cycle was analyzed using PI staining and flow cytometry 3 days post-transfection (n=5). All data represent mean+Stdv.

Reconstitution of miR-130a, miR-203 and/or miR-205 Induces a Change in Cell Morphology and a Strong Apoptotic Reaction, and/or Cell Cycle Arrest The pSuper-vector system described by [31] was adopted to knock-in and thus reconstitute miRNAs130a, 203 and 205, respectively, into the LNCaP cell line. LNCaP displays a loss of these miRNAs comparable to PCa tumor samples. Overexpression of miR-130a or miRNA 205 led to a change in cell morphology, with the cells becoming neuronal or dendritic like, comparable to the morphological change observed upon androgen-deprivation or AR-knockdown [32,9]. Overexpression of miR-203 not only induced a dendritic-like shape, but in addition the cells became flattened with pseudopodida like excrescences (FIG. 2A). Transfection of any combination of the miRNAs led to morphological change similar but more pronounced than the effect of individually overexpressed miRNAs (exemplary shown for a combination of all three in FIG. 2A).

Figure 2B:
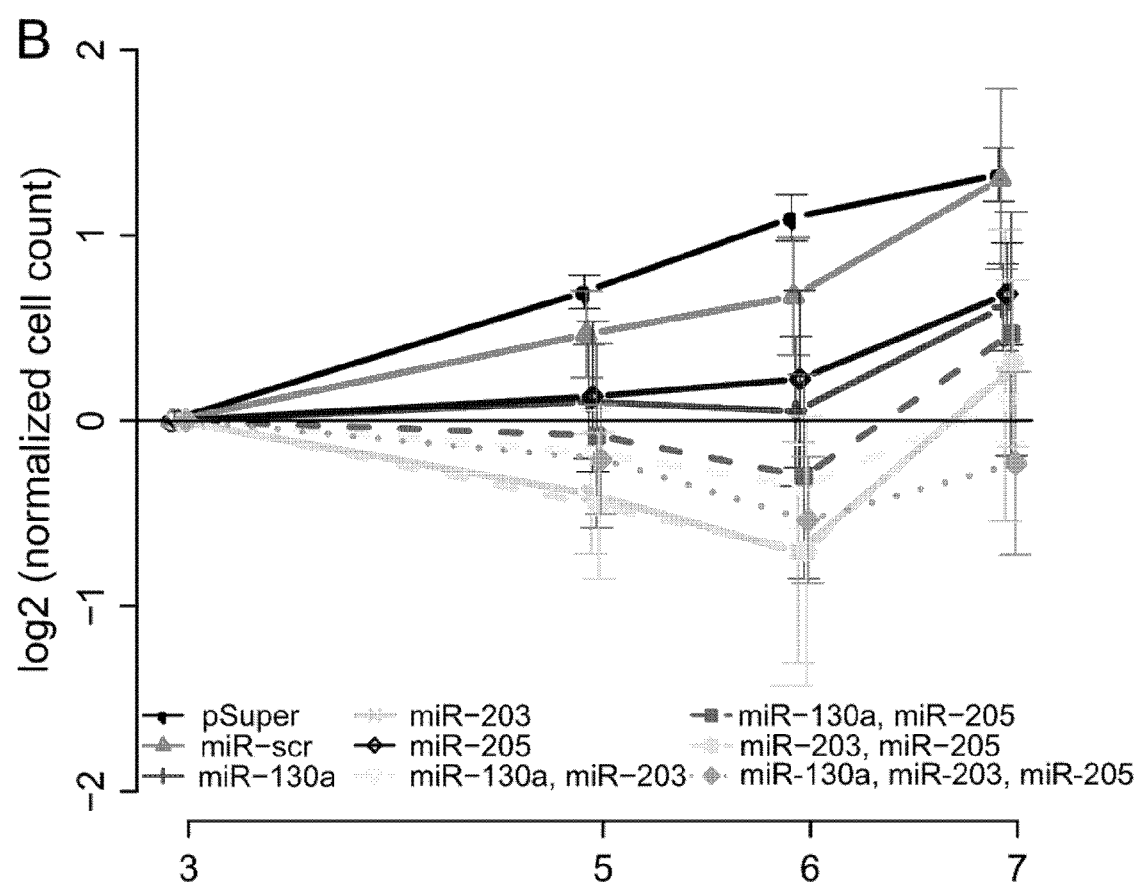

Besides cell morphology, the inventors assessed proliferation kinetics upon reconstitution of the miRNAs (FIG. 2B). While transfection of empty p-Super vector or miR-scr resulted in exponential growth, overexpression of miR-130a or miRNA 205 caused stagnation until day 6. In contrast, combined overexpression of these two miRNAs induced a significant ($p<0.01$) decrease in cell number. MiR-203 and miR-203+miR-205 and the triple combination showed a comparable, significant ($p<0.01$) decrease in cell numbers over days 5 and 6. The triple combination of miRNAs still showed a net loss of cells compared to day 3 indicating a synergistic action of the three miRNAs.

Figure 2C:
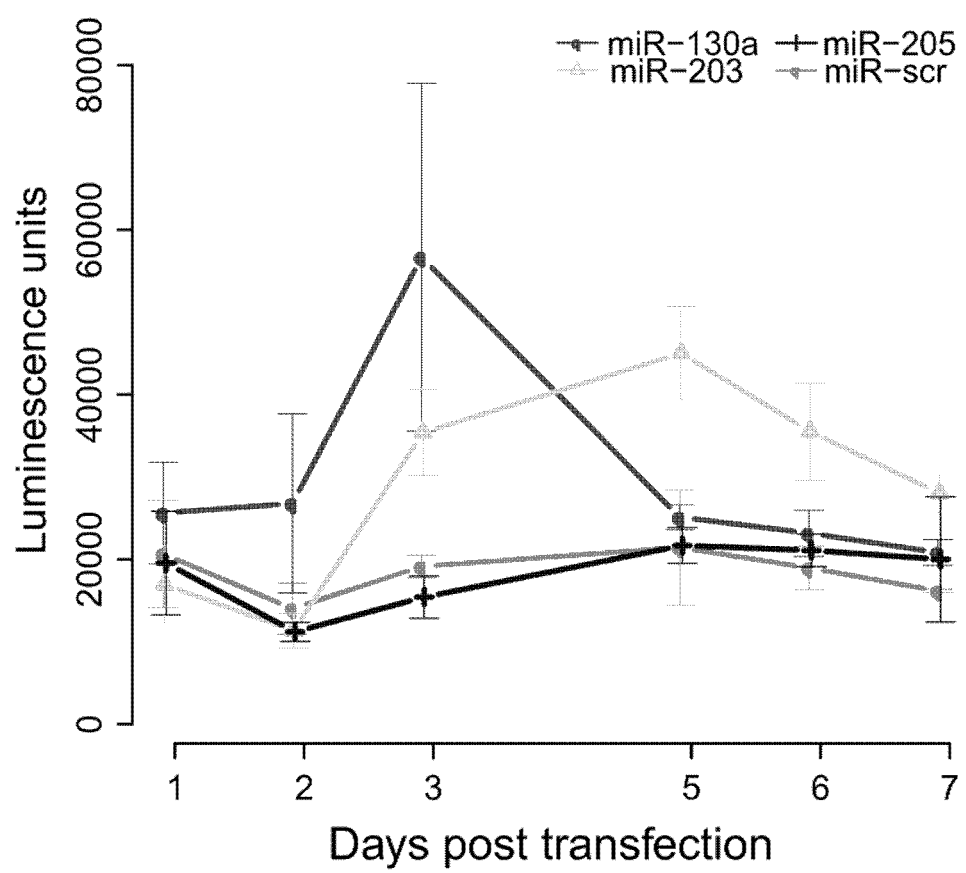
Figure 2D:
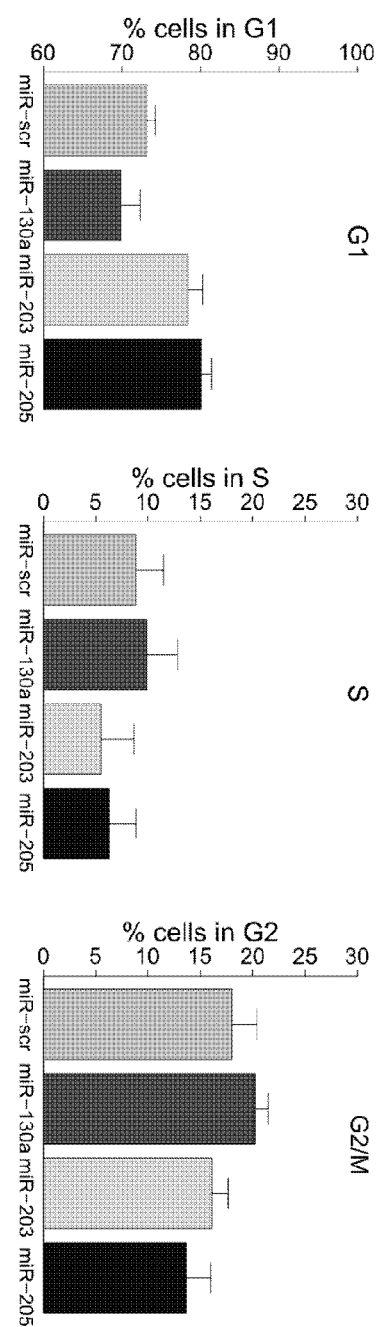
Figure 3A:
FIG. 3. Results of a first approach to identify targets of the miRNAs. (A) An exemplary gel for miR-130a is shown, and (B) the results of the first approach are shown in a summary.
Figure 3B:
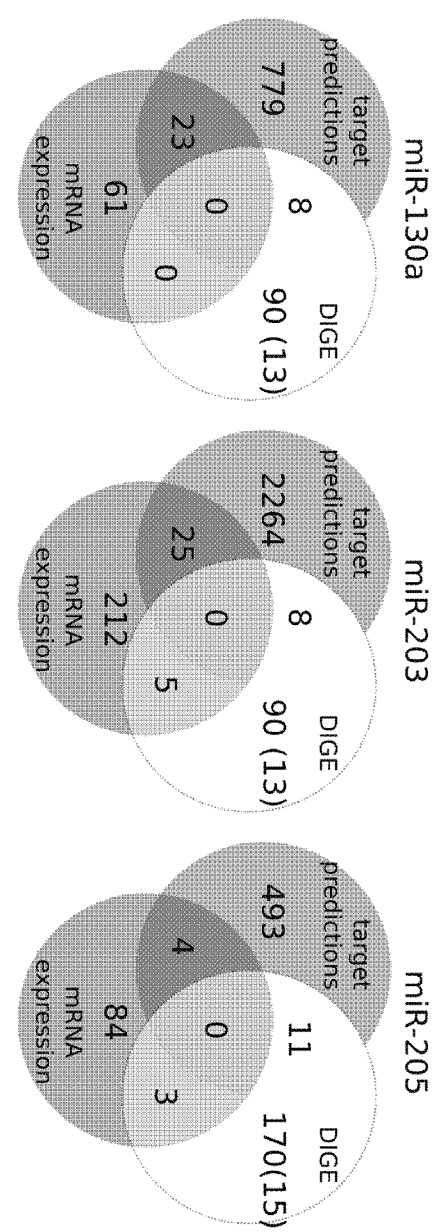

The inventors then determined whether the observed effects on cell numbers were due to cell cycle arrest or increased apoptosis. MiR-130a showed a strong apoptotic signal on day 3 ($p<0.05$) (FIG. 2C). MiR-203 induced an increase in apoptosis on day 3 ($p<5'10^{-3}$), peaking on day 5 ($p<0.01$) and continuing to day 6 (FIG. 2C). Cell cycle analysis on day 3 (see FIG. 2D) showed that miR-203 and miR-205 induced a significant increase ($p<0.01$) in the proportion of cells in G1 phase. Consistent with this increase, proportions in S and G2/M phases were reduced for miR-203 and miR-205 (FIG. 2D). Thus, miR-203 seems to cause both, apoptosis and cell cycle arrest, whereas miR-130a seems to induce only apoptosis and miR-205 selectively seems to cause cell cycle arrest.

Example 3

Approach 1: Target Candidates Identified Using 3 Different Approaches Include Known PCa Associated Genes Involved in AR Signaling To identify target genes responsible for the decrease in cell number and induction of apoptosis, the inventors in a first approach combined three different approaches. The miRecords database [34] was used to generate a list of mRNAs that were predicted by at least four out of 12 available prediction algorithms. This returned 779 predicted targets for miR-130a, 2264 for miR-203, and 493 for miR-205. The inventors also determined differential expression of mRNAs in response to miRNA overexpression in LNCaP cells using microarrays. Overexpression of miR-130a caused differential expression of 200 mRNAs (61 down, 139 up), miR-203 338 mRNAs (212 down, 126 up) and miR-205 144 mRNAs (84 down, 60 up) compared to overexpression of miR-scr at $p<=X$ (adjusted for multiple testing according to Benjamini and Hochberg[35]). Of the 61 mRNAs downregulated by miR-130a 24 are consensus predicted targets of this miRNA. One target, prosaposin, is known to be overexpressed in PCa and regulated by AR signaling [36,37]. For miR-203 27 of the downregulated RNAs are consensus predicted targets. Two of them, TRAP and NDRG3 are known to be overexpressed in PCa and regulated by AR signaling [38-40]. Overexpression of miR-203 also downregulates prostate specific antigen (PSA). Of 84 mRNAs downregulated by miR-205, four are consensus predicted targets. At the level of protein expression, the inventors used DIGE (differential in gel electrophoresis) to identify miRNA effects upon overexpression. DIGE experiments showed high reproducibility within the triplicates performed and revealed between 467 and 740 spots, depending on the miRNA overexpressed (see FIG. 4 for an exemplary gel). Differentially expressed proteins were identified by mass spectrometry. Out of the regulated proteins several were identified, that are reported to be connected to the androgen receptor pathway, among them PDIA3 and the ATP-dependent DNA helicase 2 subunit (targets for all three miRNAs). Further, CALR seem to be targets (miRNA203 and 205); PRDX1, PRDX2, PRDX6, CFL1, ANP32A, PARK7 (all miRNA130a), HYOU1 (miRNA 203) and PCNA (miRNA 205).

In summary, the combination of target predictions, transcriptomics and proteomics identifies several putative targets for these miRNAs that are known to be overexpressed in PCa and some of which have been reported to be regulated by AR signaling.

Example 4

Approach 2: miR-130a and miR-203 are Repressors of Androgen Signaling

Figure 4B:
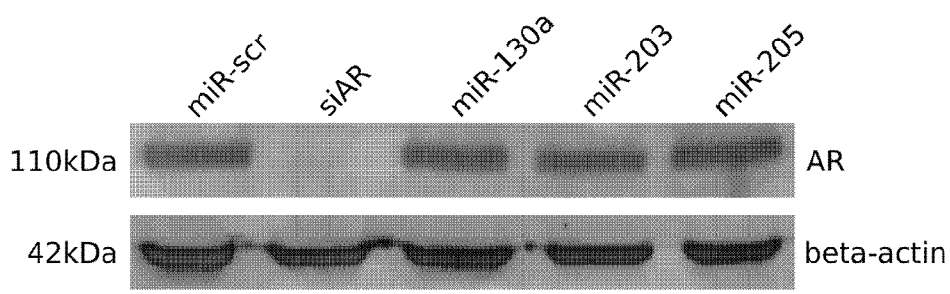

Target identification suggested a role for the miRNAs as suppressors of androgen receptor signaling transactivators. The inventors therefore studied AR signaling using a luciferase reporter system in LNCaP cells upon overexpression of miRNAs, miR-scr, and an siRNA against AR (siAR) as a positive control (FIG. 4). The reporter assay revealed a repressing effect of miR-203 on AR signaling (p<0.0025). Further, the combined overexpression of miR-130a and miR-205 and the triple overexpression reduced the level of AR signaling to that of siAR similar to the observations on cell numbers. To exclude that the observed effect is due to a direct targeting of AR mRNA by these miRNAs, the inventors studied AR protein expression under the same conditions as used for the reporter assay. While the AR siRNA strongly reduced AR expression 3 days post transfection overexpression of the miRNAs had no effect compared to miR-scr (FIG. 4B).

Example 5

Approach 3: Target Candidates Identified Upon miRNA Reconstitution Using Microarrays and Differential in Gel Electrophoresis Followed by MS To identify signaling pathways and molecular processes that may account for the observed effects on growth and survival, the inventors also performed mRNA and protein expression analyses upon miRNA reconstitution using microarrays and differential in gel electrophoresis followed by mass spectrometry (DIGE/MS), respectively. Between 580 (miR-130a: 228 down-, 352 upregulated) and 1055 (miR-203: 633 down-, 422 upregulated, miR-205: 436 down-, 273 upregulated) transcripts were differentially expressed upon miRNA reconstitution, with FDR<1e−3 according to Benjamini and Hochberg. For proteins, 114, 79, and 178 spots were significantly downregulated upon miR-130a, miR-203, and miR-205 reconstitution.

Figure 5A:
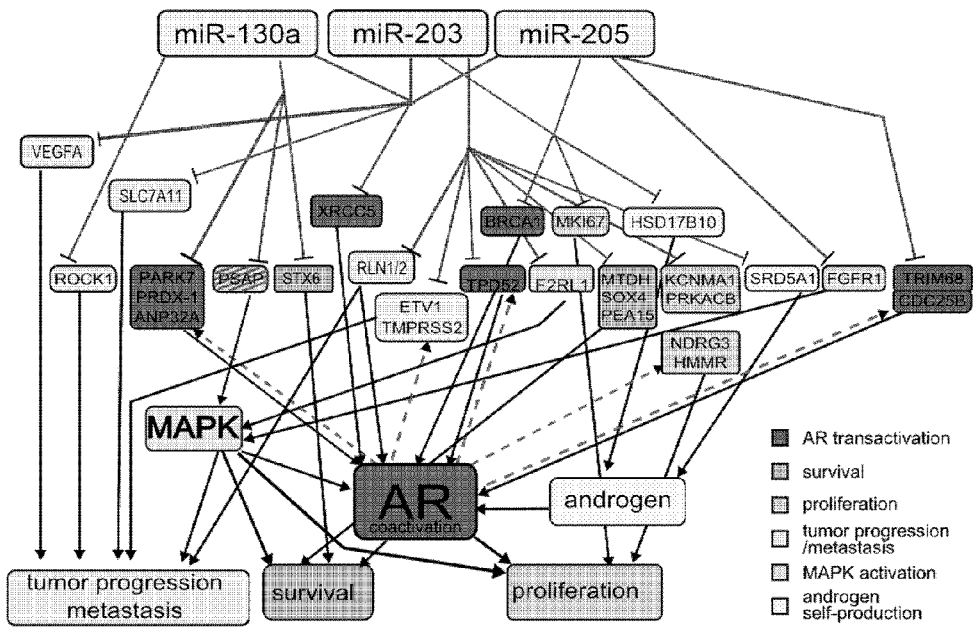
FIG. 5. Summary of gene products that are regulated upon miRNA reconstitution. (A) Summary of gene products that are significantly down-regulated upon miRNA reconstitution and which have been reported to be overexpressed in PCa in the literature and have been reported to interfere with PCa relevant pathways or processes. Red lines indicate repressive or negative regulatory effects, black lines stimulative or positive regulatory effects. Dashed purple lines indicated gene products that are known to be positively regulated by AR signaling. (B) Analogous representation of gene products which are upregulated upon miRNA reconstitution and have been found to be underexpressed in PCa.
Figure 5B:
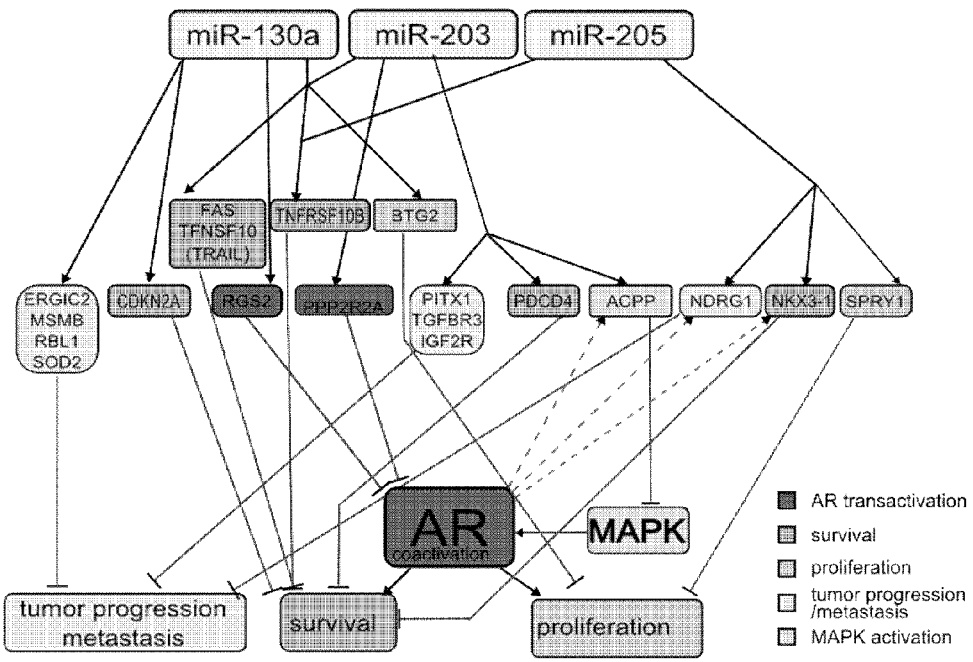

Many (miR-130a: 41 down-, 88 upregulated; miR-203: 129 down-, 77 upregulated; miR-205: 106 down-, 60 upregulated) of the identified differentially expressed transcripts have been associated with PCa in the literature. PCa-associated mRNAs are significantly enriched in the set of upregulated versus all other RNAs for miR-130a (p<$10^{-5}$) and miR-205 (p<0.01) and in the set of downregulated versus all other mRNAs for miR-203 (p<0.005) and miR-205 (p<$10^{-5}$). Several of these downregulated transcripts are known to be overexpressed in PCa, which corresponds well to the observed downregulation of the miRNAs in tumors (FIG. 5A). Likewise, several mRNAs known to be downregulated in PCa are upregulated upon miRNA reconstitution (FIG. 5B). Several downregulated transcripts are known AR coregulators, e.g. GTF2H1, PARK7 (for miR-130a), BRCA1 (for miR-203 and miR-205) and NCOA4 (for miR-205). Transcripts downregulated upon miR-205 reconstitution are significantly enriched for gene ontology terms associated with cell cycle, e.g. *DNA replication, M phase, and regulation of mitotic cell cycle*, with p-values <$10^{-12}$, $10^{-8}$, and $10^{-3}$ respectively. Thus, reconstitution of miR-130a, miR-203, and miR-205 suggests interference with known PCa-associated pathways, in particular AR signaling.

Example 6

Approach 4: Identification of Direct Targets

Figure 6A:
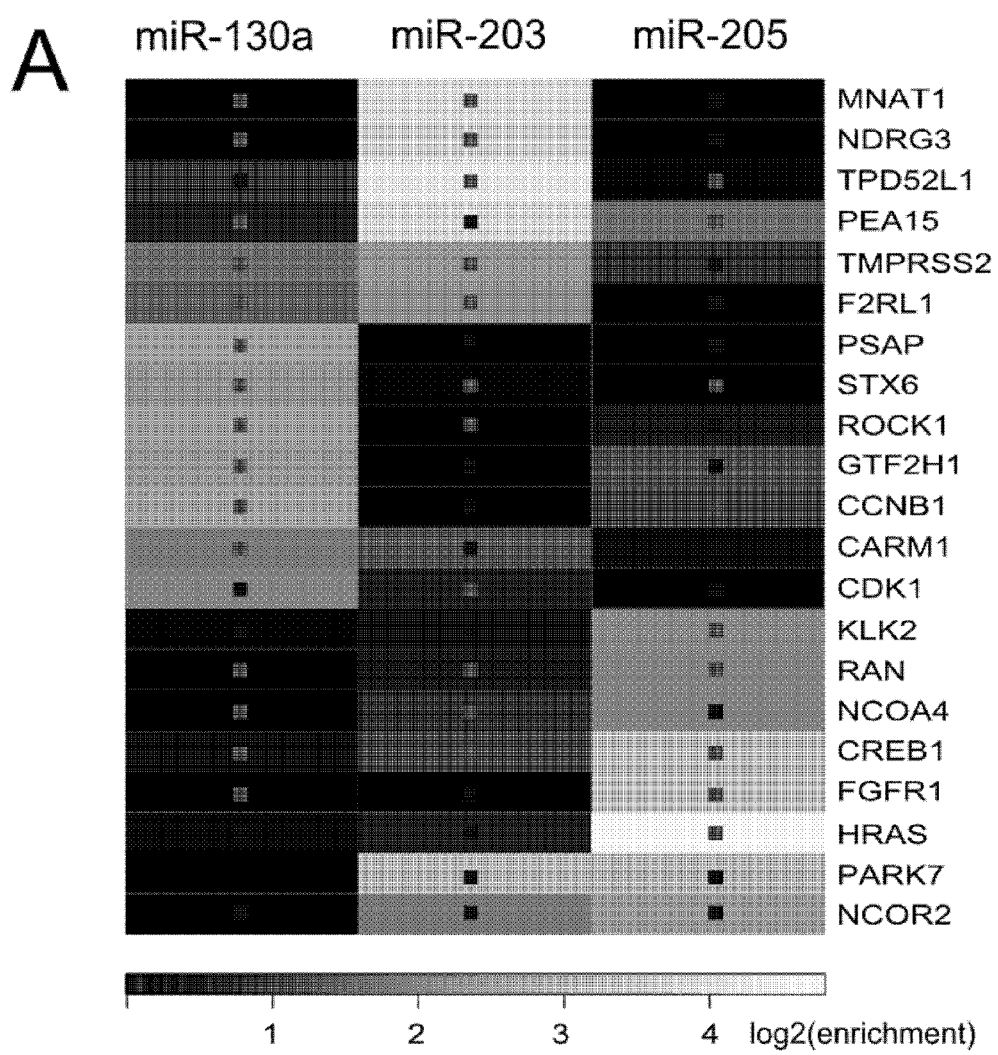
FIG. 6. MiRNAs target PCa associated genes and AR coregulators. (A) AGO2 bound RNA was co-immunoprecipitated from LNCaP cells transfected with miRNA or miR-scr and quantified using Affymetrix U133A microarrays. Expression signals of AGO2 bound RNA were normalized to total RNA preparations from the same cell population and enrichments of miRNA versus miR-scr transfected cells calculated. The heatmap displays log2(enrichment) of selected RNAs that have published relevance in PCa, AR, or MAPK signaling, are at least 4-fold enriched and total RNA normalized signals for miRNAs are significantly higher than for miR-scr at an FDR<0.01 (n=3). For simplicity, enrichments <1 are not shown. Targets that have been predicted for the respective miRNA by RNAhybrid only are indicated by blue squares. Red squares indicate a prediction by any of the more specific algorithms contained in the miRecords database Xiao et al. 2009. (B) Venn diagram showing the overlap of AGO2-enriched transcripts for miR-130a, miR-203, and miR-205, with an enrichment >=4 and FDR<0.01. (C) To validate the array data from the AGO2-RIP experiment, four selected transcripts for each miRNA were analyzed using RT-qPCR and compared to the array data. Bars represent mean+Stdv (n=3). (D) 3'UTR reporter assay of LNCaP cells transfected with p2FP-RNAi vector that contains the full length 3'UTR or a major part of it downstream of GFP, cotransfected with miRNA or miR-scr vector. GFP fluorescence detected 48 h post transfection was normalized to JRed fluorescence. The ratio of miRNA versus miR-scr normalized fluorescence is shown. * indicates significant downregulation with p<0.05, ** with p<0.01 (n=3). (E) Western Blot analysis of H-Ras expression upon miRNA or miR-scr reconstitution 48 h post-transfection. β-actin was measured as a normalization control.
Figure 6B:
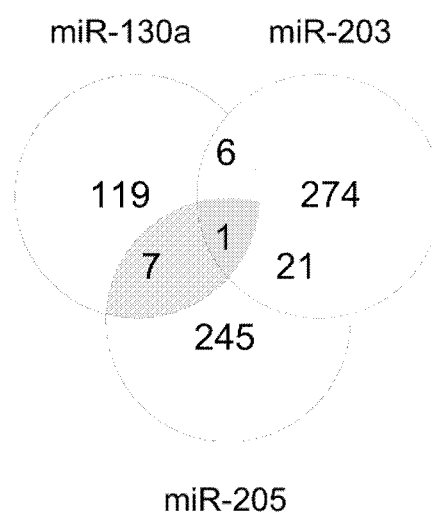

For identifying the direct targets of miR-130a, miR-203, and miR-205, the inventors performed AGO2-RNA co-immunoprecipitation (Beitzinger et al. 2007) upon miRNA reconstitution and analyzed AGO2-bound mRNAs using Affymetrix microarrays. Relative levels of AGO2 bound versus total RNA expression were compared between miRNA reconstituted and miR-scr transfected samples. The inventors identified 133 transcripts for miR-130a, 292 transcripts for miR-203 and 274 transcripts for miR-205. Despite the large number of AGO2-enriched mRNAs, the overlap in mRNAs between the three miRNA reconstitution experiments is low, indicating a high specificity of this procedure (FIGS. 6A and 6B).

Figure 6C:
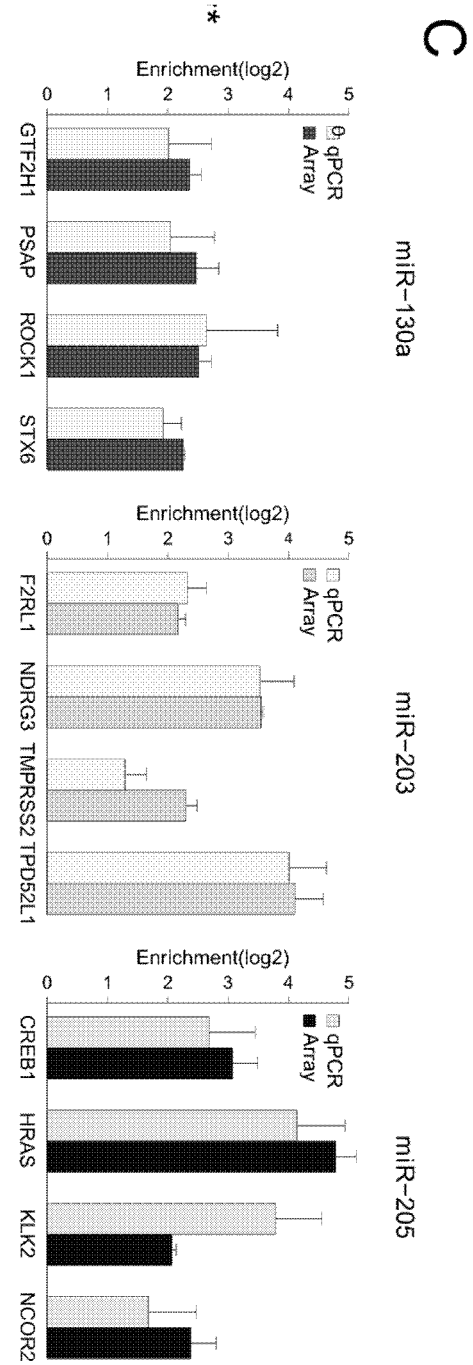
Figure 6D:
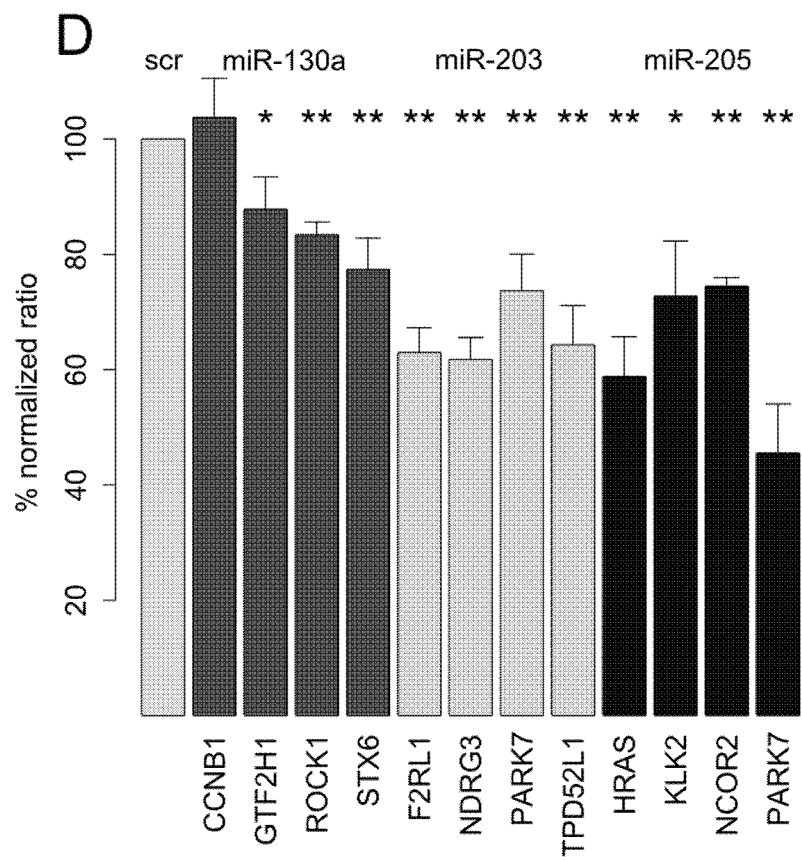

Four AGO2-enriched transcripts for each miRNA were chosen for validation using RT-qPCR and displayed comparable levels of enrichment (FIG. 6C). Additionally, the inventors selected 4 mRNAs per miRNA with (i) strong AGO2 enrichment and p-value, (ii) at least three predicted binding sites of the respective miRNA in their 3'UTR and (iii) a 3'UTR length <3000 for 3'UTR reporter assays. The inventors observed significantly reduced fluorescence (p<0.05) upon miRNA reconstitution versus miR-scr transfection, which further corroborates direct targeting of these mRNAs (see FIG. 6D).

A prominent fraction of AGO2-enriched transcripts again is known to be PCa-associated (21 for miR-130a and 38 for miR-203 and miR-205). Several AR coregulators are found among the enriched mRNAs, like PSAP and GTF2H1 for miR-130a, MNAT1 for miR-203, PARK7 for miR-203 and miR-205 or RAN for miR-205.

Figure 6E:
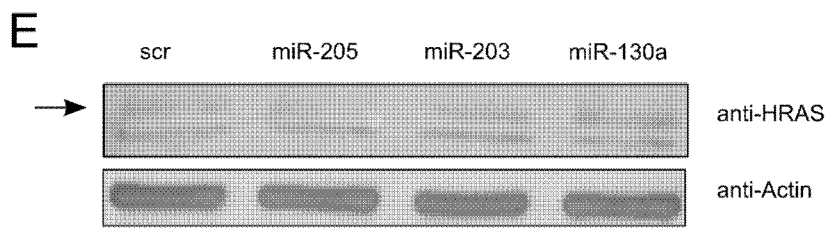

For all three microRNAs, components of the MAPK signaling pathway, a major oncogenic and AR cross-talk pathway in PCa, were found to be AGO2 enriched, including PSAP for miR-130a, PAR2 for miR-203, and FGFR1, KLK-2 and H-Ras for miR-205. Targeting of H-Ras by miR-205 was further corroborated by a 3'UTR reporter assay (FIG. 6D) and Western Blot analysis (FIG. 6E).

In summary, all three miRNAs seem to interfere with AR and MAPK signaling by directly targeting different components of both signaling pathways.

Example 7

Effect of the miRNAs on MAPK Signaling

Figure 7A:
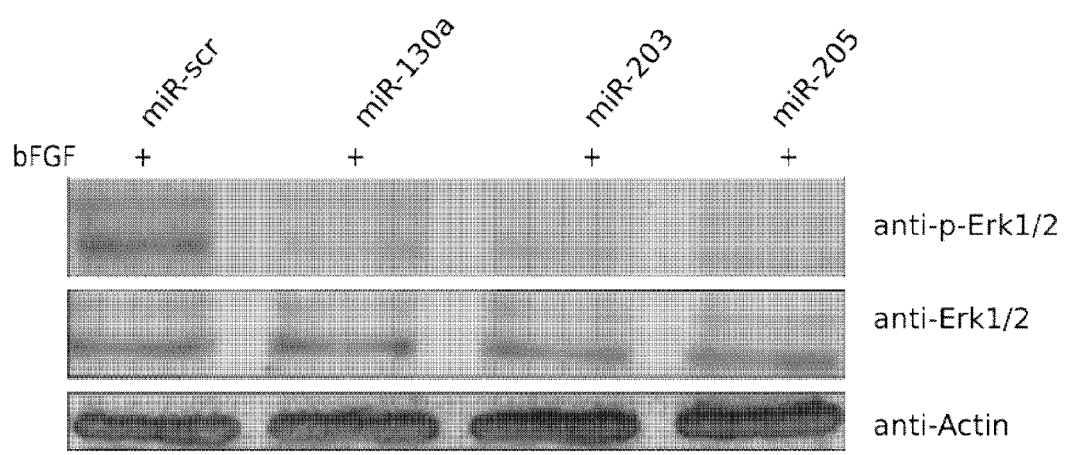
FIG. 7. MiR-130a, miR-203, and miR-205 interfere with MAPK signaling. (A) Western Blot analysis of Erk1/2 phosphorylation in LNCaP cells after 15 min stimulation with 50 ng/ml bFGF 48 h post-transfection with the different miRNAs or miR-scr. An antibody against Erk1/2 was used as a control, that the miRNAs do not alter total protein levels. β-actin was measured as a normalization control. (B) A sketch of the model of the inventors describing the interference of miR-130a, miR-203 and miR-205 with AR and MAPK signaling at different levels.
Figure 7B:
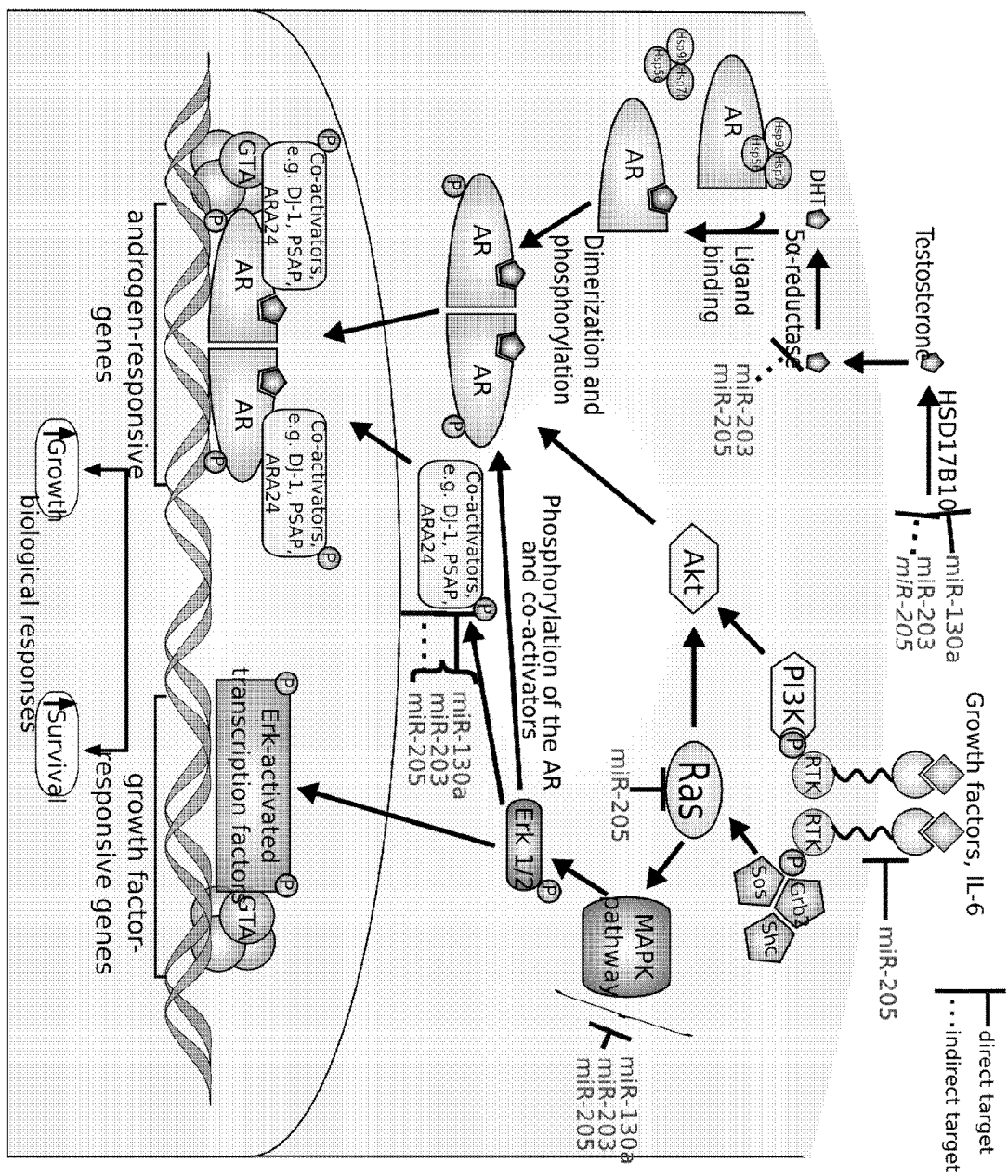

Target identification also indicated interference of all three miRNAs with the MAPK pathway. The inventors therefore analyzed the phosphorylation status of Erk1/2, the effector kinase of the MAPK pathway using Western Blot. After 15 min. of stimulation with 50 ng/ml bFGF (a growth factor and activator of MAPK signaling), levels of phosphorylated Erk1/2 were downmodulated by all three microRNAs compared to miR-scr, while total amounts of Erk1/2 remained unchanged (FIG. 7A). In summary, miR-130a, miR-203, and miR-205 thus seem to repress AR and MAPK signaling by targeting different components of these signaling pathways.

Materials and Methods

1. Tissue Collection

Use of patient materials was approved by the local ethical committee of the Radboud University Nijmegen Medical Centre. Upon radical prostatectomy, transurethral resection of the prostate, or lymph node dissection, specimens were snap frozen in liquid nitrogen. Benign, benign hyperplastic and tumor prostatic tissues were evaluated by H&E staining Tissues were selected for purity of benign or cancer cells and processed by step sectioning.

The following tumor samples were used:

|    | Sample.     | GS    | C | remarks                          |
|----|-------------|-------|---|----------------------------------|
| 13 | Prostate 987 |      | N | NP/BPH 60%, stroma 40%           |
| 14 | Prostate 988 |      | N | NP 40%, stroma 60%               |
| 17 | Prostate 969 |      | N | BPH 100%                         |
| 18 | Prostate 974 |      | N | NP 40%, stroma 60%               |
| 19 | Prostate 990 |      | N | NP 50%, stroma 50%               |
| 20 | NPr 994     |      | N | NPr, atrophy 60%, stroma 60%     |
| 15 | Prostate 968 |      | S | stroma 100%                      |
| 16 | Prostate 971 |      | S | stroma 100%                      |
| 3  | Pca 1006    | 4.00  | L | PCa, GG 2 + 2 40%, AAH 45%       |
| 5  | Pca 1010    | 5.00  | L | PCa, GG 3 + 2 80%, NP 10%, stroma 10% |
| 1  | Pca 981     | 6.00  | L | PCa, GG 3 + 3 90%, NP 5%, stroma 5% |
| 2  | Pca 1005    | 6.00  | L | PCa, GG 3 + 3 80%, NP 10%, stroma 10% |
| 4  | Pca 1007    | 6.00  | L | PCa, GG 3 + 3 75%, NP 15%, stroma 10% |
| 6  | Pca 978     | 8.00  | H | PCa, GG 3 + 5 95%, stroma 5%     |
| 8  | Pca 986     | 8.00  | H | PCa, GG 5 + 3 55%, NP 15%, PIN 15% |
| 10 | Pca 993     | 8.00  | H | PCa, GG 5 + 3 90%, NP 5%, stroma 5% |
| 11 | Pca 992     | 8.00  | H | Pca, GG 3 + 5 90%, NP 5%, stroma 5% |
| 9  | Pca 989     | 9.00  | H | PCa, GG 5 + 4 90%, NP 5%, stroma 5% |
| 7  | Pca 983     | 10.00 | H | PCa, GG 5 + 5 70%, NP 10%, stroma 20% |
| 21 | Rec-PCa 927 |      | R | recurrence Pca, 90% undifferentiated PCa |
| 22 | Rec-PCa 929 |      | R | recurrence Pca, 90% poorly diff. PCa |
| 23 | Rec-PCa 998 |      | R | 70% poorly diff. Pca, 30% stroma |

2. Cell Culture

Cells were grown in medium to confluency (LNCaP cells: RPMI 1640 medium with L-glutamine (PAA) (10% FCS (Biochrom), 100 Units/ml penicillin, 100 μg/ml streptomycin (PAA) and 10 mM HEPES buffer (Biochrom), PC-3 and Du-145 cells: DMEM/F-12 medium with L-glutamine (PAA) (10% FCS (Biochrom), 100 Units/ml penicillin, 100 n/ml streptomycin (PAA)), and RWPE-1 cells: Keratinocyte-Serum free medium (Gibco-BRL) (5 ng/ml human recombinant EGF and 0.05 mg/ml bovine pituary extract (Gibco-BRL))). Cells were transfected using the Nucleofector 2 Technology (Amaxa) according to the instructions. For miRNA reconstitution 2.5 μg plasmid DNA for each miRNA was used. 'Single' or 'double' transfections were filled with corresponding amounts of the empty pSuper vector. To enhance transfection efficiency cells were electroporated twice.

3. miRNA Expression Constructs

To generate microRNA expression plasmids, the pSuper vector system (Oligoengine) was used according to the manufacturers protocol. Oligos containing the mature miRNA sequence for miR-130a, miR-203, miR-205 and a scr-miR as control were obtained from Metabion. The following primer sets were used to generate the pSuper-miR vectors:

```
miR-130a fwd
                                          (SEQ ID No: 10)
5'GATCCCCcagtgcaatgttaaaagggcatTTCAAGAGAatgccctt ttaacattgcactgTTTTTA, miR-130a rev
                                          (SEQ ID No: 11)
5'AGCTTAAAAAcagtgcaatgttaaaagggcatTCTCTTGAAatgcc cttttaacattgcactgGGG, miR-203 fwd
                                          (SEQ ID No: 12)
5' GATCCCCgtgaaatgtttaggaccactagTTCAAGAGActagtgg tcctaaacatttcacTTTTTA, miR-203 rev
                                          (SEQ ID No: 13)
5'AGCTTAAAAAgtgaaatgtttaggaccactagTCTCTTGAActagt ggtcctaaacatttcacGGG, miR-205 fwd
                                          (SEQ ID No: 14)
5'GATCCCCtccttcattccaccggagtctgTTCAAGAGAcagactcc ggtggaatgaaggaTTTTTA miR-205 rev
                                          (SEQ ID No: 15)
5AGCTTAAAAAtccttcattccaccggagtctgTCTCTTGAAcagact ccggtggaatgaaggaGGG miR-scr fwd
                                          (SEQ ID No: 16)
5' GATCCCCccaacaaccgttctcagaaTTCAAGAGAttctgagaac ggttgttggTTTTTA,
```

```
miR-scr rev
                                       (SEQ ID No: 17)
5'AGCTTAAAAAccaacaaccgttctcagaaTCTCTTGAAttctgaga acggttgttggGGG
```

4. RNA Extraction and Quality Control

Total RNA was extracted using TRIZOL™ reagent according to the manufacturer's instructions (Invitrogen). Small RNAs <200 nt were isolated out of total RNA using the PureLink™ miRNA Isolation Kit (Invitrogen). RNA integrity for each sample was confirmed with the total RNA Nano Assay and the Agilent 2100 Bioanalyzer (Agilent Technologies).

5. Quantitative Real Time PCT 50 ng of total RNA was reverse transcribed using mature miRNA-specific stemloop primers with the TaqMan miRNA Reverse Transcription kit (Applied Biosystems) following the manufacturer's directions. miRNA expression analysis was performed using TaqMan Universal Mastermix and TaqMan miRNA assay according to the manufacturer's instructions (Applied Biosystems). All miRNA quantification data were normalized to U48 small nucleolar RNA.

For validation of AGO2-enriched transcripts RNA was reverse transcribed using the High Capacity cDNA Reverse transcription kit (Applied Biosystems) according to the manufacturer's instructions. qPCR was performed using FAST SYBR green (Applied Biosystems) with the following primers:

```
F2RL1 fw:
                                       (SEQ ID No: 25)
gctctcctttt gccgaagtgt F2RL1 rev:
                                       (SEQ ID No: 26)
ttgaacttga agagtaagag ctggatt GTF2H1 fw:
                                       (SEQ ID No: 27)
agcacaaatt tggtaagtca catagaa GTF2H1 rev:
                                       (SEQ ID No: 28)
catggccacc tcacgttttc HRAS fw:
                                       (SEQ ID No: 29)
gagcagatca aacgggtgaa g HRAS rev:
                                       (SEQ ID No: 30)
ctgagcctgc cgagattcc KLK2 fw:
                                       (SEQ ID No: 31)
ttcatcacaa atcccatctt tagc KLK2 rev:
                                       (SEQ ID No: 32)
gacatttgat tccttggcat gtt NCOR2 fw:
                                       (SEQ ID No: 33)
aaggaggagc tgatccagaa cat NCOR2 rev:
                                       (SEQ ID No: 34)
agccttcttc cggttctcgt PCA3 fw:
                                       (SEQ ID No: 35)
ccgagggaga ccaggaagat PCA3 rev:
                                       (SEQ ID No: 36)
atcgatgacc caagatggcg PSA fw:
                                       (SEQ ID No: 37)
accagaggag ttcttgaccc caaa PSA rev:
                                       (SEQ ID No: 38)
ccccagaatc acccgagcag PSAP fw:
                                       (SEQ ID No: 39)
ttggtggaac atgtcaagg PSAP rev:
                                       (SEQ ID No: 40)
cttgggttgc tgatcctg ROCK1 fw:
                                       (SEQ ID No: 41)
tgctgctgtt agcatgttct ca ROCK1 rev:
                                       (SEQ ID No: 42)
ggaaagactg atttgcagtg gat Stx6 fw:
                                       (SEQ ID No: 43)
ctgtgtggca aatgcaggtt Stx6 rev:
                                       (SEQ ID No: 44)
cagagaataa tgggcaagtt acca TMPRSS2 fw:
                                       (SEQ ID No: 45)
gagtgcgact cctcggtacc t TMPRSS2 rev:
                                       (SEQ ID No: 46)
agaggcgaac acaccgattc beta actin fw:
                                       (SEQ ID No: 47)
cctggcaccc agcacaat beta actin rev:
                                       (SEQ ID No: 48)
gccgatccac acggagtact
```

6. Cell Counting, Apoptosis Assay and Cell Cycle Analysis

Transfected LNCaP cells were harvested after 24 h, 3, 5, 6+7 days and cell numbers were determined using a Neubauer's chamber. Each sample was counted 4 times. For apoptosis analysis the Caspase-Glo 3/7 Assay (Promega) was used according to the protocol. Luciferase signal measurements were done using the Tecan infinite 200 system.

Cell cycle profiles were assessed by flow cytometry using Propidium Iodide staining (PI) to measure DNA content on a FC-500 cytometer (Beckman Coulter). Histograms were fitted using Multicycle AV (Phoenix Flow Systems) with FACS Express V3 software (deNovo Software).

7. Western Blot Analysis

Whole cell protein was isolated using TRIZOL™ reagent according to the manufacturer's instructions (Invitrogen). Antibodies used for Western blotting were AR (Cell signaling technology), H-Ras (Santa Cruz biotechnologies), p-Erk1/2 (Cell signaling technology), Erk1/2 (Cell signaling technology), Actin (MP Immuno). The secondary horseradish peroxidase conjugated antibodies (anti-mouse IgG, anti-rabbit IgG, Cell signaling technology) were detected using the ECL Plus Western blotting detection reagents (Amersham Biosciences).

8. Androgen Reporter Assay

A HSV-TK promoter was amplified from the psiCheck2™ vector (Promega) and cloned into the BglII and HindIII sites of the MCS of the pGL-4.1 vector (Promega), now termed pGL4.1-TK. An androgen responsive element (ARE) described in Gavrielides et al. 2006 was amplified from genomic DNA and cloned between the HSV-TK promoter and the luciferase open reading frame using the KpnI and XhoI restriction sites in the MCS of the pGL-4.1-TK vector. Primer sequences were as follows:

```
HSV-TK fwd
                                   (SEQ ID No: 18)
5'GCGAGATCTAAATGAGTCTTCGG HSV-TK rev
                                   (SEQ ID No: 19)
5'ATTAAGCTTTTAAGCGGGTCGC AREfwd
                                   (SEQ ID No: 20)
5'ATAGGTACCTCCATCCAAGGAATG ARE rev
                                   (SEQ ID No: 21)
5' ATACTCGAGGCCTCAGGGAAG
```

LNCaP cells were cotransfected with the reporter and the miR-expression vector or 1 μM siAR oligos (ON-TARGET plus Smart pool siRNA, Dharmacon) and the pMIR-REPORT beta-gal Control Plasmid™ for normalization. Firefly luciferase activities were measured using the Bright-Glo Luciferase Assay system (Promega), and beta-gal activities using the Beta-Glo Assay system (Promega) 48 h after transfection on a Tecan infinite M200 plate reader.

9. miRNA Profiling miRNA analysis in cell lines was performed using the CombiMatrix 4×2k human microRNA microarray. 2 μg microRNA was Cy-5-labeled using the Minis Bio Label IT miRNA Labeling Kit according to the manufacturer's protocol. Hybridization and scanning was performed following the manufacturer's instructions (CombiMatrix). Arrays were run in triplicate for each cell line. Arrays were scanned using a GenePix 4200 Scanner and the GenePix Pro 6.1 Software (Molecular Devices) with the following settings: laser power: 40%, PMT: 500, resolution: 5 μm, Focus: 85 μm.

Differentially expressed miRNAs were identified by statistical assessment using R and BioConductor (www.bioconductor.org). Expression levels were quantile normalized (Bolstad et al. 2003) and a linear model was fitted using the Limma package. Reliable variance estimations were obtained by empirical Bayes moderated t-statistics. False discovery rate was controlled by Benjamini-Hochberg adjustment (Benjamini and Hochberg 1995).

10. Gene Expression Profiling

RNA was isolated from LNCaP cells 48 h post-transfection. 2 μg RNA were analyzed on Affymetrix GeneChip Human Genome U133A 2.0 Arrays according to the manufacturer's protocol. Arrays were run in triplicate. Differentially expressed mRNAs were identified by statistical analysis using R and BioConductor using the same procedures as described for miRNAs. Quality assessment of arrays was performed as described in the standard protocol. False discovery rate was controlled by Benjamini-Hochberg adjustment (Benjamini and Hochberg 1995). G0 term enrichment was performed using R library GOstats (Falcon and Gentleman 2007), excluding G0 terms with "IEA" evidence code.

11. Association with PCa in the Literature

PubMed abstracts matching the search query "prostate AND (cancer OR carcinoma)" were downloaded (version: April 2010) and assigned to transcripts on Affymetrix GeneChip Human Genome U133A 2.0 Arrays using the gene2pubmed table (ftp://ftp.ncbi.nlm.nih.gov/gene/DATA/, April 2010). A 2-sample test for testing the null hypothesis that the proportions of PCa associated transcripts is the same for significantly down-, or upregulated transcripts compared to non-regulated transcripts.

12. DIGE Quantitative Analysis

Protein extraction and 2D gel analysis was performed as described previously (Mörbt et al. 2009). Labeling of proteins was performed according to the manufacturer's recommendations (GE healthcare) and 2D gel analysis following (Berth et al. 2007). Scanned gel pictures were analyzed in Delta 2D version 3.6 software (Decodon). Detected spots were manually edited and transferred to all gel pictures. Spot volumes (integrated staining intensity) were normalized to the total protein amount on each gel. Relative volumes of spots were determined in comparison to the same spot intensity in the internal standard channel on each gel. Mean relative volumes of identical spots on triplicate gels were calculated and divided by the mean relative volume of the corresponding spots in the controls (3 replicates), yielding the expression ratio. Differentially expressed proteins were identified using the following parameters: expression ratio <0.75 or >1.3 and a p-value of p<0.05, as obtained by the software integrated Student's t-test. Tryptic digestion was carried out with porcine trypsin as described by (Benndorf et al. 2007). The extracted peptides were either spotted on a MALDI anchor chip target and analyzed using a Bruker Ultraflex III according to (Georgieva et al. 2008) or were separated by reversed-phase nano-LC (LC1100 series, Agilent Technologies; column: Zorbax 300SB-C18, 3.5 μm, 150×0.075 mm; eluent: 0.1% formic acid, 0-60% ACN) and analyzed by tandem mass spectrometry (LC/MSD TRAP XCT mass spectrometer, Agilent Technologies) as described elsewhere (Jehmlich et al. 2008).

13. AGO2-RNA Immunoprecipitation

AGO2 RNA co-immunoprecipitation (AGO2 co-IP) was performed according to (Beitzinger et al. 2007) 48 h post-transfection of the respective miRNAs or miR-scr, using AG02-1 11A antibody (Ascenion). In addition, total RNA of transfected cells was isolated. Isolated AGO2-bound RNA and total RNA, respectively, were quantified using Affymetrix U133A 2.0 array as described above. Experiments were performed in biological triplicates. After GCRMA preprocessing using R and BioConductor (www.bioconductor.org), expression values of the AGO2 co-IP were divided by the corresponding total RNA data, for miRNA and miR-scr transfected cells, respectively. Enrichments and t-test p-values were calculated comparing miRNA to miR-scr transfected samples. Finally, FDR was controlled by Benjamini-Hochberg adjustment (Benjamini and Hochberg 1995).

14. 3'UTR Reporter Assay

3'UTRs of CCNB1, F2RL1, GTF2H1, HRAS, NCOR2, NDRG3, PARK7, ROCK1, and TPD52L1, respectively shortened 3'UTRs for KLK2 and STX6, were amplified by PCR and cloned into the MCS of the p2FP-RNAi vector (Evrogen). LNCaP cells were co-transfected with the respective p2FP vector and miRNA or miR-scr expression vector. Fluorescence signals were measured 48 h post-transfection on a Tecan infinite 1000 system (TurboGFP $1_{ex}$ 482 nm; $1_{em}$ 538 nm, JRed $1_{ex}$ 546 nm; $1_{em}$ 607 nm). Relative fluorescence was calculated as the ratio of normalized mean fluorescence of miRNA versus scramble treated samples.

15. Statistical Testing

For analysis of cell numbers, apoptosis induction, cell cycle and AR reporter assays, normality of data was checked by normal probability plots. Equal variances between populations could not be ensured. A one-tailed Welch Two Sample t-test was used for testing the null hypothesis that population means are less (cell cycle, greater) than corresponding means of miR-scr. For assessing differential expression in patient data ANOVA was used. In all plots error bars indicate standard deviations. For statistical procedures involved in microarray analysis refer to the specific subsections.

References

[1] David P Bartel. Micrornas: genomics, biogenesis, mechanism, and function. Cell, 116(2):281-297, January 2004.

[2] Ana Eulalio, Eric Huntzinger, and Elisa Izaurralde. Getting to the root of mirna-mediated gene silencing. Cell, 132(1):9-14, January 2008.

[3] Witold Filipowicz, Suvendra N Bhattacharyya, and Nahum Sonenberg. Mechanisms of post-transcriptional regulation by micrornas: are the answers in sight? Nat Rev Genet, 9(2):102-114, February 2008.

[4] Ana Eulalio, Eric Huntzinger, Tadashi Nishihara, Jan Rehwinkel, Maria Fauser, and Elisa Izaurralde. Deadenylation is a widespread effect of mirna regulation. RNA, 15(1):21-32, January 2009.

[5] Benjamin P Lewis, Christopher B Burge, and David P Bartel. Conserved seed pairing, often flanked by adenosines, indicates that thousands of human genes are microrna targets. Cell, 120(1):15-20, January 2005.

[6] Chang-Zheng Chen. Micrornas as oncogenes and tumor suppressors. N Engl J Med, 353(17):1768-1771, October 2005.

[7] Scott M Hammond. Micrornas as tumor suppressors. Nat Genet, 39(5):582-583, May 2007.

[8] Scott M Hammond. Micrornas as oncogenes. Curr Opin Genet Dev, 16(1):4-9, February 2006.

[9] Petra H°a°ag, Jasmin Bektic, Georg Bartsch, Helmut Klocker, and Iris E Eder. Androgen receptor down regulation by small interference rna induces cell growth inhibition in androgen sensitive as well as in androgen independent prostate cancer cells. J Steroid Biochem Mol Biol, 96(3-4):251-258, August 2005.

[10] D. F. Amanatullah, A. T. Reutens, B. T. Zafonte, M. Fu, S. Mani, and R. G. Pestell. Cell-cycle dysregulation and the molecular mechanisms of prostate cancer. Front Biosci, 5:D372-D390, April 2000.

[11] Prostate cancer: Risk factors and prevention. www.cancer.org, 2006.

[12] Joanne Edwards and John M S Bartlett. The androgen receptor and signal-transduction pathways in hormone-refractory prostate cancer. part 1: Modifications to the androgen receptor. BJU Int, 95(9):1320-1326, June 2005.

[13] C. Huggins. Endocrine-induced regression of cancers. Cancer Res, 27(11):1925-1930, November 1967.

[14] C. Huggins and C. V. Hodges. Studies on prostatic cancer. i. the effect of castration, of estrogen and androgen injection on serum phosphatases in metastatic carcinoma of the prostate. CA Cancer J Clin, 22(4):232-240, 1972.

[15] H. Saitoh, M. Hida, T. Shimbo, K. Nakamura, J. Yamagata, and T. Satoh. Metastatic patterns of prostatic cancer. correlation between sites and number of organs involved. Cancer, 54(12):3078-3084, December 1984.

[16] J. T. Grayhack, T. C. Keeler, and J. M. Kozlowski. Carcinoma of the prostate. hormonal therapy. Cancer, 60(3 Suppl):589-601, August 1987.

[17] M. Harada, M. Iida, M. Yamaguchi, and K. Shida. Analysis of bone metastasis of prostatic adenocarcinoma in 137 autopsy cases. Adv Exp Med Biol, 324:173-182, 1992.

[18] L. Bubendorf, A. Schöpfer, U. Wagner, G. Sauter, H. Moch, N. Willi, T. C. Gasser, and M. J. Mihatsch. Metastatic patterns of prostate cancer: an autopsy study of 1,589 patients. Hum Pathol, 31(5):578-583, May 2000.

[19] Rajal B Shah, Rohit Mehra, Arul M Chinnaiyan, Ronglai Shen, Debashis Ghosh, Ming Zhou, Gary R Macvicar, Soorynarayana Varambally, Jason Harwood, Tarek A Bismar, Robert Kim, Mark A Rubin, and Kenneth J Pienta. Androgen-independent prostate cancer is a heterogeneous group of diseases: lessons from a rapid autopsy program. Cancer Res, 64(24):9209-9216, December 2004.

[20] Martine P Roudier, Lawrence D True, Celestia S Higano, Hubert Vesselle, William Ellis, Paul Lange, and Robert L Vessella. Phenotypic heterogeneity of end-stage prostate carcinoma metastatic to bone. Hum Pathol, 34(7):646-653, July 2003.

[21] Michael D Mattie, Christopher C Benz, Jessica Bowers, Kelly Sensinger, Linda Wong, Gary K Scott, Vita Fedele, David Ginzinger, Robert Getts, and Chris Haqq. Optimized high-throughput microrna expression profiling provides novel biomarker assessment of clinical prostate and breast cancer biopsies. Mol Cancer, 5:24, 2006.

[22] Kati P Porkka, Minja J Pfeiffer, Kati K Waltering, Robert L Vessella, Teuvo L J Tammela, and Tapio Visakorpi. Microrna expression profiling in prostate cancer. Cancer Res, 67(13):6130-6135, July 2007.

[23] Stefan Ambs, Robyn L Prueitt, Ming Yi, Robert S Hudson, Tiffany M Howe, Fabio Petrocca, Tiffany A Wallace, Chang-Gong Liu, Stefano Volinia, George A Calin, Harris G Yfantis, Robert M Stephens, and Carlo M Croce. Genomic profiling of microrna and messenger rna reveals deregulated microrna expression in prostate cancer. Cancer Res, 68(15):6162-6170, August 2008.

[24] Robyn L Prueitt, Ming Yi, Robert S Hudson, Tiffany A Wallace, Tiffany M Howe, Harris G Yfantis, Dong H Lee, Robert M Stephens, Chang-Gong Liu, George A Calin, Carlo M Croce, and Stefan Ambs. Expression of micrornas and protein-coding genes associated with perineural invasion in prostate cancer. Prostate, 68(11):1152-1164, August 2008.

[25] M. Ozen, C. J. Creighton, M. Ozdemir, and M. Ittmann. Widespread deregulation of microrna expression in human prostate cancer. Oncogene, 27(12):1788-1793, March 2008.

[26] Silvia Galardi, Neri Mercatelli, Ezio Giorda, Simone Massalini, Giovanni Vanni Frajese, Silvia Anna Clafr, and Maria Giulia Farace. mir-221 and mir-222 expression affects the proliferation potential of human prostate carcinoma cell lines by targeting p27kip1. J Biol Chem, 282(32):23716-23724, August 2007.

[27] Neri Mercatelli, Valeria Coppola, Desir'e Bonci, Francesca Miele, Arianna Costantini, Marco Guadagnoli, Elena Bonanno, Giovanni Muto, Giovanni Vanni Frajese, Ruggero De Maria, Luigi Giusto Spagnoli, Maria Giulia Farace, and Silvia Anna Clafré. The inhibition of the highly expressed mir-221 and mir-222 impairs the growth of prostate carcinoma xenografts in mice. PLoS ONE, 3(12): e4029, 2008.

[28] Tong Sun, Qianben Wang, Steven Balk, Myles Brown, Gwo-Shu Mary Lee, and Philip Kantoff. The role of microrna-221 and microrna-222 in androgenindependent prostate cancer cell lines. Cancer Res, 69(8):3356-3363, April 2009.

[29] Xu-Bao Shi, Lingru Xue, Joy Yang, Ai-Hong Ma, Jianjun Zhao, Ma Xu, Clifford G Tepper, Christopher P Evans, Hsing-Jien Kung, and Ralph W deVere White. An androgen-regulated mirna suppresses bak1 expression and induces androgen-independent growth of prostate cancer cells. Proc Natl Acad Sci USA, 104(50):19983-19988, December 2007.

[30] D. F. Gleason and G. T. Mellinger. Prediction of prognosis for prostatic adenocarcinoma by combined histological grading and clinical staging. J Urol, 111(1):58-64, January 1974.

[31] Thijn R Brummelkamp, Ren Bernards, and Reuven Agami. A system for stable expression of short interfering rnas in mammalian cells. Science, 296(5567):550-553, April 2002.

[32] B. Saeed, H. Zhang, and S. C. Ng. Apoptotic program is initiated but not completed in lncap cells in response to growth in charcoal-stripped media. Prostate, 31(3):145-152, May 1997.

[33] Paolo Gandellini, Marco Folini, Nicole Longoni, Marzia Pennati, Mara Binda, Maurizio Colecchia, Roberto Salvioni, Rosanna Supino, Roberta Moretti, Patrizia Limonta, Riccardo Valdagni, Maria Grazia Daidone, and Nadia Zaffaroni. mir-205 exerts tumor-suppressive functions in human prostate through down-regulation of protein kinase cepsilon. Cancer Res, 69(6):2287-2295, March 2009.

[34] Feifei Xiao, Zhixiang Zuo, Guoshuai Cai, Shuli Kang, Xiaolian Gao, and Tongbin Li. mirecords: an integrated resource for microrna-target interactions. Nucleic Acids Res, 37(Database issue):D105-D110, January 2009.

[35] Yoav Benjamini and Yosef Hochberg. Controlling false discovery rate: a practical and powerful approach to multiple testing. Journal of the Royal Statistical Society B, 57(1):289-300, 1995.

[36] Shahriar Koochekpour, Yu-Jun Zhuang, Rameen Beroukhim, Chia-Ling Hsieh, Matthias D Hofer, Haiyen E Zhau, Masao Hiraiwa, Daniel Y Pattan, Joy L Ware, Ronald B Luftig, Konrad Sandhoff, Charles L Sawyers, Kenneth J Pienta, Mark A Rubin, Robert L Vessella, William R Sellers, and Oliver Sartor. Amplification and overexpression of prosaposin in prostate cancer. Genes Chromosomes Cancer, 44(4):351-364, December 2005.

[37] Shahriar Koochekpour, Tae-Jin Lee, Ruoxiang Wang, Zoran Culig, Nathalie Delorme, Soren Caffey, Luis Marrero, and Jennifer Aguirre. Prosaposin upregulates ar and psa expression and activity in prostate cancer cells (lncap). Prostate, 67(2):178-189, February 2007.

[38] C. D. Wolfgang, M. Essand, J. J. Vincent, B. Lee, and I. Pastan. Tarp: a nuclear protein expressed in prostate and breast cancer cells derived from an alternate reading frame of the t cell receptor gamma chain locus. Proc Natl Acad Sci USA, 97(17):9437-9442, August 2000.

[39] Wing-Shing Cheng, Valeria Giandomenico, Ira Pastan, and Magnus Essand. Characterization of the androgen-regulated prostate-specific t cell receptor gamma-chain alternate reading frame protein (tarp) promoter. Endocrinology, 144(8):3433-3440, August 2003.

[40] Weiqun Wang, Yuhua Li, Yang Li, Aizhen Hong, Jian Wang, Biaoyang Lin, and Runsheng Li. Ndrg3 is an androgen regulated and prostate enriched gene that promotes in vitro and in vivo prostate cancer cell growth. Int J Cancer, 124(3):521-530, February 2009.

[41] Gert-Jan C M van den Bemd, Jeroen Krijgsveld, Theo M Luider, Angelique L van Rijswijk, Jeroen A A Demmers, and Guido Jenster. Mass spectrometric identification of human prostate cancer-derived proteins in serum of xenograftbearing mice. Mol Cell Proteomics, 5(10):1830-1839, October 2006.

[42] Pascale V Nantermet, Jian Xu, Yuanjiang Yu, Paul Hodor, Daniel Holder, Sharon Adamski, Michael A Gentile, Donald B Kimmel, Shun-Ichi Harada, David Gerhold, Leonard P Freedman, and William J Ray. Identification of genetic pathways activated by the androgen receptor during the induction of proliferation in the ventral prostate gland. J Biol Chem, 279(2):1310-1322, January 2004.

[43] Soo-Yeon Park, Xiaofei Yu, Clement Ip, James L Mohler, Paul N Bogner, and Young-Mee Park. Peroxiredoxin 1 interacts with androgen receptor and enhances its transactivation. Cancer Res, 67(19):9294-9303, October 2007.

[44] Monica Davila, Andra R Frost, William E Grizzle, and Ratna Chakrabarti. Lim kinase 1 is essential for the invasive growth of prostate epithelial cells: implications in prostate cancer. J Biol Chem, 278(38):36868-36875, September 2003.

[45] Onikepe Adegbola and Gary R Pasternack. A pp 32-retinoblastoma protein complex modulates androgen receptor-mediated transcription and associates with components of the splicing machinery. Biochem Biophys Res Commun, 334(2):702-708, August 2005.

[46] Yaacov Hod. Differential control of apoptosis by dj-1 in prostate benign and cancer cells. J Cell Biochem, 92(6):1221-1233, August 2004.

[47] J. Erin Tillman, Jialing Yuan, Guangyu Gu, Ladan Fazli, Ritwik Ghosh, Alex S Flynt, Martin Gleave, Paul S Rennie, and Susan Kasper. Dj-1 binds androgen receptor directly and mediates its activity in hormonally treated prostate cancer cells. Cancer Res, 67(10):4630-4637, May 2007.

[48] Takehiko Segawa, Martin E Nau, Linda L Xu, Rao N Chilukuri, Mazen Makarem, Wei Zhang, Gyorgy Petrovics, Isabell A Sesterhenn, David G McLeod, Judd W Moul, Maryanne Vahey, and Shiv Srivastava. Androgeninduced expression of endoplasmic reticulum (er) stress response genes in prostate cancer cells. Oncogene, 21(57):8749-8758, December 2002.

[49] Tohru Miyagi, Osamu Hori, Kiyoshi Koshida, Masayuki Egawa, Hiroaki Kato, Yasuhide Kitagawa, Kentaro Ozawa, Satoshi Ogawa, and Mikio Namiki. Antitumor effect of reduction of 150-kda oxygen-regulated protein expression on human prostate cancer cells. Int J Urol, 9(10):577-585, October 2002.

[50] Xue-Ying He, Ying-Zi Yang, Donna M Peehl, Alexander Lauderdale, Horst Schulz, and Song-Yu Yang. Oxidative 3alpha-hydroxysteroid dehydrogenase activity of human type 10 17beta-hydroxysteroid dehydrogenase. J Steroid Biochem Mol Biol, 87(2-3):191-198, November 2003.

[51] M. E. Harper, E. Glynne-Jones, L. Goddard, D. W. Wilson, S. S. Matenhelia, I. G. Conn, W. B. Peeling, and K. Griffiths. Relationship of proliferating cell nuclear antigen (pcna) in prostatic carcinomas to various clinical parameters. Prostate, 20(3):243-253, 1992.

[52] Tiina Pitkänen-Arsiola, J. Erin Tillman, Guangyu Gu, Jialing Yuan, Richard L Roberts, Marcus Wantroba, Gerhard A Coetzee, Michael S Cookson, and Susan Kasper. Androgen and anti-androgen treatment modulates androgen receptor activity and dj-1 stability. Prostate, 66(11):1177-1193, August 2006.

[53] Katie L Meehan and Marianne D Sadar. Quantitative profiling of lncap prostate cancer cells using isotope-coded affinity tags and mass spectrometry. Proteomics, 4(4):1116-1134, April 2004.

[54] Alex Galanis, Aglaia Pappa, Antonis Giannakakis, Evripidis Lanitis, Denarda Dangaj, and Raphael Sandaltzopou-

[54] los. Reactive oxygen species and hif-1 signaling in cancer. Cancer Left, 266(1):12-20, July 2008.

[55] N. Zhu and Z. Wang. Calreticulin expression is associated with androgen regulation of the sensitivity to calcium ionophore-induced apoptosis in lncap prostate cancer cells. Cancer Res, 59(8):1896-1902, April 1999.

[56] J. M. Grad, L. S. Lyons, D. M. Robins, and K. L. Burnstein. The androgen receptor (ar) amino-terminus imposes androgen-specific regulation of ar gene expression via an exonic enhancer. Endocrinology, 142(3):1107-1116, March 2001.

[57] Janet L Stanford, Liesel M Fitzgerald, Shannon K McDonnell, Erin E Carlson, Laura M McIntosh, Kerry Deutsch, Lee Hood, Elaine A Ostrander, and Daniel J Schaid. Dense genome-wide snp linkage scan in 301 hereditary prostate cancer families identifies multiple regions with suggestive evidence for linkage. Hum Mol Genet, February 2009.

[58] P. H. Riegman, R. J. Vlietstra, J. A. van der Korput, A. O. Brinkmann, and J. Trapman The promoter of the prostate-specific antigen gene contains a functional androgen responsive element. Mol Endocrinol, 5(12):1921-1930, December 1991.

[59] P. Murtha, D. J. Tindall, and C. Y. Young. Androgen induction of a human prostate-specific kallikrein, hklk2: characterization of an androgen response element in the 5' promoter region of the gene. Biochemistry, 32(25):6459-6464, June 1993.

[60] J. T. Hsieh, H. C. Wu, M. E. Gleave, A. C. von Eschenbach, and L. W. Chung. Autocrine regulation of prostate-specific antigen gene expression in a human prostatic cancer (lncap) subline. Cancer Res, 53(12):2852-2857, June 1993.

[61] Carsten Stephan, Klaus Jung, Michael Lein, and Eleftherios P Diamandis. Psa and other tissue kallikreins for prostate cancer detection. Eur J Cancer, 43(13):1918-1926, September 2007.

[62] Kenneth J Pienta and Deborah Bradley. Mechanisms underlying the development of androgen-independent prostate cancer. Clin Cancer Res, 12(6):1665-1671, March 2006.

[63] Scott M Dehm and Donald J Tindall. Androgen receptor structural and functional elements: role and regulation in prostate cancer. Mol Endocrinol, 21(12):2855-2863, December 2007.

[64] R. Gentleman, V. J. Carey, W. Huber, R. A. Irizarry, and S. Dudoit. Bioinformatics and Computational Biology Solutions Using R and Bioconductor. Springer Science+Business Media, Inc., 2005.

[65] Gordon K Smyth. Linear models and empirical bayes methods for assessing differential expression in microarray experiments. Stat Appl Genet Mol Biol, 3:Article3, 2004.

[66] B. M. Bolstad, R. A. Irizarry, M. Astrand, and T. P. Speed. A comparison of normalization methods for high density oligonucleotide array data based on variance and bias. Bioinformatics, 19(2):185-193, January 2003.

[67] M. Veronica Gavrielides, Anatilde M Gonzalez-Guerrico, Natalia A Riobo, and Marcelo G Kazanietz. Androgens regulate protein kinase cdelta transcription and modulate its apoptotic function in prostate cancer cells. Cancer Res, 66(24):11792-11801, December 2006.

[68] S. Falcon and R. Gentleman. Using gostats to test gene lists for go term association. Bioinformatics, 23(2):257-258, January 2007.

[69] D. Benndorf, A. Müller, K. Bock, O. Manuwald, O. Herbarth, and M. von Bergen. Identification of spore allergens from the indoor mould *aspergillus* versicolor. Allergy, 63(4):454-460, April 2008.

[70] Matthias Berth, Frank Michael Moser, Markus Kolbe, and J"org Bernhardt. The state of the art in the analysis of two-dimensional gel electrophoresis images. Appl Microbiol Biotechnol, 76(6):1223-1243, October 2007.

[71] Dirk Benndorf, Gerd U Balcke, Hauke Harms, and Martin von Bergen. Functional metaproteome analysis of protein extracts from contaminated soil and groundwater. ISME J, 1(3):224-234, July 2007.

[72] Dessislava Georgieva, Michaela Risch, Anna Kardas, Friedrich Buck, Martin von Bergen, and Christian Betzel. Comparative analysis of the venom proteomes of vipera ammodytes ammodytes and vipera ammodytes meridionalis. J Proteome Res, 7(3):866-886, March 2008.

[73] Nico Jehmlich, Frank Schmidt, Martin von Bergen, Hans-Hermann Richnow, and Carsten Vogt. Protein-based stable isotope probing (protein-sip) reveals active species within anoxic mixed cultures. ISME J, 2(11):1122-1133, November 2008.

[74] van de Wetering M, Oving I, Muncan V, Pon Fong M T, Brantjes H, van Leenen D, Holstege F C, Brummelkamp T R, Agami R, Clevers H. Specific inhibition of gene expression using a stably integrated, inducible small-interfering-RNA vector. EMBO Rep. 2003 June; 4(6):609-15.

[75] Giering J C, Grimm D, Storm T A, Kay M A. Expression of shRNA from a tissue-specific pol II promoter is an effective and safe RNAi therapeutic. Mol. Ther. 2008 September; 16(9):1630-6. Epub 2008 Jul. 29.

[76] Grishok A, Pasquinelli A E, Conte D, Li N, Parrish S, Ha I, Baillie D L, Fire A, Ruvkun G, Mello C C. Genes and mechanisms related to RNA interference regulate expression of the small temporal RNAs that control C. elegans developmental timing Cell. 2001 Jul. 13; 106(1):23-34.

[77] Hutvágner G, McLachlan J, Pasquinelli A E, Mint E, Tuschl T, Zamore PD. A cellular function for the RNA-interference enzyme Dicer in the maturation of the let-7 small temporal RNA. Science. 2001 Aug. 3; 293(5531): 834-8. Epub 2001 Jul. 12.

[78] Ketting R F, Fischer S E, Bernstein E, Sijen T, Hannon G J, Plasterk R H. Dicer functions in RNA interference and in synthesis of small RNA involved in developmental timing in C. elegans. Genes Dev. 2001 Oct. 15; 15(20):2654-9.

[79] Lagos-Quintana M, Rauhut R, Lendeckel W, Tuschl T. Identification of novel genes coding for small expressed RNAs. Science. 2001 Oct. 26; 294(5543):853-8.

[80] Ohtsuka E, Matsuki S, Ikehara M, Takahashi Y, Matsubara K. An alternative approach to deoxyoligonucleotides as hybridization probes by insertion of deoxyinosine at ambiguous codon positions. J Biol. Chem. 1985 Mar. 10; 260(5):2605-8.

[81] Rossolini G M, Cresti S, Ingianni A, Cattani P, Riccio M L, Satta G. Use of deoxyinosine-containing primers vs degenerate primers for polymerase chain reaction based on ambiguous sequence information. Mol Cell Probes. 1994 April; 8(2):91-8.

[82] Cayouette M, Gravel C. Adenovirus-mediated gene transfer of ciliary neurotrophic factor can prevent photoreceptor degeneration in the retinal degeneration (rd) mouse. Hum Gene Ther. 1997 Mar. 1; 8(4):423-30.

[83] Naldini L, Blömer U, Gallay P, Ory D, Mulligan R, Gage F H, Verma I M, Trono D. In vivo gene delivery and stable transduction of nondividing cells by a lentiviral vector. Science. 1996 Apr. 12; 272(5259):263-7.

The invention claimed is:

1. A method for treating hormone-refractory prostate cancer comprising administering to a subject in need of said treating an effective amount of an isolated nucleic acid coding for a miRNA comprising or consisting of SEQ ID No:5 or a derivative or fragment thereof; and/or an optionally modified isolated nucleic acid comprising or consisting of SEQ ID No:5 or a derivative or fragment thereof, wherein said derivative displays a sequence identity of at least 90% to SEQ ID No:5 and wherein said fragment corresponds to a portion of at least 18 nucleotides of SEQ ID No:5.

2. The method of claim 1, wherein said isolated nucleic acid coding for said miRNA is a double stranded DNA.

3. The method of claim 2, wherein said double stranded DNA codes for a precursor of said miRNA, which is then processed to said miRNA.

4. The method of claim 2, wherein said double stranded DNA comprises the SEQ ID No:6 and the SEQ ID No:23 within the same polynucleotide strand, optionally separated by a spacer.

5. The method of claim 1, wherein said optionally modified isolated nucleic acid is a single stranded or doubled stranded RNA, of a length of 18 to 25 nucleotides.

6. The method of claim 1, wherein said optionally modified nucleic acid is modified by at least one modification selected from the group consisting of a 2'-O-methyl-ribonucleotide, a phosphorothioate bond, a N3'-P5' phosphoroamidate bond, a peptide-nucleic acid bond, a C-5 thiazole uracil, a C-5 propynyl-cytosine, a phenoxazine-modified cytosine, a 2'-O-propyl ribose and a 2'-methoxyethoxy ribose.

7. The method of claim 1, comprising administering to said subject additionally an effective amount of
an isolated nucleic acid coding for a miRNA comprising or consisting of SEQ ID No:2 or a derivative or fragment thereof; and/or an optionally modified isolated nucleic acid comprising or consisting of SEQ ID No:2 or a derivative or fragment thereof, wherein said derivative displays a sequence identity of at least 90% to SEQ ID No:2 and wherein said fragment corresponds to a portion of at least 18 nucleotides of SEQ ID No:2 and/or
an isolated nucleic acid coding for a miRNA comprising or consisting of SEQ ID No:8 or a derivative or fragment thereof; and/or an optionally modified isolated nucleic acid comprising or consisting of SEQ ID No:8 or a derivative or fragment thereof, wherein said derivative displays a sequence identity of at least 90% to SEQ ID No:8 and wherein said fragment corresponds to a portion of at least 18 nucleotides of SEQ ID No:8,
wherein said isolated nucleic acids coding for said miRNAs are optionally comprised within a single isolated nucleic acid.

8. The method of claim 3, wherein said precursor preferably comprises a stem-loop structure.

9. The method of claim 1, wherein said optionally modified isolated nucleic acid is a single stranded or doubled stranded RNA, of a length of 19 to 24 nucleotides.

10. The method of claim 1, wherein said optionally modified isolated nucleic acid is a single stranded or doubled stranded RNA, of a length of 20 to 22 nucleotides.

* * * * *